(12) United States Patent
Iyer et al.

(10) Patent No.: US 10,307,609 B2
(45) Date of Patent: Jun. 4, 2019

(54) COMPOSITIONS AND METHODS FOR CONTROLLING PAIN

(71) Applicants: The Board of Trustees of the Leland Stanford Junior University, Stanford, CA (US); Circuit Therapeutics, Inc., Menlo Park, CA (US)

(72) Inventors: Shrivats Mohan Iyer, Stanford, CA (US); Scott L. Delp, Stanford, CA (US); Kathryn L. Montgomery, Stanford, CA (US); Karl A. Deisseroth, Stanford, CA (US); Christopher Towne, San Francisco, CA (US)

(73) Assignees: The Board of Trustees of the Leland Stanford Junior University, Stanford, CA (US); Circuit Therapeutics, Inc., Menlo Park, CA (US)

( * ) Notice: Subject to any disclaimer, the term of this patent is extended or adjusted under 35 U.S.C. 154(b) by 0 days.

(21) Appl. No.: 14/911,405

(22) PCT Filed: Aug. 13, 2014

(86) PCT No.: PCT/US2014/050938
§ 371 (c)(1),
(2) Date: Feb. 10, 2016

(87) PCT Pub. No.: WO2015/023782
PCT Pub. Date: Feb. 19, 2015

(65) Prior Publication Data
US 2016/0199663 A1 Jul. 14, 2016

Related U.S. Application Data

(60) Provisional application No. 61/865,962, filed on Aug. 14, 2013.

(51) Int. Cl.
*A61N 5/06* (2006.01)
*A01K 67/027* (2006.01)
*A61K 38/16* (2006.01)
*A61K 41/00* (2006.01)
*A61K 48/00* (2006.01)
*C12N 15/85* (2006.01)

(52) U.S. Cl.
CPC .......... *A61N 5/062* (2013.01); *A01K 67/0275* (2013.01); *A01K 67/0278* (2013.01); *A61K 38/16* (2013.01); *A61K 41/00* (2013.01); *A61K 48/0058* (2013.01); *A61K 48/0075* (2013.01); *A61N 5/0622* (2013.01); *C12N 15/8509* (2013.01); *A01K 2207/15* (2013.01); *A01K 2217/07* (2013.01); *A01K 2217/072* (2013.01); *A01K 2227/105* (2013.01); *A01K 2267/03* (2013.01); *A01K 2267/0393* (2013.01); *C12N 2015/8527* (2013.01); *C12N 2750/14141* (2013.01)

(58) Field of Classification Search
None
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,411,540 A | 5/1995 | Edell et al. |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |

(Continued)

FOREIGN PATENT DOCUMENTS

| | | |
|---|---|---|
| CN | 1079464 A | 12/1993 |
| CN | 1558222 A | 12/2004 |

(Continued)

OTHER PUBLICATIONS

Schuster, et al. (2014) "Biodistribution of adeno-associated virus serotype 9 (AAV9) vector after intrathecal and intravenous delivery in mouse", Frontiers in Neuroanatomy, 8:42, pp. 1-41.*

(Continued)

*Primary Examiner* — Robert M Kelly
(74) *Attorney, Agent, or Firm* — Bozicevic, Field & Francis LLP; Paula A. Borden

(57) ABSTRACT

The present disclosure provides compositions and methods for controlling pain. The present disclosure provides methods for identifying agents that control pain.

20 Claims, 18 Drawing Sheets
Specification includes a Sequence Listing.

(56) References Cited

U.S. PATENT DOCUMENTS

| | | |
|---|---|---|
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |
| 5,836,941 A | 11/1998 | Yoshihara et al. |
| 5,898,058 A | 4/1999 | Nichols |
| 5,939,320 A | 8/1999 | Littman et al. |
| 6,056,738 A | 5/2000 | Marchitto et al. |
| 6,057,114 A | 5/2000 | Akong |
| 6,108,081 A | 8/2000 | Holtom et al. |
| 6,134,474 A | 10/2000 | Fischell et al. |
| 6,161,045 A | 12/2000 | Fischell et al. |
| 6,180,613 B1 | 1/2001 | Kaplitt et al. |
| 6,253,109 B1 | 6/2001 | Gielen |
| 6,289,229 B1 | 9/2001 | Crowley |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,346,101 B1 | 2/2002 | Alfano et al. |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,808,873 B2 | 10/2004 | Murphy et al. |
| 6,810,285 B2 | 10/2004 | Pless et al. |
| 6,889,085 B2 | 5/2005 | Dawson |
| 6,918,872 B2 | 7/2005 | Yokoi |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,883,536 B1 | 2/2011 | Bendett |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,401,609 B2 | 3/2013 | Deisseroth et al. |
| 8,603,790 B2 | 12/2013 | Deisseroth et al. |
| 8,696,722 B2 | 4/2014 | Deisseroth et al. |
| 8,716,447 B2 | 5/2014 | Deisseroth et al. |
| 8,729,040 B2 | 5/2014 | Deisseroth et al. |
| 8,815,582 B2 | 8/2014 | Deisseroth et al. |
| 8,834,546 B2 | 9/2014 | Deisseroth et al. |
| 8,864,805 B2 | 10/2014 | Deisseroth et al. |
| 8,906,360 B2 | 12/2014 | Deisseroth et al. |
| 8,926,959 B2 | 1/2015 | Deisseroth et al. |
| 8,932,562 B2 | 1/2015 | Deisseroth et al. |
| 8,956,363 B2 | 2/2015 | Deisseroth et al. |
| 8,962,589 B2 | 2/2015 | Deisseroth et al. |
| 9,057,734 B2 | 6/2015 | Cohen |
| 9,079,940 B2 | 7/2015 | Deisseroth et al. |
| 9,084,885 B2 | 7/2015 | Deisseroth et al. |
| 9,101,690 B2 | 8/2015 | Deisseroth et al. |
| 9,101,759 B2 | 8/2015 | Deisseroth et al. |
| 9,175,095 B2 | 11/2015 | Deisseroth et al. |
| 9,187,745 B2 | 11/2015 | Deisseroth et al. |
| 9,238,150 B2 | 1/2016 | Deisseroth et al. |
| 9,249,200 B2 | 2/2016 | Deisseroth et al. |
| 9,249,234 B2 | 2/2016 | Deisseroth et al. |
| 9,271,674 B2 | 3/2016 | Deisseroth et al. |
| 9,274,099 B2 | 3/2016 | Deisseroth et al. |
| 9,278,159 B2 | 3/2016 | Deisseroth et al. |
| 9,309,296 B2 | 4/2016 | Deisseroth et al. |
| 9,340,589 B2 | 5/2016 | Deisseroth et al. |
| 9,359,449 B2 | 6/2016 | Deisseroth et al. |
| 9,421,258 B2 | 8/2016 | Deisseroth et al. |
| 9,458,208 B2 | 10/2016 | Deisseroth et al. |
| 9,522,288 B2 | 12/2016 | Deisseroth et al. |
| 9,604,073 B2 | 3/2017 | Deisseroth et al. |
| 9,636,380 B2 | 5/2017 | Deisseroth et al. |
| 9,850,290 B2 | 12/2017 | Deisseroth et al. |
| 9,968,652 B2 | 5/2018 | Deisseroth et al. |
| 10,064,912 B2 | 9/2018 | Deisseroth et al. |
| 10,071,132 B2 | 9/2018 | Deisseroth et al. |
| 2001/0023346 A1 | 9/2001 | Loeb |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2002/0190922 A1 | 12/2002 | Tsao |
| 2002/0193327 A1 | 12/2002 | Nemerow et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0082809 A1 | 5/2003 | Quail et al. |
| 2003/0088060 A1 | 5/2003 | Benjamin et al. |
| 2003/0097122 A1 | 5/2003 | Ganz et al. |
| 2003/0103949 A1 | 6/2003 | Carpenter et al. |
| 2003/0104512 A1 | 6/2003 | Freeman et al. |
| 2003/0125719 A1 | 7/2003 | Furnish |
| 2003/0144650 A1 | 7/2003 | Smith |
| 2003/0204135 A1 | 10/2003 | Bystritsky |
| 2003/0232339 A1 | 12/2003 | Shu et al. |
| 2004/0013645 A1 | 1/2004 | Monahan et al. |
| 2004/0015211 A1 | 1/2004 | Nurmikko et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0049134 A1 | 3/2004 | Tosaya et al. |
| 2004/0068202 A1 | 4/2004 | Hansson et al. |
| 2004/0073278 A1 | 4/2004 | Pachys |
| 2004/0076613 A1 | 4/2004 | Mazarkis et al. |
| 2004/0122475 A1 | 6/2004 | Myrick et al. |
| 2004/0203152 A1 | 10/2004 | Calos |
| 2004/0216177 A1 | 10/2004 | Jordan et al. |
| 2004/0260367 A1 | 12/2004 | Taboada et al. |
| 2004/0267118 A1 | 12/2004 | Dawson |
| 2005/0020945 A1 | 1/2005 | Tosaya et al. |
| 2005/0027284 A1 | 2/2005 | Lozano et al. |
| 2005/0058987 A1 | 3/2005 | Shi et al. |
| 2005/0088177 A1 | 4/2005 | Schreck et al. |
| 2005/0102708 A1 | 5/2005 | Lecanu et al. |
| 2005/0107753 A1 | 5/2005 | Rezai et al. |
| 2005/0112759 A1 | 5/2005 | Radisic et al. |
| 2005/0119315 A1 | 6/2005 | Fedida et al. |
| 2005/0124897 A1 | 6/2005 | Chopra |
| 2005/0143295 A1 | 6/2005 | Walker et al. |
| 2005/0143790 A1 | 6/2005 | Kipke et al. |
| 2005/0153885 A1 | 7/2005 | Yun et al. |
| 2005/0197679 A1 | 9/2005 | Dawson |

(56) References Cited

U.S. PATENT DOCUMENTS

| | | |
|---|---|---|
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2005/0279354 A1 | 12/2005 | Deutsch et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0129126 A1 | 6/2006 | Kaplitt et al. |
| 2006/0155348 A1 | 7/2006 | de Charms |
| 2006/0161227 A1 | 7/2006 | Walsh et al. |
| 2006/0167500 A1 | 7/2006 | Towe et al. |
| 2006/0179501 A1 | 8/2006 | Chan et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0027443 A1 | 2/2007 | Rose et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0060984 A1 | 3/2007 | Webb et al. |
| 2007/0135875 A1 | 6/2007 | Demarais et al. |
| 2007/0156180 A1 | 7/2007 | Jaax et al. |
| 2007/0191906 A1 | 8/2007 | Iyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand |
| 2007/0260295 A1 | 11/2007 | Chen et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0046053 A1 | 1/2008 | Wagner et al. |
| 2008/0033569 A1 | 2/2008 | Ferren et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0088258 A1 | 4/2008 | Ng |
| 2008/0103551 A1 | 5/2008 | Masoud et al. |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0069261 A1 | 3/2009 | Dodge et al. |
| 2009/0088680 A1 | 4/2009 | Deisseroth et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0131837 A1 | 5/2009 | Granville |
| 2009/0148861 A1 | 6/2009 | Pegan et al. |
| 2009/0157145 A1 | 6/2009 | Cauller |
| 2009/0254134 A1 | 10/2009 | Nikolov et al. |
| 2009/0268511 A1 | 10/2009 | Birge et al. |
| 2009/0306474 A1 | 12/2009 | Wilson |
| 2009/0319008 A1 | 12/2009 | Mayer |
| 2009/0326603 A1 | 12/2009 | Boggs et al. |
| 2010/0009444 A1 | 1/2010 | Herlitze et al. |
| 2010/0016783 A1 | 1/2010 | Bourke et al. |
| 2010/0021982 A1 | 1/2010 | Herlitze |
| 2010/0145418 A1 | 6/2010 | Zhang et al. |
| 2010/0146645 A1 | 6/2010 | Vasar et al. |
| 2010/0190229 A1 | 7/2010 | Deisseroth et al. |
| 2010/0209352 A1 | 8/2010 | Hultman et al. |
| 2010/0234273 A1 | 9/2010 | Deisseroth et al. |
| 2011/0221970 A1 | 1/2011 | Vo-Dihn et al. |
| 2011/0092800 A1 | 4/2011 | Yoo et al. |
| 2011/0105998 A1 | 5/2011 | Deisseroth et al. |
| 2011/0112463 A1 | 5/2011 | Silver et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0165681 A1 | 7/2011 | Boyden et al. |
| 2011/0166632 A1 | 7/2011 | Delp et al. |
| 2011/0233046 A1 | 9/2011 | Nikolenko et al. |
| 2011/0301529 A1 | 12/2011 | Deisseroth et al. |
| 2011/0311489 A1 | 12/2011 | Deisseroth et al. |
| 2012/0093772 A1 | 4/2012 | Horsager et al. |
| 2012/0121542 A1 | 5/2012 | Chuong et al. |
| 2012/0165904 A1 | 6/2012 | Deisseroth et al. |
| 2012/0253261 A1 | 10/2012 | Poletto et al. |
| 2013/0019325 A1 | 1/2013 | Deisseroth et al. |
| 2013/0030275 A1 | 1/2013 | Seymour et al. |
| 2013/0089503 A1 | 4/2013 | Deisseroth et al. |
| 2013/0144359 A1 | 6/2013 | Kishawi et al. |
| 2013/0284920 A1 | 10/2013 | Deisseroth et al. |
| 2013/0286181 A1 | 10/2013 | Betzig et al. |
| 2013/0288365 A1 | 10/2013 | Deisseroth et al. |
| 2013/0289669 A1 | 10/2013 | Deisseroth et al. |
| 2013/0289675 A1 | 10/2013 | Deisseroth et al. |
| 2013/0296406 A1 | 11/2013 | Deisseroth et al. |
| 2013/0317569 A1 | 11/2013 | Deisseroth et al. |
| 2013/0317575 A1 | 11/2013 | Deisseroth et al. |
| 2013/0330816 A1 | 12/2013 | Deisseroth et al. |
| 2013/0343998 A1 | 12/2013 | Deisseroth et al. |
| 2013/0347137 A1 | 12/2013 | Deisseroth et al. |
| 2014/0082758 A1 | 3/2014 | Deisseroth et al. |
| 2014/0148880 A1 | 5/2014 | Deisseroth et al. |
| 2014/0235826 A1 | 8/2014 | Deisseroth et al. |
| 2014/0271479 A1 | 9/2014 | Lammel et al. |
| 2014/0324133 A1 | 10/2014 | Deisseroth et al. |
| 2015/0040249 A1 | 2/2015 | Deisseroth et al. |
| 2015/0072394 A1 | 3/2015 | Deisseroth et al. |
| 2015/0112411 A1 | 4/2015 | Beckman et al. |
| 2015/0165227 A1 | 6/2015 | Deisseroth et al. |
| 2015/0174244 A1 | 6/2015 | Deisseroth et al. |
| 2015/0217128 A1 | 8/2015 | Deisseroth et al. |
| 2015/0218547 A1 | 8/2015 | Deisseroth et al. |
| 2015/0297719 A1 | 10/2015 | Deisseroth et al. |
| 2016/0002302 A1 | 1/2016 | Deisseroth et al. |
| 2016/0015996 A1 | 1/2016 | Deisseroth et al. |
| 2016/0038764 A1 | 2/2016 | Deisseroth et al. |
| 2016/0045599 A1 | 2/2016 | Deisseroth et al. |

FOREIGN PATENT DOCUMENTS

| | | |
|---|---|---|
| CN | 1781019 A | 5/2006 |
| CN | 102076866 A | 5/2011 |
| CN | 103313752 A | 9/2013 |
| CN | 103476456 A | 12/2013 |
| EP | 1197144 | 4/2002 |
| EP | 1334748 | 8/2003 |
| EP | 1444889 | 8/2004 |

(56) References Cited

FOREIGN PATENT DOCUMENTS

| | | |
|---|---|---|
| EP | 1873566 | 1/2008 |
| JP | 6295350 | 10/1994 |
| JP | H 09505771 A | 6/1997 |
| JP | 2004534508 | 11/2004 |
| JP | 2005034073 A | 2/2005 |
| JP | 2006217866 | 8/2006 |
| JP | 2007530027 A | 11/2007 |
| JP | 2008010422 A | 1/2008 |
| JP | 2010227537 A | 10/2010 |
| JP | 2012508581 | 4/2012 |
| WO | WO 1995/005214 | 2/1995 |
| WO | WO 1996/032076 | 10/1996 |
| WO | WO 2000/027293 | 5/2000 |
| WO | WO 2001/025466 | 4/2001 |
| WO | WO 2003/016486 | 2/2003 |
| WO | WO 2003/040323 | 5/2003 |
| WO | WO 2003/046141 | 6/2003 |
| WO | WO 2003/084994 | 10/2003 |
| WO | WO 2003/102156 | 12/2003 |
| WO | WO 2004/033647 | 4/2004 |
| WO | WO 2005/093429 | 10/2005 |
| WO | WO 2006/103678 | 10/2006 |
| WO | WO 2007/024391 | 3/2007 |
| WO | WO 2007/131180 | 11/2007 |
| WO | WO 2008/014382 | 1/2008 |
| WO | WO 2008/086470 | 7/2008 |
| WO | WO 2008/106694 | 9/2008 |
| WO | WO 2009/025819 | 2/2009 |
| WO | WO 2009/072123 | 6/2009 |
| WO | WO 2009/119782 | 10/2009 |
| WO | WO 2009/131837 | 10/2009 |
| WO | WO 2009/148946 | 12/2009 |
| WO | WO 2010/006049 | 1/2010 |
| WO | WO 2010/011404 | 1/2010 |
| WO | WO 2010/056970 | 5/2010 |
| WO | WO 2010/123993 | 10/2010 |
| WO | WO 2011/005978 | 1/2011 |
| WO | WO 2011/066320 | 6/2011 |
| WO | WO 2011/106783 | 9/2011 |
| WO | WO 2011/116238 | 9/2011 |
| WO | WO 2011/127088 | 10/2011 |
| WO | WO 2012/032103 | 3/2012 |
| WO | WO 2012/061676 | 5/2012 |
| WO | WO 2012/061681 | 5/2012 |
| WO | WO 2012/061684 | 5/2012 |
| WO | WO 2012/061688 | 5/2012 |
| WO | WO 2012/061690 | 5/2012 |
| WO | WO 2012/061741 | 5/2012 |
| WO | WO 2012/061744 | 5/2012 |
| WO | WO 2012/106407 | 8/2012 |
| WO | WO 2012/134704 | 10/2012 |
| WO | WO 2013/003557 | 1/2013 |
| WO | WO 2013/016486 | 1/2013 |
| WO | WO 2013/090356 | 6/2013 |
| WO | WO 2013/126521 | 8/2013 |
| WO | WO 2013/126762 | 8/2013 |
| WO | WO 2013/142196 | 9/2013 |
| WO | WO 2014/081449 | 5/2014 |
| WO | WO 2014/117079 | 7/2014 |
| WO | WO 2016/019075 | 2/2016 |

OTHER PUBLICATIONS

Johnson, et al. (2006) "Differential biodistribution of adenoviral vector in vivo as monitored by bioluminescence imaging and quantitative polymerase chain reaction", Human Gene Therapy, 17(12): 1262-69.*
Rancaniello 2013 http://www.virology.ws/2013/09/06/how-many-viruses-on-earth/, Virology Blog, No journal, no volume, no issue, 6 pages printed.*
Azizgolshani, et al. (2013) "Reconstituted plant viral capsid can release genes to mammalian cells", Virology, 441(1): 12-17.*

Davidson, et al.; "Viral Vectors for Gene Delivery to the Nervous System"; Nature Reviews Neuroscience; vol. 4, pp. 353-364 (May 2003).
Fanselow, et al.; "Why We Think Plasticity Underlying Pavlovian Fear Conditioning Occurs in the Basolateral Amygdala"; Neuron; vol. 23, pp. 229-232 (Jun. 1999).
Rogers, et al.; "Effects of ventral and dorsal CA1 subregional lesions on trace fear conditioning"; Neurobiology of Learning and Memory; vol. 86, pp. 72-81 (2006).
Jones, et al.; "Animal Models of Schizophrenia"; British Journal of Pharmacology; vol. 164, pp. 1162-1194 (2011).
Airan, et al.; "Integration of light-controlled neuronal firing and fast circuit imaging"; Current Opinion in Neurobiology; vol. 17, pp. 587-592 (2007).
Cannon, et al.; "Endophenotypes in the Genetic Analyses of Mental Disorders"; Annu. Rev. Clin. Psychol.; vol. 2, pp. 267-290 (2006).
Chamanzar, et al.; "Deep Tissue Targeted Near-infrared Optogenetic Stimulation using Fully Implantable Upconverting Light Bulbs"; 2015 37th Annual International Conference of the IEEE Engineering in Medicine and Biology Society (EMBC), IEEE; doi: 10.1109/EMBC.2015.7318488, pp. 821-824 (Aug. 25, 2015).
Chinta, et al.; "Dopaminergic neurons"; The International Journal of Biochemistry & Cell Biology; vol. 37, pp. 942-946 (2005).
Deonarain; "Ligand-targeted receptor-mediated vectors for gene delivery"; Exp. Opin. Ther. Patents; vol. 8, No. 1, pp. 53-69 (1998).
Edelstein, et al.; "Gene therapy clinical trials worldwide 1989-2004—an overview"; The Journal of Gene Medicine; vol. 6, pp. 597-602 (2004).
Grady, et al.; "Age-Related Reductions in Human Recognition Memory Due to Impaired Encoding"; Science; vol. 269, No. 5221, pp. 218-221 (Jul. 14, 1995).
Hososhima, et al.; "Near-infrared (NIR) up-conversion optogenetics"; Optical Techniques in Neurosurgery, Neurophotonics, and Optogenetics II; vol. 9305, doi: 10.1117/12.2078875, 4 pages (2015).
Johnson-Saliba, et al.; "Gene Therapy: Optimising DNA Delivery to the Nucleus"; Current Drug Targets; vol. 2, pp. 371-399 (2001).
Palu, et al.; "In pursuit of new developments for gene therapy of human diseases"; Journal of Biotechnology; vol. 68, pp. 1-13 (1999).
Petersen, et al.; "Functionally Independent Columns of Rat Somatosensory Barrel Cortex Revealed with Voltage-Sensitive Dye Imaging"; J. of Neuroscience; vol. 21, No. 21, pp. 8435-8446 (Nov. 1, 2011).
Pfeifer, et al.; "Gene Therapy: Promises and Problems"; Annu. Rev. Genomics Hum. Genet.; vol. 2, pp. 177-211 (2001).
Powell, et al.; "Schizophrenia-Relevant Behavioral Testing in Rodent Models: A Uniquely Human Disorder?"; Biol. Psychiatry; vol. 59, pp. 1198-1207 (2006).
Shoji, et al.; "Current Status of Delivery Systems to Improve Target Efficacy of Oligonucleotides"; Current Pharmaceutical Design; vol. 10, pp. 785-796 (2004).
Verma, et al.; "Gene therapy—promises, problems and prospects"; Nature; vol. 389, pp. 239-242 (Sep. 1997).
Wang, et al.; "Simultaneous phase and size control of upconversion nanocrystals through lanthanide doping"; Nature; vol. 463, No. 7284, pp. 1061-1065 (Feb. 25, 2010).
Yajima, et al., "Effects of bromazepam on responses of mucosal blood flow of the gastrointestinal tract and the gastric motility to stimulation of the amygdala and hypothalamus in conscious cats"; Folia Pharmacol. Japon; vol. 83, No. 3, pp. 237-248 (Mar. 1984). [English abstract translation].
Yamada, Shigeto; "Neurobiological Aspects of Anxiety Disorders"; The Japanese Journal of Psychiatry; vol. 8, No. 6, pp. 525-535 (Nov. 25, 2003). [English translation of introduction and summary].
Chow, et al.; "High-performance genetically targetable optical neural silencing by light-driven proton pumps"; Nature; vol. 463, pp. 98-102 (Jan. 7, 2010).
Gong, et al.; "Enhanced Archaerhodopsin Fluorescent Protein Voltage Indicators"; PLOS One; vol. 8, Issue 6, 10 pages (Jun. 2013).
Han, et al.; "A high-light sensitivity optical neural silencer: development and application to optogenetic control of non-human primate cortex"; Frontiers in Systems Neuroscience; vol. 5, Article 18, pp. 1-8 (Apr. 2011).
Co-pending U.S. Appl. No. 14/822,552, filed Aug. 10, 2015.

(56) References Cited

OTHER PUBLICATIONS

Co-pending U.S. Appl. No. 14/886,763, filed Oct. 19, 2015.
Co-pending U.S. Appl. No. 14/911,405, filed Feb. 26, 2016.
Co-pending U.S. Appl. No. 15/008,214, filed Jan. 27, 2016.
Co-pending U.S. Appl. No. 15/059,159, filed Mar. 2, 2016.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Aebischer, et al. "Long-Term Cross-Species Brain Transplantation of a Polymer-Encapsulated Dopamine-Secreting Cell Line", Experimental Neurology, 1991, vol. 111, pp. 269-275.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ali; "Gene and stem cell therapy for retinal disorders"; vision-research.en—The Gateway to European Vision Research; accessed from http://www.vision-research.eu/index.php?id=696, 10 pages (accessed Jul. 24, 2015).
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the cre Gene Mediated by Cre Recombinase Using a Combination of Mutant lox Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Arenkiel, et al. "In vivo light-induced activation of neural circuitry in transgenic mice expressing Channelrhodopsin-2", Neuron, 2007, 54:205-218.
Argos, et al. "The integrase family of site-specific recombinases: regional similarities and global diversity", The EMBO Journal, 1986, vol. 5, No. 2, pp. 433-440.
Asano, et al.; "Optically Controlled Contraction of Photosensitive Skeletal Muscle Cells"; Biotechnology & Bioengineering; vol. 109, No. 1, pp. 199-204 (Jan. 2012).
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Babin et al., "Zebrafish Models of Human Motor Neuron Diseases: Advantages and Limitations", Progress in Neurobiology (2014), 118:36-58.
Balint et al., "The Nitrate Transporting Photochemical Reaction Cycle of the Pharanois Halorhodopsin", Biophysical Journal, 2004, 86:1655-1663.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Barchet, et al.; "Challenges and opportunities in CNS delivery of therapeutics for neurodegenerative diseases"; Expert Opinion on Drug Delivery; vol. 6, No. 3, pp. 211-225 (Mar. 16, 2009).
Basil et al.; "Is There Evidence for Effectiveness of Transcranial Magnetic Stimulation in the Treatment of Psychiatric Disorders?"; Psychiatry; vol. 1, No. 11, pp. 64-69 (Nov. 2005).
Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berke, et al. "Addiction, Dopamine, and the Molecular Mechanisms of Memory", Molecular Plasticity, 2000, vol. 25: pp. 515-532.
Berlanga, et a.; "Cholinergic Interneurons of the Nucleus Accumbens and Dorsal Striatum are Activated by the Self-Administration of Cocaine"; Neuroscience; vol. 120, pp. 1149-1156 (2003).
Berndt et al. "Bi-stable neural state switches", Nature Neuroscience, 2008, vol. 12, No. 2: pp. 229-234.
Berndt et al., "Structure-guided transformation of channelrhodopsin into a light-activated chloride channel", Science, 2014, 344:420-424.
Berridge et al., "The Versatility and Universality of Calcium Signaling", Nature Reviews: Molecular Cell Biology, 2000, vol. 1: pp. 11-21.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Post-synaptic Cell Type", Journal of Neuroscience, 1998, vol. 18, No. 24: pp. 10464-10472.
Blomer et al., "Highly Efficient and Sustained Gene Transfer in Adult Neurons with Lentivirus Vector", Journal of Virology,1997, vol. 71, No. 9: pp. 6641-6649.
Bocquet et al. "A prokaryotic proton-gated ion channel from the nicotinic acetylcholine receptor family." Nature Letters, 2007, vol. 445, p. 116-119.
Bowers, et al.; "Genetic therapy for the nervous system"; Human Molecular Genetics; vol. 20, No. 1, pp. R28-R41 (2011).
Boyden, et al. "Millisecond-timescale, genetically targeted optical control of neural activity" Nature Neuroscience, 2005, vol. 8, No. 9: pp. 1263-1268.
Braun, "Two Light-activated Conductances in the Eye of the Green Alga Volvox carteri", 1999, Biophys J., vol. 76, No. 3, pp. 1668-1678.
Brewin; "The Nature and Significance of Memory Disturbance in Posttraumatic Stress Disorder"; Ann. Rev. Clin. Psychol.; vol. 7, pp. 203-227 (2011).
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by $\theta$ frequency stimulation is regulated by a protein phosphate-operated gate." The Journal of Neuroscience, 2000, vol. 20, No. 21, pp. 7880-7887.
Bruegmann, et al.; "Optogenetic control of heart muscle in vitro and in vivo"; Nature Methods; vol. 7, No. 11, pp. 897-900(Nov. 2010).
Bruegmann, et al.; "Optogenetics in cardiovascular research: a new tool for light-induced depolarization of cardiomyocytes and vascular smooth muscle cells in vitro and in vivo"; European Heart Journal; vol. 32, No. Suppl . 1, p. 997 (Aug. 2011).
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cardin, et al. "Driving Fast spiking Cells Induces Gamma Rhythm and Controls Sensory Responses", 2009, Nature, vol. 459, vol. 7247, pp. 663-667.

(56) References Cited

OTHER PUBLICATIONS

Castagne, et al.; "Rodent Models of Depression: Forced Swim and Tail Suspension Behavioral Despair Tests in Rats and Mice"; Current Protocols in Pharmacology; Supp. 49, Unit 5.8.1-5.8.14 (Jun. 2010).
Cazillis, et al., "VIP and PACAP induce selective neuronal differentiation of mouse embryonic stem cells", Eur J Neurosci, 2004, 19(4):798-808.
Cenatiempo "Prokaryotic gene expression in vitro: transcription-translation coupled systems", Biochimie, 1986, vol. 68(4): pp. 505-515.
Chow et al., "Optogenetics and translation medicine", Sci Transl Med., 2013, 5(177):177.
Clark, et al.; "A future for transgenic livestock"; Nature Reviews Genetics; vol. 4, No. 10, pp. 825-833 (Oct. 2003).
Claudio et al. "Nucleotide and deduced amino acid sequences of Torpedo californica acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Crouse, et al. "Expression and amplification of engineered mouse dihydrofolate reductase minigenes" Mol. Cell. Biol., 1983, vol. 3(2): pp. 257-266.
Cucchiaro et al., "Electron-Microscopic Analysis of Synaptic Input from the Perigeniculate Nucleus to A-Laminae of the Lateral Geniculate Nucleus in Cats", The Journal of Comparitive Neurology, 1991, vol. 310, pp. 316-336.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cui, et al., "Electrochemical deposition and characterization of conducting polymer polypyrrole/PSS on multichannel neural probes," Sensors and Actuators, 2001, vol. 93(1): pp. 8-18.
Dalva, et al. "Rearrangements of Synaptic Connections in Visual Cortex Revealed by Laser Photostimulation", Science, 1994,vol. 265, pp. 255-258.
Date, et al. "Grafting of Encapsulated Dopamine-Secreting Cells in Parkinson's Disease: Long-Term Primate Study", Cell Transplant, 2000, vol. 9, pp. 705-709.
Davis; "The many faces of epidermal growth factor repeats," The New Biologist; vol. 2, No. 5, pp. 410-419 (1990).
Day, et al.; "The Nucleus Accumbens and Pavlovian Reward Learning"; Neuroscientist; vol. 13, No. 2, pp. 148-159 (Apr. 2007).
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
De Palma, et al.; "In Vivo Targeting of Tumor Endothelial Cells by Systemic Delivery of Lentiviral Vectors"; Human Gene Therapy; vol. 14, pp. 1193-1206 (Aug. 10, 2003).
Dederen, et al. "Retrograde neuronal tracing with cholera toxin B subunit: comparison of three different visualization methods", Histochemical Journal, 1994, vol. 26, pp. 856-862.
Definition of Psychosis (2015).
Deisseroth "Next-generation optical technologies for illuminating genetically targeted brain circuits," The Journal of Neuroscience, 2006, vol. 26, No. 41, pp. 10380-10386.
Deisseroth et al., "Excitation-neurogenesis Coupling in Adult Neural Stem/Progenitor Cells", 2004, Neuron, vol. 42, pp. 535-552.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Signaling from Synapse to Nucleus: the logic Behind the Mechanisms", Currrent Opinion in Neurobiology, 2003, vol. 13, pp. 354-365.
Deisseroth et al., "Translocation of Calmodulin to the Nucleus Supports CREB Phosphorylation in Hippocampal Neurons", Nature, 1998, vol. 392, pp. 198-202.
Deisseroth, et al., "Controlling the Brain with Light", Scientific American, 2010, vol. 303, pp. 48-55.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 10I, No. 52, pp. 18206-18211.
Do Carmo, et al.; "Modeling Alzheimer's disease in transgenic rats"; Molecular Neurodegeneration; vol. 8, No. 37, 11 pages (2013).
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Ebert et al., "A Moloney MLV-rat somatotropin fusion gene produces biologically active somatotropin in a transgenic pig", Mol. Endocrinology, 1988, vol. 2, pp. 277-283.
EBI accession No. EMBL: J05199; "N. pharaonis halorhodopsin (hop) gene, complete cds"; (Nov. 22, 1990).
EBI accession No. UNIPROT: A7U0Y6; "SubName: Full=Bacteriorhodopsin"; (Aug. 10, 2010).
EBI accession No. UNIPROT: B0R5N9; "Subname: Full=Bacteriorhodopsin"; (Apr. 8, 2008).
EBI accession No. UNIPROT: B4Y103; "SubName: Full=Channelrhodopsin-1"; (Sep. 23, 2008).
EBI accession No. UNIPROT: P15647; "RecName: Full=Halorhodopsin; Short=HR; Alt Name: Full=NpHR"; (Apr. 1, 1990).
Ehrlich I. et al. "Amygdala inhibitory circuits and the control of fear memory", Neuron, 2009, vol. 62: pp. 757-771.
Eijkelkamp, et al. "Neurological perspectives on voltage-gated sodium channels", Brain, 2012, 135:2585-2612.
Eisen, "Treatment of amyotrophic lateral sclerosis", Drugs Aging, 1999; vol. 14, No. 3, pp. 173-196.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Ernst, et al. "Photoactivation of Channelrhodopsin", J. Biol. Chem., 2008, vol. 283, No. 3, pp. 1637-1643.
Esposito et al. "The integrase family of tyrosine recombinases: evolution of a conserved active site domain" , Nucleic Acids Research, 1997, vol. 25, No. 18, pp. 3605-3614.
Evanko "Optical excitation yin and yang" Nature Methods, 2007, 4:384.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fenno et al., "The development and application of optogenetics", Annual Review of Neuroscience, 2011, vol. 34, No. 1, pp. 389-412.

(56) References Cited

OTHER PUBLICATIONS

Fiala et al., "Optogenetic approaches in neuroscience", Current Biology, Oct. 2010, 20(20):R897-R903.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Fox et al., "A gene neuron expression fingerprint of C. elegans embryonic motor neurons", BMC Genomics, 2005, 6(42):1-23.
Friedman, et al.; "Programmed Acute Electrical Stimulation of Ventral Tegmental Area Alleviates Depressive-Like Behavior"; Neuropsychopharmacology; vol. 34, pp. 1057-1066 (2009).
Garrido et al., "A targeting motif involved in sodium channel clustering at the axonal initial segment", Science, 2003, vol. 300, No. 5628, pp. 2091-2094.
Gelvich et al. "Contact flexible microstrip applicators (CFMA) in a range from microwaves up to short waves," IEEE Transactions on Biomedical Engineering, 2002, vol. 49, Issue 9: 1015-1023.
Genbank Accession No. AAG01180.1; Idnurm, et al.; pp. 1 (Mar. 21, 2001).
Genbank Accession No. ABT17417.1; Sharma, et al.; pp. 1 (Aug. 15, 2007).
GenBank Accession No. AC096118.6; Rattus norvegicus clone CH230-11 B15, 1-4, 24-25, Working Draft Sequence, 3 unordered pieces. May 10, 2003.
Genbank Accession No. BAA09452.1; Mukohata et al.; pp. 1 (Feb. 10, 1999).
Genbank Accession No. DQ094781 (Jan. 15, 2008).
GenBank Accession No. U79717.1; Rattus norvegicus dopamine 02 receptor 1-4, 24-25 gene, promoter region and exon 1. Jan. 31, 1997.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from Bacillus subtilis DNA" Gene, 1984, vol. 32(1-2): pp. 11-20.
Glick et al."Factors affecting the expression of foreign proteins in Escherichia coli", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gonzalez, et al., "Cell-Based Assays and Instrumentation for Screening Ion-Channel Targets", DDT, 1999, vol. 4, No. 9, pp. 431439.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Goshen et al. "Dynamics of Retrieval Strategies for Remote Memories", Cell, 2011, col. 147: pp. 678-589.
Gottesman et al."Bacterial regulation: global regulatory networks," Ann. Rev. Genet. , 1984, vol. 18, pp. 415-441.
Gradinaru et al., "Optical Deconstruction of Parkinsonian neural circuitry," Science, Apr. 2009, 324(5925):354-359.
Gradinaru et al., "Targeting and readout strategies for fast optical neural control in vitro and in vivo", J Neuroscience, 2007, 27(52):14231-14238.
Gradinaru, et al. "ENpHR: a Natronomonas Halorhodopsin Enhanced for Optogenetic Applications", 2008, Brain Cell Biol., vol. 36 (1-4), pp. 129-139.
Gradinaru, et al., "Molecular and Cellular Approaches for Diversifying and Extending Optogenetics", Cell, 2010, vol. 141, No. 1, pp. 154-165.

Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for Streptomyces phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gunaydin et al., "Ultrafast optogenetic control", Nature Neuroscience, 2010, vol. 13, No. 3, pp. 387-392.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Haim, et al.; "Gene Therapy to the Nervous System"; Stem Cell and Gene-Based Therapy; Section 2, pp. 133-154 (2006).
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Han, et a.; "Virogenetic and optogenetic mechanisms to define potential therapeutic targets in psychiatric disorders"; Neuropharmacology; vol. 62, pp. 89-100 (2012).
Han, et al., "Millisecond-Timescale Optical Control of Neural Dynamics in the Nonhuman Primate Brain"; Neuron; vol. 62, pp. 191-198 (Apr. 30, 2009).
Han, et al., "Multiple-Color Optical Activation, Silencing, and Desynchronization of Neural Activity with Single-Spike Temporal Resolution", PLoS One, 2007, vol. 2, No. 3, pp. 1-12.
Han; et al., "Two-color, bi-directional optical voltage control of genetically-targeted neurons", CoSyne Abstract Presentation, Presented Feb. 24, 2007.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in Chlamydomonas rhodopsin", Biophys. J. , 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Heymann, et al.; "Expression of Bacteriorhodopsin in Sf9 and COS-1 Cells"; Journal of Bioenergetics and Biomembranes; vol. 29, No. 1, pp. 55-59 (1997).
Hikida et al., "Acetylcholine enhancement in the nucleus accumbens prevents addictive behaviors of cocaine and morphine", PNAS, May 2003, 100(10):6169-6173.
Hikida et al., "Increased sensitivity to cocaine by cholingergic cell ablation in nucleus accumbens," PNAS, Nov. 2001, 98(23):13351-13354.
Hildebrandt et al, "Bacteriorhodopsin expressed in Schizosaccharomyces pombe pumps protons through the plasma membrane," PNAS, 1993, vol. 90, pp. 3578-3582.

(56) References Cited

OTHER PUBLICATIONS

Hira et al., "Transcranial optogenetic stimulation for functional mapping of the motor cortex", J Neurosci Methods, 2009, vol. 179, pp. 258-263.
Hirase, et al. "Multiphoton stimulation of neurons", J Neurobiol, 2002, vol. 5I, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hofherr et al. "Selective Golgi export of Kir2.1 controls the stoichiometry of functional Kir2.x channel heteromers"Journal of Cell Science, 2005, vol. 118, p. 1935-1943.
Hosokawa, T. et al. "Imaging spatio-temporal patterns of long-term potentiation in mouse hippocampus." Philos. Trans. R. Soc. Lond. B., 2003, vol. 358, pp. 689-693.
Hustler; et al., "Acetylcholinesterase staining in human auditory and language cortices: regional variation of structural features", Cereb Cortex (Mar.-Apr. 1996), 6(2):260-70.
Hynynen, et al. "Clinical applications of focused ultrasound—The brain." Int. J. Hyperthermia, 2007, vol. 23, No. 2: pp. 193-202.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Ihara, et al.; "Evolution of the Archaeal Rhodopsins: Evolution Rate Changes by Gene Duplication and Functional Differentiation"; J. Mol. Biol.; vol. 285, pp. 163-174 (1999).
International Search Report for International Application No. PCT/US2009/053474, dated Oct. 8, 2009.
Isenberg et al.; "Cloning of a Putative Neuronal Nicotinic Aceylcholine Receptor Subunit"; Journal of Neurochemistry; vol. 52, No. 3, pp. 988-991 (1989).
Iyer et al., "Virally mediated optogenetic excitation and inhibition of pain in freely moving nontransgenic mice", Nat Biotechnol., 2014, 32(3):274-8.
Jekely, "Evolution of Phototaxis", 2009, Phil. Trans. R. Soc. B, vol. 364, pp. 2795-2808.
Jennings et al., "Distinct extended amygdala circuits for divergent motivational states," Nature, 2013, 496:224-228.
Ji et al., "Light-evoked Somatosensory Perception of Transgenic Rats that Express Channelrhodopsin-2 in Dorsal Root Ganglion Cells", PLoS One, 2012 7(3):e32699.
Jimenez S.A & Maren S. et al/ "Nuclear disconnection within the amygdala reveals a direct pathway to fear", Learning Memory, 2009, vol. 16: pp. 766-768.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene GAL4 and analysis of its dosage effects on the galactose/melibiose regulon," PNAS, 1982, vol. 79, pp. 6971-6975.
Kaiser; "Clinical research. Death prompts a review of gene therapy vector"; Science; 317(5838):580, 1 page (Aug. 3, 2007).
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After- Potentials and Repetitive Firing", J Neurophysiol., 1961, vol. 24, pp. 243-259.
Karra, et al. "Transfection Techniques for Neuronal Cells", The Journal of Neuroscience, 2010, vol. 30, No. 18, pp. 6171-6177.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Kay; "State-of-the-art gene-based therapies: the road ahead"; Nature Reviews Genetics; vol. 12, pp. 316-328 (May 2011).
Kelder et al., "Glycoconjugates in human and transgenic animal milk", Advances in Exp. Med. And Biol., 2001, vol. 501, pp. 269-278.
Kessler, et al.; "Gene delivery to skeletal muscle results in sustained expression and systemic delivery of a therapeutic protein"; Proc. Natl. Acad. Sci. USA; vol. 93, pp. 14082-14087 (Nov. 1996).
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khosravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Diverging neural pathways assemble a behavioural state from separable features in anxiety" Nature, 2013, 496(7444):219-23.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kim et al., "PDZ domain proteins of synapses", Nature Reviews Neuroscience, 2004, vol. 5, No. 10, pp. 771-781.
Kingston et al. "Transfection and Expression of Cloned DNA," Supplement 31, Current Protocols in Immunology, 1999, 10.13.1-1 0.13.9.
Kingston et al. "Transfection of DNA into Eukaryotic Cells," Supplement 63, Current Protocols in Molecular Biology, 1996, 9.1.1-9.1.11, 11 pages.
Kinoshita, et al., "Optogenetically Induced Supression of Neural Activity in the Macaque Motor Cortex", Poster Sessions Somatomotor System, Others, Society for Neuroscience Meeting, 2010, pp. 141-154.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitabatake et al., "Impairment of reward-related learning by cholinergic cell ablationn in the striatum", PNAS, Jun. 2003, 100(13):7965-7970.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Knopfel, et al. "Optical Probing of Neuronal Circuit Dynamics: Gentically Encoded Versus Classical Fluorescent Sensors", 2006, Trends Neurosci, vol. 29, No. 3, pp. 160-166.
Knopfel, et al.; "A comprehensive concept of optogenetics"; Progress in Brain Research; vol. 196, pp. 1-28 (2012).
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kokel et al., "Photochemical activation of TRPA1 channels in neurons and animals", Nat Chem Biol, 2013, 9(4):257-263.
Kuhlman et al. (2008) "High-Resolution Labeling and Functional Manipulation of Specific Neuron Types in Mouse Brain by Cre-Activated Viral Gene Expression" PLoS One, e2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.

(56) References Cited

OTHER PUBLICATIONS

Lalumiere, R., "A new technique for controlling the brain: optogenetics and its potential for use in research and the clinic", Brain Stimulation, 2011, vol. 4, pp. 1-6.
Lammel et al., "Input-specific control of reward and aversion in the ventral tegmental area", Nature, 2012, 491(7423): 212-217.
Landy, A. "Mechanistic and structural complexity in the site-specific recombination pathways of Int and FLP", Current Opinion in Genetics and Development, 1993, vol. 3, pp. 699-707.
Lanyi et al. "The primary structure of a Halorhodopsin from Natronobacterium Pharaonis" Journal of Biological Chemistry, 1990, vol. 265, No. 3, p. 1253-1260.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gene Therapy Can Prevent Neuron Death Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS 2005, vol. 102, No. 49, p. 17816-17821.
Li et al., "Surface Expression of Kv1 Channels is Governed by a C-Terminal Motif", J. Bioi. Chem. (2000), 275(16):11597-11602.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992,vol. 9, pp. 861-871.
Lin, "A user's guide to channelrhodopsin variants: features, limitations and future developments", Exp Physiol, 2010, vol. 96, No. 1, pp. 19-25.
Liske et al., "Optical inhibition of motor nerve and muscle activity in vivo", Muscle Nerve, 2013, 47(6):916-21.
Liu et al., "Optogenetics 3.0", Cell, Apr. 2010, 141(1):22-24.
Llewellyn et al., "Orderly recruitment of motor units under optical control in vivo", Nat Med., 2010, 16(10):1161-5.
Loetterle, et al., "Cerebellar Stimulation: Pacing the Brain", American Journal of Nursing, 1975, vol. 75, No. 6, pp. 958-960.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Malin et al., "Involvement of the rostral anterior cingulate cortex in consolidation of inhibitory avoidance memory: Interaction with the basolateral amygdala", Neurobiol Learn Mem., Feb. 2007, 87(2):295-302.
Mancuso et al., "Optogenetic probing of functional brain circuitry", Experimental Physiology, 2010, vol. 96.1, pp. 26-33.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mann; "Synapses"; The Nervous System in Action; Chapter 13, http://michaeldmann.net/mann13.html (downloaded Apr. 2014).
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Mattis et al., "Principles for applying optogenetic tools derived from direct comparative analysis of microbial opsins", Nat Methods, 2011, 9(2):159-72.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
Mayford et al., "Control of memory formation through regulated expression of CaMKII transgene", Science, Dec. 1996, 274(5293):1678-1683.
McAllister, "Cellular and Molecular Mechanisms of Dendrite Growth", 2000, Cereb Cortex, vol. 10, No. 10, pp. 963-973.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Milella et al. "Opposite roles of dopamine and orexin in quinpirole-induced excessive drinking: a rat model of psychotic polydipsia" Psychopharmacology, 2010, 211:355-366.
Monje et al., "Irradiation Induces Neural Precursor-Cell Dysfunction", Natural Medicine, 2002, vol. 8, No. 9, pp. 955-962.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Mortensen et al. "Selection of Transfected Mammalian Cells," Supplement 86, Current Protocols in Molecular Biology, 1997, 9.5.1-09.5.19.
Mourot et al., "Rapid Optical Control of Nociception with an Ion Channel Photoswitch", Nat Methods, 2012, 9(4):396-402.
Mueller, et al.; "Clinical Gene Therapy Using Recombinant Adeno-Associated Virus Vectors"; Gene Therapy; vol. 15, pp. 858-863 (2008).
Mullins et al., "Expression of the DBA/2J Ren-2 gene in the adrenal gland of transgenic mice", EMBO, 1989, vol. 8, pp. 4065-4072.
Mullins et al., "Fulminant hypertension in transgenic rats harbouring the mouse Ren-2 gene", Nature, 1990, vol. 344, pp. 541-544.
Nacher, et al. "NMDA receptor antagonist treatment increases the production of new neurons in the aged rat hippocampus", Neurobiology of Aging, 2003,vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Natochin, et al. "Probing rhodopsin-transducin interaction using *Drosophila* Rh1-bovine rhodopsin chimeras," Vision Res., 2006, vol. 46, No. 27: pp. 4575-4581.

(56) References Cited

OTHER PUBLICATIONS

Nieh et al., "Optogenetic dissection of neural circuits underlying emotional valence and motivated behaviors", Brain Research, E-pub 2012, 1511:73-92.
Nirenberg, et al. "The Light Response of Retinal Ganglion Cells is Truncated by a Displaced Amacrine Circuit", Neuron, 1997, vol. 18: pp. 637-650.
No Authors Listed; "Two bright new faces in gene therapy," Nature Biotechnology, 1996, vol. 14: p. 556.
Nonet, "Visualization of synaptic specializations in live C. elegans with synaptic vesicle protein-GFP fusions", J. Neurosci. Methods, 1999, 89:33-40.
Nunes-Duby, et al. "Similarities and differences among 105 members of the Int family of site-specific recombinases", Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Packer, et al.; "Targeting Neurons and Photons for Optogenetics"; Nature Neuroscience; vol. 16, No. 7, pp. 805-815 (Jul. 2013).
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Palmer et al., "The Adult Rat Hippocampus Contains Primordial Neural Stem Cells", Molecular and Cellular Neuroscience, 1997, vol. 8, pp. 389-404.
Pan et al. "Functional Expression of a Directly Light-Gated Membrane Channel in Mammalian Retinal Neurons: A Potential Strategy for Restoring Light Sensitivity to the Retina After Photoreceptor Degeneration"; Investigative Opthalmology & Visual Science, 2005, 46 E-Abstract 4631. Abstract only.
Panda, et al. "Illumination of the Melanopsin Signaling Pathway", Science, 2005, vol. 307: pp. 600-604.
Pandya, et al.; "Where in the Brain Is Depression?"; Curr. Psychiatry Rep.; vol. 14, pp. 634-642 (2012).
Pape, et al., "Plastic Synaptic Networks of the Amygdala for the Acquisition, Expression, and Extinction of Conditioned Fear", 2010, Physiol Rev, vol. 90, pp. 419-463.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1-9.1 1 .1 8.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Peterlin, et al. "Optical probing of neuronal circuits with calcium indicators," PNAS, 2000, vol. 97, No. 7: pp. 3619-3624.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.

Pinkham et al., "Neural bases for impaired social cognition in schizophrenia and autism spectrum disorders", Schizophrenia Research, 2008, vol. 99, pp. 164-175.
Potter, "Transfection by Electroporation." Supplement 62, Current Protocols in Molecular Biology, 1996, 9.3.1-9.3.6.
Pouille, et al. "Routing of spike series by dynamic circuits in the hippocampus", Nature, 2004, vol. 429: pp. 717-723.
Qiu et al. "Induction of photosensitivity by heterologous expression of melanopsin", Nature, 2005, vol. 433: pp. 745-749.
Ramalho, et al.; "Mouse genetic corneal disease resulting from transgenic insertional mutagenesis"; Br. J. Ophthalmol.; vol. 88, No. 3, pp. 428-432 (Mar. 2004).
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Raper, et al.; "Fatal systemic inflammatory response syndrome in a ornithine transcarbamylase deficient patient following adenoviral gene transfer." Mol. Genet. Metab.; vol. 80, No. 1-2, pp. 148-158 (Sep.-Oct. 2003).
Rathnasingham et al., "Characterization of implantable microfabricated fluid delivery devices," IEEE Transactions on Biomedical Engineering, 2004, vol. 51, No. 1: pp. 138-145.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Ristevski; "Making Better Transgenic Models: Conditional, Temporal, and Spatial Approaches"; Molecular Biotechnology; vol. 29, No. 2, pp. 153-163 (Feb. 2005).
Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Sajdyk, et al., "Excitatory Amino Acid Receptors in the Basolateral Amygdala Regulate Anxiety Responses in the Social Interaction Test", Brain Research, 1997, vol. 764, pp. 262-264.
Salzman, et al. "Cortical microstimulation influences perceptual judgements of motion direction", Nature, 1990, vol. 346, pp. 174-177.
Samuelson; "Post-traumatic stress disorder and declarative memory functioning: a review"; Dialogues in Clinical Neuroscience; vol. 13, No. 3, pp. 346-351 (2011).
Santana et al., "Can Zebrafish Be Used as Animal Model to Study Alzheimer's Disease?" Am. J. Neurodegener. Dis. (2012), 1(1):32-48.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.

(56) References Cited

OTHER PUBLICATIONS

Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depresion," Neuropsychopharmacology, 2008,vol. 33, pp. 368-377.
Schroll et al., "Light-induced activation of distinct modulatory neurons triggers appetitive or aversive learning in *Drosophila* larvae", Current Biology, Sep. 2006, 16(17):1741-1747.
Sclimenti, et al. "Directed evolution of a recombinase for improved genomic integration at a native human sequence," Nucleic Acids Research, 2001, vol. 29, No. 24: pp. 5044-5051.
Sheikh et al., "Neurodegenerative Diseases: Multifactorial Conformational Diseases and Their Therapeutic Interventions", Journal of Neurodegenerative Diseases (2013), Article ID 563481:1-8.
Shepherd, et al. "Circuit Analysis of Experience-Dependent Plasticity in the Developing Rat Barrel Cortex", Neuron, 2003, vol. 38: pp. 277-289.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Sigmund; "Viewpoint: Are Studies in Genetically Altered Mice Out of Control?"; Arterioscler Thromb Vasc Biol.; vol. 20, No, 6, pp. 1425-1429 (Jun. 2000).
Silver, et al. "Amino terminus of the yeast GAL4 gene product is sufficient for nuclear localization" PNAS, 1984, vol. 81, No. 19: pp. 5951-5955.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Sineshchekov et al.; "Intramolecular Proton Transfer in Channelrhodopsins"; Biophysical Journal; vol. 104, No. 4, pp. 807-807 (Feb. 2013).
Sineshchekov et al., "Two Rhodopsins Mediate Phototaxis to Low and High Intensity Light in Chlamydomas Reinhardtil", PNAS, 2002, vol. 99, No. 13, pp. 8689-8694.
Singer et al. "Elevated Intrasynaptic Dopamine Release in Tourette's Syndrome Measured by PET," American Journal of Psychiatry, 2002, vol. 159: pp. 1329-1336.
Singer; "Light Switch for Bladder Control"; Technology Review; pp. 1-2 (Sep. 14, 2009).
Skolnick, et al.; "From genes to protein structure and function: novel applications of computational approaches in the genomic era"; Trends Biotechnol; vol. 18, No. 1, pp. 34-39 (Jan. 2000).
Slamovits et al., "A bacterial proteorhodopsin proton pump in marie eukaryotes", Nature Comm, 2011, 2:183.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Sohal et al., "Parvalbumin neurons and gamma rhythms enhance cortical circuit performance", Nature, 2009, vol. 459, No. 7247, pp. 698-702.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Song, "Genes responsible for native depolarization-activated K+ currents in neurons," Neuroscience Research, 2002, vol. 42, pp. 7-14.
Soofiyani, et al.; "Gene Therapy, Early Promises, Subsequent Problems, and Recent Breakthroughs"; Advanced Pharmaceutical Bulletin; vol. 3, No. 2, pp. 249-255 (2013).
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Stonehouse, et al.; "Caffeine Regulates Neuronal Expression of the Dopamine 2 Receptor Gene"; Molecular Pharmacology; vol. 64, No. 6, pp. 1463-1473 (2003).
Suzuki et al., "Stable Transgene Expression from HSV Amplicon Vectors in the Brain: Potential Involvement of Immunoregulatory Signals", Molecular Therapy (2008), 16(10):1727-1736.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.
Swiss-Prot_Q2QCJ4, Opsin 1, Oct. 31, 2006, URL: http://www.ncbi.nlm.nig.gov/protein/Q2QCJ4.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Takahashi, et al., "Induction of Pluripotent Stem Cells from Mouse Embryonic and Adult Fibroblast Cultures by Defined Factors", 2006, Cell, vol. 126, pp. 663-676.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Tamai, "Progress in Pathogenesis and Therapeutic Research in Retinitis Pigmentosa and Age Related Macular Degeneration", Nippon Ganka Gakkai Zasshi, Dec. 2004, 108(12):750-769.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Taurog et al., "HLA-B27 in inbred and non-inbred transgenic mice", J. Immunol., 1988, vol. 141, pp. 4020-4023.
Thomas et al., "Progress and Problems with the Use of Viral Vectors for Gene", Nat. Rev. Genet. (2003), 4(5):346-358.
Tønnesen, et al., "Optogenetic Control of Epileptiform Activity", PNAS, 2009, vol. 106, No. 29, pp. 12162-12167.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Towne et al., "Efficient transduction of non-human primate motor neurons after intramuscular delivery of recombinant AAV serotype 6", Gene Ther., 2010, 17(1):141-6.
Towne et al., "Optogenetic control of targeted peripheral axons in freely moving animals", PLoS One, 2013, 8(8):e72691.
Towne et al., "Recombinant adeno-associated virus serotype 6 (rAAV2/6)-mediated gene transfer to nociceptive neurons through different routes of delivery", Mol Pain, 2009, 5:52.
Tsai, et al., "Phasic Firing in Dopaminergic Neurons in Sufficient for Behavioral Conditioning", Science, 2009, vol. 324, pp. 1080-1084.
Tsau et al. "Distributed Aspects of the Response to Siphon Touch in Aplysia: Spread of Stimulus Information and Cross-Correlation Analysis," The Journal of Neuroscience, 1994, vol. 14, No. 7, pp. 4167-4184.
Tye et. al., "Amygdala circuitry mediating reversible and bidirectional control of anxiety", Nature, 2011, vol. 471(7338): pp. 358-362.
Tye et. al., Supplementary Materials: "Amygdala circuitry mediating reversible and bidirectional control of anxiety,", Nature, 2011, vol. 471(7338): pp. 358-362.
Tye, et al. "Optogenetic investigation of neural circuits underlyding brain disease in animal models," Nature Reviews Neuroscience (Mar. 2012), 13(4):251-266.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before

(56) References Cited

OTHER PUBLICATIONS and after Treatment with the selective serotonin reuptake inhibitor citalopram," Prog Neuropsychopharmacol Biol Psychiatry, 2000, vol. 24, No. 3: pp. 419-438.

Vanin, et al. "Development of high-titer retroviral producer cell lines by using Cre-mediated recombination," Journal of Virology, 1997, vol. 71, No. 10: pp. 7820-7826.

Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9.I9.I-19.39.

Wall, "Transgenic livestock: Progress and prospects for the future", Theriogenology, 1996, vol. 45, pp. 57-68.

Wang, et al. "Direct-current Nanogenerator Driven by Ultrasonic Waves," Science, 2007, vol. 316, pp. 102-105.

Wang, et al., "High-speed mapping of synaptic connectivity using photostimulation in Channelrhodopsin-2 transgenic mice", PNAS, 2007, vol. 104, No. 19, pp. 8143-8148.

Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.

Wang, et al., "Mrgprd-Expressing Polymodal Nociceptive Neurons Innervate Most Known Classes of Substantia Gelatinosa Neurons", J Neurosci, 2009, 29(42):13202-13209.

Wang, et al.; "Laser-evoked synaptic transmission in cultured hippocampal neurons expressing channelrhodopsin-2 delivered by adeno-associated virus"; Journal of Neuroscience Methods; vol. 183, pp. 165-175 (2009).

Ward, et al. "Construction and characterisation of a series of multi-copy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.

Wells et al. "Application of Infrared light for in vivo neural stimulation," Journal of Biomedical Optics, 2005, vol. 10(6), pp. 064003-1-064003-12.

Williams et al., "From optogenetic technologies to neuromodulation therapies", Sci Transl Med., 2013, 5(177):177.

Witten et. al., "Cholinergic Interneurons Control Local Circuit Activity and Cocaine Conditioning", Science, 2010, vol. 330, No. 6011: pp. 1677-1681.

Witten et. al., Supporting Online Material for: "Cholinergic Interneurons Control Local Circuit Activity and Cocaine Conditioning", Science, 2010, vol. 330: 17 pages.

Written opinion of PCT Application No. PCT/US2011/059383 (dated May 9, 2012).

Xiong et al., "Interregional connectivity to primary motor cortex revealed using MRI resting state images", Hum Brain Mapp, 1999, 8(2-3):151-156.

Yamazoe, et al. "Efficient generation of dopaminergic neurons from mouse embryonic stem cells enclosed in hollow fibers", Biomaterials, 2006, vol. 27, pp. 4871-4880.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Yizhar et al., "Optogenetics in neural systems", Neuron Primer, vol. 71, No. 1, pp. 9-34 (Jul. 14, 2011).

Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang "Multimodal fast optical interrogation of neural circuitry," Nature, 2007, vol. 446, pp. 633-641.

Zhang, et al. "Channelrhodopsin-2 and optical control of excitable cells," Nature Methods,2006, vol. 3, No. 10, pp. 785-792.

Zhang, et al. "Red-Shifted Optogenetic Excitation: a Tool for Fast Neural Control Derived from *Volvox carteri*", Nature Neurosciences, 2008,vol. 11, No. 6, pp. 631-633.

Zhang, et al., "The Microbial Opsin Family of Optogenetic Tools", Cell, 2011, vol. 147, No. 7, pp. 1146-1457.

Zhang, et al.; "Optogenetic interrogation of neural circuits: Technology for probing mammalian brain structures"; Nature Protocols; vol. 5, No. 3, pp. 439-456 (Feb. 18, 2010).

Zhao, et al., "Improved Expression of Halorhodopsin for Light-Induced Silencing of Neuronal Activity", Brain Cell Biology, 2008, vol. 36 (1-4), pp. 141-154.

Zrenner, E., "Will Retinal Implants Restore Vision?" Science, 2002, vol. 295, No. 5557, pp. 1022-1025.

Zufferey, et al. "Self-Inactivating Lentivirus Vector for Safe and Efficient In Vivo Gene Delivery", Journal of Virology, 1998, vol. 72, No. 12, pp. 9873-9880.

Definition of Implant; Merriam-Webster Dictionary; retrieved Nov. 7, 2016 (http://www.merriam-webster.com/dictionary/implant).

Ferenczi, et al.; "Optogenetic approaches addressing extracellular modulation of neural excitability"; Scientific Reports; vol. 6, 20 pages (Apr. 5, 2016).

Li, et al.; "A Method for Activiation of Endogenous Acid-sensing Ion Channel 1a (ASIC1a) in the Nervous System with High Spatial and Temporal Precision"; The Journal of Biological Chemistry; vol. 289, No. 22, pp. 15441-15448 (May 30, 2014).

Shimizu, et al.; "NMDA Receptor-Dependent Synaptic Reinforcement as a Crucial Process for Memory Consolidation"; Science; vol. 290, pp. 1170-1174 (Nov. 10, 2000).

Zeng, et al.; "Activation of acid-sensing ion channels by localized proton transient reveals their role in proton signaling"; Scientific Reports; vol. 5, 14 pages (Sep. 15, 2015).

Zeng, et al.; "Proton production, regulation and pathophysiological roles in the mammalian brain"; Neuroscience Bulletin; vol. 28, No. 1, pp. 1-13 (Feb. 1, 2012).

Johnson, et al.; "Differential Biodistribution of Adenoviral Vector In Vivo as Monitored by Bioluminescence Imaging and Quantitative Polymerase Chain Reaction"; Human Gene Therapy; vol. 17, pp. 1262-1269 (Dec. 2006).

Schester, et al.; "Biodistribution of adeno-associated virus serotype 9 (AAV9) vector after intrathecal and intravenous delivery in mouse"; Frontiers in Neuroanatomy; vol. 8, Article 42, pp. 1-41 (Jun. 10, 2014).

Abbott, et al.; "Photostimulation of Retrotrapezoid Nucleus Phox2b-Expressing Neurons In Vivo Produces Long-Lasting Activation of Breathing in Rats"; The Journal of Neuroscience; vol. 29, No. 18, pp. 5806-5819 (May 6, 2009).

Alilain, et al.; "Light-Induced Rescue of Breathing after Spinal Cord Injury"; The Journal of Neuroscience; vol. 28, No. 46, pp. 11862-11870 (Nov. 12, 2008).

(56) References Cited

OTHER PUBLICATIONS

Cardin, et al.; "Targeted optogenetic stimulation and recording of neurons in vivo using cell-type-specific expression of Channelrhodopsin-2"; Nature Protocols; vol. 5, No. 2, pp. 247-254 (2010).
Caro, et al.; "Engineering of an Artificial Light-Modulated Potassium Channel"; PLoS One; vol. 7, Issue 8, e43766 (Aug. 2012).
Coleman, et al.; "Assessing Anxiety in Nonhuman Primates"; Ilar Journal; vol. 55, No. 2, pp. 333-346 (2014).
Hagglund, et al.; "Activation of groups of excitatory neurons in the mammalian spinal cord or hindbrain evokes locomotion"; Nature Neuroscience; vol. 13, No. 2, 8 pages (Feb. 2010).
Kleinlogel, et al.; "A gene-fusion strategy for stoichiometric and co-localized expression of light-gated membrane proteins"; Nature Methods; vol. 8, No. 12, pp. 1083-1091 (Dec. 2011).
Kravitz, et al.; "Regulation of parkinsonian motor behaviours by optogenetic control of basal ganglia circuitry"; Nature; vol. 466, No. 622, 8 pages (Jul. 29, 2010).
Luo, et al.; "Synthetic DNA delivery systems"; Nature Biotechnology; vol. 18, pp. 33-37 (Jan. 2000).
Maestripieri, et al.; "A modest proposal: displacement activities as an indicator of emotions in primates"; Anim. Behav.; vol. 44, pp. 967-979 (1992).
Nelson, et al.; "Non-Human Primates: Model Animals for Developmental Psychopathology"; Neuropsychopharmacology; vol. 34, No. 1, pp. 90-105 (Jan. 2009).
Tomita, et al.; "Visual Properties of Transgenic Rats Harboring the Channelrhodopsin-2 Gene Regulated by the Thy-1.2 Promoter"; PLoS One; vol. 4, No. 11, 13 pages (Nov. 2009).
Uniprot Accession No. P02945, integrated into the database on Jul. 21, 1986.
Definition of integral. Merriam-Webster Dictionary, retrieved on Mar. 20, 2017; Retrieved from the internet: <http://www.merriam-webster.com/dictionary/integral>.
Gritton, et al.; "Optogenetically-evoked cortical cholinergic transients in mice expressing channelrhodopsin-2 (ChR2) in cholinergic neurons"; Society for Neuroscience Abstract Viewer and Itinery Planner & 40th Annual Meeting of the Society-for-Neuroscience; vol. 40, 2 pages (2010).
Sofuoglu, et al.; "Cholinergic Functioning in Stimulant Addiction: Implications for Medications Development"; CNS Drugs; vol. 23, No. 11, pp. 939-952 (Nov. 1, 2009).
Witten, et al.; "Cholinergic interneurons of the nucleus accumbens control local circuit activity and reward behavior"; Society for Neuroscience Abstract Viewer and Itinerary Planner & 40th Annual Meeting of the Society-for-Neuroscience; vol. 40, 2 pages (2010).
Lin, et al.; "Study of the Circuitry of Nucleus Accumbens and its Effect on Addiction by Optogenetic Methods: 964"; Neurosurgery; vol. 67, No. 2, p. 557 (Aug. 2010).
Tsuchida; "Nervous Control of Micturition"; The Japanese Journal of Urology; vol. 80, No. 9, pp. 1257-1277 (1989).
Azizgolshani, et al.; "Reconstituted plant viral capsids can release genes to mammalian cells"; Virology; vol. 441, No. 1, pp. 12-17 (2013).
Racaniello; "How many viruses on Earth?"; Virology Blog; 6 pages; http://www.virology.ws/2013/09/06/how-many-viruses-on-earth/ (Sep. 6, 2013).
Bibel, et al.; "Differentiation of mouse embryonic stem cells into a defined neuronal lineage"; Nature Neuroscience; vol. 7, No. 9, pp. 1033-1009 (Sep. 2004).
Daniel, et al.; "Stress Modulation of Opposing Circuits in the Bed Nucleus of the Stria Terminalis"; Neuropsychopharmacology Reviews; vol. 41, pp. 103-125 (2016).
Hammack, et al.; "The response of neurons in the bed nucleus of the stria terminalis to serotonin Implications for anxiety"; Progress in Neuro-Psychopharmacology & Biological Psychiatry; vol. 33, pp. 1309-1320 (2009).
Knopfel, et al.; "Remote control of cells"; Nature Nanotechnology; vol. 5, pp. 560-561 (Aug. 2010).

Steimer; "The biology of fear- and anxiety-related behaviors"; Dialogues in Clinical Neuroscience; vol. 4, No. 3, pp. 231-249 (Sep. 2002).
Stuber; "Dissecting the neural circuitry of addiction and psychiatric disease with optogenetics"; Neuropsychopharmacology; vol. 35, No. 1, pp. 341-342 (2010).
Gerits, et al.; "Optogenetically Induced Behavioral and Functional Network Changes in Primates"; Current Biology; vol. 22, pp. 1722-1726 (Sep. 25, 2012).
Han, et al.; "Optogenetics in the nonhuman primate"; Prog. Brain Res.; vol. 196, pp. 215-233 (2012).
Kugler, et al.; "Neuron-Specific Expression of Therapeutic Proteins: Evaluation of Different Cellular Promoters in Recombinant Adenoviral Vectors"; Molecular and Cellular Neuroscience; vol. 17, pp. 78-96 (2001).
Masaki, et al.; "$\beta$2-Adrenergic Receptor Regulation of the Cardiac L-Type Ca2+ Channel Coexpressed in a Fibroblast Cell Line"; Receptor; vol. 5, pp. 219-231 (1996).
Smith, et al.; "Proton binding sites involved in the activation of acid-sensing ion channel ASIC2a"; Neuroscience Letters; vol. 426, pp. 12-17 (2007).
Ahmad, et al. "Heterplogous expression of bovine rhodopsin in *Drosophila* photoreceptor cells" Invest Ophthalmol Vis Sci. 2006, 3722-3728.
Clare "Targeting Ion Channels for Drug Discovery" Discov Med. 2010 vol. 9 No. 46 pp. 1-6.
Clare "Functional Expression of Ion Channels in Mammalian Systems" Protein Science Encyclopedia A.R. Fersht (Ed.) 2008 pp. 79-109.
Reeves et al., "Structure and function in rhodosin: A tetracycline-inducible system in stable mammalian cell lines for high-level expression of opsin mutants" PNAS, 2002 vol. 99 No. 21 pp. 13413-13418.
Friedman, et al.; "VTA Dopamine Neuron Bursting is Altered in an Animal Model of Depression and Corrected by Desipramine"; J. Mol. Neurosci.; vol. 34, pp. 201-209 (2008).
Hackmann, et al.; "Static and time-resolved step-scan Fourier transform infrared investigations of the photoreaction of halorhodopsin from Natronobacterium pharaonis: consequences for models of the anion translocation mechanism"; Biophysical Journal; vol. 81, pp. 394-406 (Jul. 2001).
Weiss, et al.; "Galanin: A Significant Role in Depression?"; Annals New York Academy of Sciences; vol. 863, No. 1, pp. 364-382 (1998).
Winter, et al.; "Lesions of dopaminergic neurons in the substantia nigra pars compacta and in the ventral tegmental area enhance depressive-like behavior in rats"; Behavioural Brain Research; vol. 184, pp. 133-141 (2007).
Boyden, et al.; "A history of optogenetics: the development of tools for controlling brain circuits with light"; F1000 Biology Reports; vol. 3, No. 11, 12 pages (May 3, 2011).
Knox, et al.; "Heterologous Expression of *Limulus* Rhodopsin"; The Journal of Biological Chemistry; vol. 278, No. 42, pp. 40493-40502 (Oct. 17, 2003).
Lin, et al.; "Characterization of Engineered Channelrhodopsin Variants with Improved Properties and Kinetics"; Biophysical Journal; vol. 96, No. 5, pp. 1803-1814 (Mar. 2009).
Duvarci, et al., "The bed Nucleus of the Stria Terminalis Mediates inter-individual variations in anxiety and fear", J. Neurosci., 29(33) 10357-10361 (2009).
Matsuda "Bed nucleus of stria terminalis (BNST)" Benshi Seishin Igaku (Molecular Psychiatric Medicine), 2009, vol. 9 No. 3, p. 46-49.
Neuropsychopharmacology, 2011, vol. 36 No. Suppl.1, p. S110 (Abstract No. 67) (Newly cited document).
Neuropsychopharmacology, 2012, vol. 38 No. Suppl.1, p. S48 (Abstract No. 37.2).
Walker et al. "Selective Participation of the Bed Nucleus of the Stria Terminalis and CRF in Sustained Anxiety-like versus Phasic Fear-Like Responses," Prog Neuropsychopharmacol Bio Psychiatry, 13: 33(8) 1291-1308 (2009).

(56) References Cited

OTHER PUBLICATIONS

Belzung et al., "Optogenetics to study the circuits of fear- and depresssion-like behaviors: A critical analysis," Pharmacology, Biochemistry and Behavior, 2014, 122: 144-157.

Bernstein & Boyden "Optogenetic tools for analyzing the neural circuits of behavior," Trends Cogn Sci., 2011 15(12): 592-600.

* cited by examiner amino acid sequence of Archaerhodopsin-3
*Halorubrum sodomense*
GenBank P96787
258 aa MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAAD (SEQ ID NO:1)

amino acid sequence of eArch3.0-EYFP:

MDPIALQAGYDLLGDGRPETLWLGIGTLLMLIGTFYFLVRGWGVTDKDAREYYAVTIL
VPGIASAAYLSMFFGIGLTEVTVGGEMLDIYYARYADWLFTTPLLLLDLALLAKVDRV
TIGTLVGVDALMIVTGLIGALSHTAIARYSWWLFSTICMIVVLYFLATSLRSAAKERGPE
VASTFNTLTALVLVLWTAYPILWIIGTEGAGVVGLGIETLLFMVLDVTAKVGFGFILLR
SRAILGDTEAPEPSAGADVSAADRPVVAAAAKSRITSEGEYIPLDQIDINVVSKGEELF
TGVVPILVELDGDVNGHKFSVSGEGEGDATYGKLTLKFICTTGKLPVPWPTLVTTFGY
GLQCFARYPDHMKQHDFFKSAMPEGYVQERTIFFKDDGNYKTRAEVKFEGDTLVNRI
ELKGIDFKEDGNILGHKLEYNYNSHNVYIMADKQKNGIKVNFKIRHNIEDGSVQLADH
YQQNTPIGDGPVLLPDNHYLSYQSALSKDPNEKRDHMVLLEFVTAAGITLGMDELYKF
CYENEV (SEQ ID NO:2).

RPVVAAAA = linker
KSRITSEGEYIPLDQIDINV = inward rectifier potassium channel (GenBank AAA92568)
membrane trafficking signal
FCYENEV: ER export signal
Double-underlined sequence = yellow fluorescent protein

Amino acid sequence of ArchT
*Halorubrum sp.TP009*
GenBank AEB26832
248 aa

MDPIALQAGYDLLGDGRPETLWLGIGTLLMLIGTFYFIVKGWGVTDKEAREYYSITILVP
GIASAAYLSMFFGIGLTEVTVAGEVLDIYYARYADWLFTTPLLLLDLALLAKVDRVSIGT
LVGVDALMIVTGLIGALSHTPLARYSWWLFSTICMIVVLYFLATSLRAAAKERGPEVAST
FNTLTALVLVLWTAYPILWIIGTEGAGVVGLGIETLLFMVLDVTAKVGFGFILLRSRAIL
GDTEAPEP (SEQ ID NO:3)

FIG. 5A amino acid sequence of GtR3
*Guillardia theta*
GenBank EKX44791.1
223 aa

ASSFGKALLEFVFIVFACITLLLGINAAKSKAASRVLFPATFVTGIASIAYFSMASGGGWVI
APDCRQLFVARYLDWLITTPLLLIDLGLVAGVSRWDIMALCLSDVLMIATGAFGSLTVG
NVKWVWWFFGMCWFLHIIFALGKSWAEAAKAKGGDSASVYSKIAGITVITWFCYPVV
WVFAEGFGNFSVTFEVLIYGVLDVISKAVFGLILMSGAATGYESI (SEQ ID NO:4).

Amino acid sequence of rhodopsin type II proton pump
*Oxyrrhis marina*
GenBank ADY17806

```
maplaqdwty aewsavynal sfgiagmgsa tiffwlqlpn vtknyrtalt itgivtliat
yhyfrifnsw vaafnvglgv ngayevtvsg tpfndayryv dwlltvplll velilvmklp
aketvclawt lgiasavmva lgypgeiqdd lsvrwfwwac amvpfvyvvg tlvvglgaat
akqpegvvdl vsaaryltvv swltypfvyi vkniglagst atmyeqigys aadvtakavf
gvliwaiana ksrleeegkl ra (SEQ ID NO:5)
```

FIG. 5B

**Amino acid sequence of *L. maculans* rhodopsin (Mac)**
*Leptosphaeria maculans*
GenBank AAG01180 mivdqfeevl mktsqlfplp tatqsaqpth vapvptvlpd tpiyetvgds gsktlwvvfv
lmliasaaft alswkipvnr rlyhvittii tltaalsyfa matghgvaln kivirtqhdh
vpdtyetvyr qvyyaryidw aittplllld lgllagmsga hifmaivadl imvltglfaa
fgsegtpqkw gwytiaciay ifvvwhlvln gganarvkge klrsffvaig aytlilwtay
pivwgladga rkigvdgeii ayavldvlak gvfgawllvt hanlresdve lngfwangln
regairiged dga (SEQ ID NO:6)

Amino acid sequence of Mac 3.0

MIVDQFEEVLMKTSQLFPLPTATQSAQPTHVAPVPTVLPDTPIYETVGDSGSKTLWVVFVLMLIA
SAAFTALSWKIPVNRRLYHVITTIITLTAALSYFAMATGHGVALNKIVIRTQHDHVPDTYETVYR
QVYYARYIDWAITTPLLLLDLGLLAGMSGAHIFMAIVADLIMVLTGLFAAFGSEGTPQKWGWYTI
ACIAYIFVVWHLVLNGGANARVKGEKLRSFFVAIGAYTLILWTAYPIVWGLADGARKIGVDGEII
AYAVLDVLAKGVFGAWLLVTHANLRESDVELNGFWANGLNREGAIRIGEDDGARPVVAVSKAAA**K
SRITSEGEYIPLDQIDINV**VSKGEELFTGVVPILVELDGDVNGHKFSVSGEGEGDATYGKLTLKF
ICTTGKLPVPWPTLVTTFGYGLQCFARYPDHMKQHDFFKSAMPEGYVQERTIFFKDDGNYKTRAE
VKFEGDTLVNRIELKGIDFKEDGNILGHKLEYNYNSHNVYIMADKQKNGIKVNFKIRHNIEDGSV
QLADHYQQNTPIGDGPVLLPDNHYLSYQSALSKDPNEKRDHMVLLEFVTAAGITLGMDELYK**FCY
ENEV**  (SEQ ID NO:7)

FIG. 5C

Amino acid sequence of ChR2:
*Chlamydomonas rheinhardtii*

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTCPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:8).

amino acid sequence of a ChR2 SFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSDIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:9).

Underlined and bolded: C128S amino acid sequence of ChR2 SSFO:

MDYGGALSAVGRELLFVTNPVVVNGSVLVPEDQCYCAGWIESRGTNGAQTASNVLQW
LAAGFSILLLMFYAYQTWKSTCGWEEIYVCAIEMVKVILEFFFEFKNPSMLYLATGHRVQ
WLRYAEWLLTSPVILIHLSNLTGLSNDYSRRTMGLLVSAIGTIVWGATSAMATGYVKVIF
FCLGLCYGANTFFHAAKAYIEGYHTVPKGRCRQVVTGMAWLFFVSWGMFPILFILGPEG
FGVLSVYGSTVGHTIIDLMSKNCWGLLGHYLRVLIHEHILIHGDIRKTTKLNIGGTEIEVET
LVEDEAEAGAVP (SEQ ID NO:10).

Underlined and bolded: C128S and D156A amino acid sequence of C1V1:

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYAEWLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED
(SEQ ID NO:11).

FIG. 5D amino acid sequence of C1V1 (E122T):

MSRRPWLLALALAVALAAGSAGASTGSDATVPVATQDGPDYVFHRAHERMLFQTSYTL
ENNGSVICIPNNGQCFCLAWLKSNGTNAEKLAANILQWITFALSALCLMFYGYQTWKST
CGWETIYVATIEMIKFIIEYFHEFDEPAVIYSSNGNKTVWLRYAEWLLTCPVLLIHLSNLT
GLKDDYSKRTMGLLVSDVGCIVWGATSAMCTGWTKILFFLISLSYGMYTYFHAAKVYIE
AFHTVPKGICRELVRVMAWTFFVAWGMFPVLFLLGTEGFGHISPYGSAIGHSILDLIAKN
MWGVLGNYLRVKIHEHILLYGDIRKKQKITIAGQEMEVETLVAEEED (SEQ ID NO:12).

amino acid sequence of C1V1 (E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWEEIYVATIEMIKFIIEYFHEFDEPAVIYSSNGNKTVWLRYA<u>T</u>WLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED
(SEQ ID NO:13).

amino acid sequence of C1V1 (E122T/E162T):

MSRRPWLLALALAVALAAGSAGASTGSDATVPVATQDGPDYVFHRAHERMLFQTSY
TLENNGSVICIPNNGQCFCLAWLKSNGTNAEKLAANILQWITFALSALCLMFYGYQTW
KSTCGWE<u>T</u>IYVATIEMIKFIIEYFHEFDEPAVIYSSNGNKTVWLRYA<u>T</u>WLLTCPVLLIHL
SNLTGLKDDYSKRTMGLLVSDVGCIVWGATSAMCTGWTKILFFLISLSYGMYTYFHA
AKVYIEAFHTVPKGICRELVRVMAWTFFVAWGMFPVLFLLGTEGFGHISPYGSAIGHSI
LDLIAKNMWGVLGNYLRVKIHEHILLYGDIRKKQKITIAGQEMEVETLVAEEED
(SEQ ID NO:14).

**Amino acid sequence of *Dunaliella salina* channelrhodopsin**
(derived from *Dunaliella salina*)

```
mrrresqlay  lclfvliagw  aprltesapd  laerrppser  ntpyanikkv  pnitepnanv
qldgwalyqd  fyylagsdke  wvvgpsdqcy  crawskshgt  dregeaavvw  ayivfaiciv
qlvyfmfaaw  katvgweevy  vniielvhia  lviwvefdkp  amlylndgqm  vpwlrysawl
lscpvilihl  snltglkgdy  skrtmgllvs  digtivfgts  aalappnhvk  vilftiglly
glftfftaak  vyieayhtvp  kgqcrnlvra  mawtyfvswa  mfpilfilgr  egfghityfg
ssighfilei  fsknlwsllg  hglryrirqh  iiihgnltkk  nkiniagdnv  eveeyvdsnd
kdsdv (SEQ ID NO:15)
```

FIG. 5E amino acid sequence of NpHR without the native signal peptide:
*Natromonas pharaonis*
GenBank P15647.1

VTQRELFEFVLNDPLLASSLYINIALAGLSILLFVFMTRGLDDPRAKLIAVSTILVPVVSIAS
YTGLASGLTISVLEMPAGHFAEGSSVMLGGEEVDGVVTMWGRYLTWALSTPMILLALG
LLAGSNATKLFTAITFDIAMCVTGLAAALTTSSHLMRWFWYAISCACFLVVLYILLVEW
AQDAKAAGTADMFNTLKLLTVVMWLGYPIVWALGVEGIAVLPVGVTSWGYSFLDIVA
KYIFAFLLLNYLTSNESVVSGSILDVPSASGTPADD (SEQ ID NO:16).

amino acid sequence of eYFP-NpHR3.0:

<u>MTETLPPVTESAVALQAE</u>VTQRELFEFVLNDPLLASSLYINIALAGLSILLFVFMTRGLDD
PRAKLIAVSTILVPVVSIASYTGLASGLTISVLEMPAGHFAEGSSVMLGGEEVDGVVTMW
GRYLTWALSTPMILLALGLLAGSNATKLFTAITFDIAMCVTGLAAALTTSSHLMRWFWY
AISCACFLVVLYILLVEWAQDAKAAGTADMFNTLKLLTVVMWLGYPIVWALGVEGIAV
LPVGVTSWGYSFLDIVAKYIFAFLLLNYLTSNESVVSGSILDVPSASGTPADD<u>AAAKSRIT
SEGEYIPLDQIDIN</u>VVSKGEELFTGVVPILVELDGDVNGHKFSVSGEGEGDATYGKLTLKF
ICTTGKLPVPWPTLVTTFGYGLQCFARYPDHMKQHDFFKSAMPEGYVQERTIFFKDDGN
YKTRAEVKFEGDTLVNRIELKGIDFKEDGNILGHKLEYNYNSHNVYIMADKQKNGIKVN
FKIRHNIEDGSVQLADHYQQNTPIGDGPVLLPDNHYLSYQSALSKDPNEKRDHMVLLEF
VTAAGITLGMDELYK<u>FCYENEV</u> (SEQ ID NO:17).

<u>MTETLPPVTESAVALQAE</u> = native signal peptide
<u>KSRITSEGEYIPLDQIDIN</u> = membrane trafficking signal
<u>FCYENEV</u> = ER export signal
Double-underlined sequence = yellow fluorescent protein amino acid sequence of eYFP-NpHR3.1:

MVTQRELFEFVLNDPLLASSLYINIALAGLSILLFVFMTRGLDDPRAKLIAVSTILVPVVSI
ASYTGLASGLTISVLEMPAGHFAEGSSVMLGGEEVDGVVTMWGRYLTWALSTPMILLA
LGLLAGSNATKLFTAITFDIAMCVTGLAAALTTSSHLMRWFWYAISCACFLVVLYILLVE
WAQDAKAAGTADMFNTLKLLTVVMWLGYPIVWALGVEGIAVLPVGVTSWGYSFLDIV
AKYIFAFLLLNYLTSNESVVSGSILDVPSASGTPADD<u>AAAKSRITSEGEYIPLDQIDIN</u>VVS
KGEELFTGVVPILVELDGDVNGHKFSVSGEGEGDATYGKLTLKFICTTGKLPVPWPTLVT
TFGYGLQCFARYPDHMKQHDFFKSAMPEGYVQERTIFFKDDGNYKTRAEVKFEGDTLV
NRIELKGIDFKEDGNILGHKLEYNYNSHNVYIMADKQKNGIKVNFKIRHNIEDGSVQLAD
HYQQNTPIGDGPVLLPDNHYLSYQSALSKDPNEKRDHMVLLEFVTAAGITLGMDELYKF
CYENEV (SEQ ID NO:18).

<u>KSRITSEGEYIPLDQIDIN</u> = membrane trafficking signal
<u>FCYENEV</u> = ER export signal
Double-underlined sequence = yellow fluorescent protein

FIG. 5F

Amino acid sequence of a VChR1
(derived from *Volvox carteri*)
GenBank ACD70142

```
mdypvarsli vryptdlgng tvcmprgqcy cegwlrsrgt siektiaitl qwvvfalsva
clgwyayqaw ratcgweevy valiemmksi ieafhefdsp atlwlssgng vvwmrygewl
ltcpvllihl snltglkddy skrtmgllvs dvgcivwgat samctgwtki lfflislsyg
mytyfhaakv yieafhtvpk gicrelvrvm awtffvawgm fpvlfllgte gfghispygs
aighsildli aknmwgvlgn ylrvkihehi llygdirkkq kitiagqeme vetlvaeeed
```
(SEQ ID NO:19)

Amino acid sequence of a VChR1 SFO

```
mdypvarsli vryptdlgng tvcmprgqcy cegwlrsrgt siektiaitl qwvvfalsva
clgwyayqaw ratcgweevy valiemmksi ieafhefdsp atlwlssgng vvwmrygewl
ltspvllihl snltglkddy skrtmgllvs dvgcivwgat samctgwtki lfflislsyg
mytyfhaakv yieafhtvpk gicrelvrvm awtffvawgm fpvlfllgte gfghispygs
aighsildli aknmwgvlgn ylrvkihehi llygdirkkq kitiagqeme vetlvaeeed
```
(SEQ ID NO:20)

Bold and underlined: C123S

Amino acid sequence of a VChR1 SFO

```
mdypvarsli vryptdlgng tvcmprgqcy cegwlrsrgt siektiaitl qwvvfalsva
clgwyayqaw ratcgweevy valiemmksi ieafhefdsp atlwlssgng vvwmrygewl
ltcpvllihl snltglkddy skrtmgllvs avgcivwgat samctgwtki lfflislsyg
mytyfhaakv yieafhtvpk gicrelvrvm awtffvawgm fpvlfllgte gfghispygs
aighsildli aknmwgvlgn ylrvkihehi llygdirkkq kitiagqeme vetlvaeeed
```
(SEQ ID NO:21)

Bold and underlined: C123S and D151A

FIG. 5G

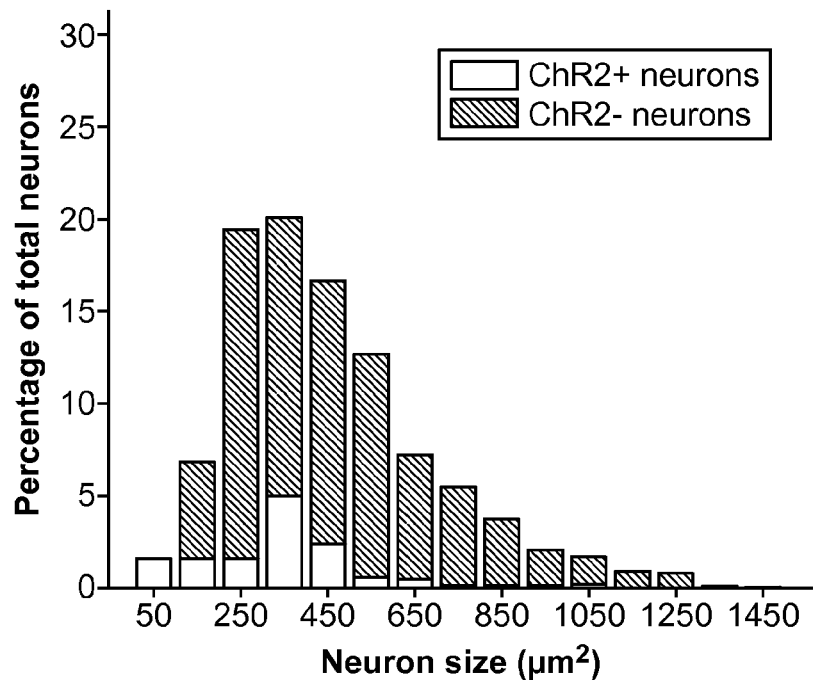
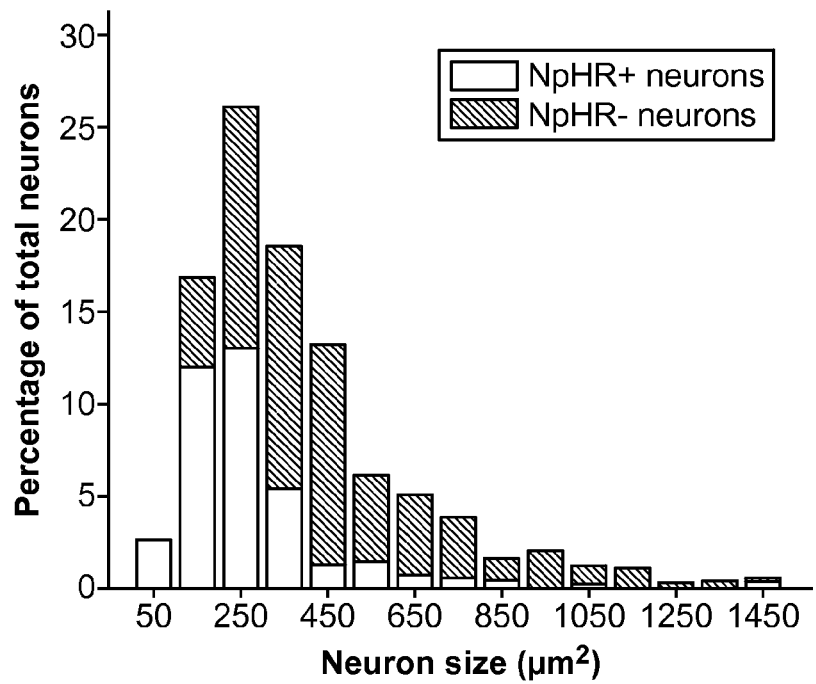
FIG. 6

Table 1: Opsin transduction profiles

|  |  | ChR2-eYFP | NpHR-eYFP | Average |
|---|---|---|---|---|
| Somatostatin | % YFP+ that are S+ | 33.33 | 13.28 | 20.69 |
|  | % S+ that are YFP+ | 32.47 | 28.81 | 30.88 |
| IB4 | % YFP+ that are IB4+ | 32.35 | 15.44 | 22.69 |
|  | % IB4+ that are YFP+ | 13.64 | 3.61 | 6.55 |
| Substance P | % YFP+ that are SP+ | 1.04 | 5.38 | 3.54 |
|  | % SP+ that are YFP+ | 1.89 | 19.44 | 8.99 |
| VR1 | % YFP+ that are VR1+ | 19.83 | 25.00 | 22.54 |
|  | % VR1+ that are YFP+ | 28.75 | 31.37 | 30.22 |

FIG. 9

COMPOSITIONS AND METHODS FOR CONTROLLING PAIN

CROSS-REFERENCE

This application is a national stage application under 35 U.S.C. § 371 of PCT/US2014/050938, filed Aug. 13, 2014, which claims the benefit of U.S. Provisional Patent Application No. 61/865,962, filed Aug. 14, 2013, which applications are incorporated herein by reference in their entirety.

STATEMENT REGARDING FEDERALLY SPONSORED RESEARCH

This invention was made with government support under Grant No. NS080954 awarded by the National Institutes of Health. The government has certain rights in the invention.

INTRODUCTION

Primary nociceptors are the first neurons in a complex pain-processing system that regulates normal and pathological pain. The ability to excite and inhibit these neurons for the purposes of research and therapy has been limited by pharmacological and electrical stimulation constraints; thus non-invasive, spatially localized control of nociceptors in freely moving animals has not been possible.

LITERATURE

Liske et al. (2013) *Muscle & Nerve* 47:916; Llewellyn et al. (2010) *Nature Med.* 16:1161; Ji et al. (2012) *PLoS One* 7:e32699; Wang and Zylka (2009) *J. Neurosci.* 29:13020; Daou et al. (2012) *Soc. Neurosci. Conf.* 575.06/1111; Daou et al. (2013) *J. Neurosci.* 33:47; Mourot et al. (2012) *Nat. Methods* 9:396; Kokel et al. (2013) *Nat. Chem. Biol.* 9:257; Mattis et al. (2012) *Nat. Methods* 9:159; Williams and Denison (2013) *Sci. Trani. Med.* 5:177ps6; Chow and Boyden (2013) *Sci. Transl. Med.* 5:177ps5; Towne et al. (2010) *Gene Ther.* 17:141; Towne et al. (2009) *Mol. Pain* 5:52; Iyer et al. (2014) *Nat. Biotech.* 32:3.

SUMMARY

The present disclosure provides compositions and methods for controlling pain. The present disclosure provides methods for identifying agents that control pain.

Features

The present disclosure features a method for controlling pain in an individual, the method comprising introducing into a nociceptor of the individual a nucleic acid comprising a nucleotide sequence encoding an opsin polypeptide that provides for hyperpolarization of the nociceptor in response to light of a wavelength that activates the opsin. In some cases, the light is delivered transdermally. In some cases, the opsin comprises an amino acid sequence having at least about 75% amino acid sequence identity to one of SEQ ID NOs:1, 3, 4, 6, 15, and 16. In some cases, the pain is neuropathic pain. In some cases, the nucleic acid comprising a nucleotide encoding the opsin is administered to the individual via injection into a nerve, via intramuscular injection, or via intravenous injection. In some cases, the nucleic acid is administered to the individual at or near a treatment site (e.g., a site of pain). In some cases, the nucleic acid is a recombinant expression vector, e.g., the recombinant expression vector is a viral vector. In some instances, where the recombinant expression vector is a viral vector, the viral vector is a lentivirus vector or an adeno-associated virus (AAV) vector. In some instances, the AAV vector is an AAV6 vector or an AAV8 vector. The nucleotide sequence can be operably linked to a promoter that provides for selective expression in a neuron. For example, the promoter can be a synapsin-I promoter, a human synuclein 1 promoter, a human Thy1 promoter, or a calcium/calmodulin-dependent kinase II alpha (CAMKIIα) promoter. The individual can be a mammal; e.g., a human, a rat, or a mouse. In some case, activation of the opsin provides for an at least 10%, at least 20%, at least 25%, at least 30%, at least 40%, at least 50%, at least 60%, at least 70%, at least 80%, or at least 90%, reduction in pain. In some case, activation of the opsin provides a 100% reduction in pain, i.e., the individual experiences substantially no pain.

The present disclosure features a non-human animal model of neuropathic pain, where the non-human animal expresses in a nociceptor of the animal a nucleic acid comprising a nucleotide sequence encoding an opsin polypeptide that provides for depolarization of the nociceptor in response to light of a wavelength that activates the opsin. In some cases, the opsin comprises an amino acid sequence having at least about 75% amino acid sequence identity to one of SEQ ID NOs:8-14 and 19-21. In some cases, the nucleic acid is a recombinant expression vector, e.g., a viral vector. For example, in some cases, the viral vector is a lentivirus vector or an adeno-associated virus (AAV) vector, e.g., an AAV6 vector or an AAV8 vector. In some instances, the nucleotide sequence encoding the opsin is operably linked to a promoter that provides for selective expression in a neuron; e.g., the promoter can be a synapsin-I promoter, a human synuclein 1 promoter, a human Thy1 promoter, or a calcium/calmodulin-dependent kinase II alpha (CAMKIIα) promoter. In some instances, the animal is a rat. In some instances, the animal is a mouse.

The present disclosure features a method of identifying an agent that reduces pain, the method comprising: a) administering a test agent to a subject non-human animal; and b) determining the effect, if any, of the test agent on pain when the depolarizing light-activated polypeptide is activated with light, where a test agent that reduces pain in the non-human animal, compared to the level of pain induced by light activation of the depolarizing light-activated polypeptide in the absence of the test agent, indicates that the test agent is a candidate agent for reducing pain.

The present disclosure features a method of identifying an agent that reduces pain, the method comprising: a) administering a test agent to a subject non-human animal; and b) determining the effect, if any, of the test agent on the amount of light required to induce pain through the activation of a depolarizing light-activated polypeptide following administration of the test agent, wherein a test agent that increases the amount of light required to produce a sign of pain, compared with the amount of light required to produce a sign of pain in the absence of the test agent indicates that the test agent is a candidate agent for reducing pain.

BRIEF DESCRIPTION OF THE DRAWINGS

FIGS. 5A-G depict amino acid sequences of various light-activated polypeptides.

FIGS. 6A and 6B depict size distribution of opsin transduction.

FIG. 9 provides Table 1.

DEFINITIONS

Figure 1:
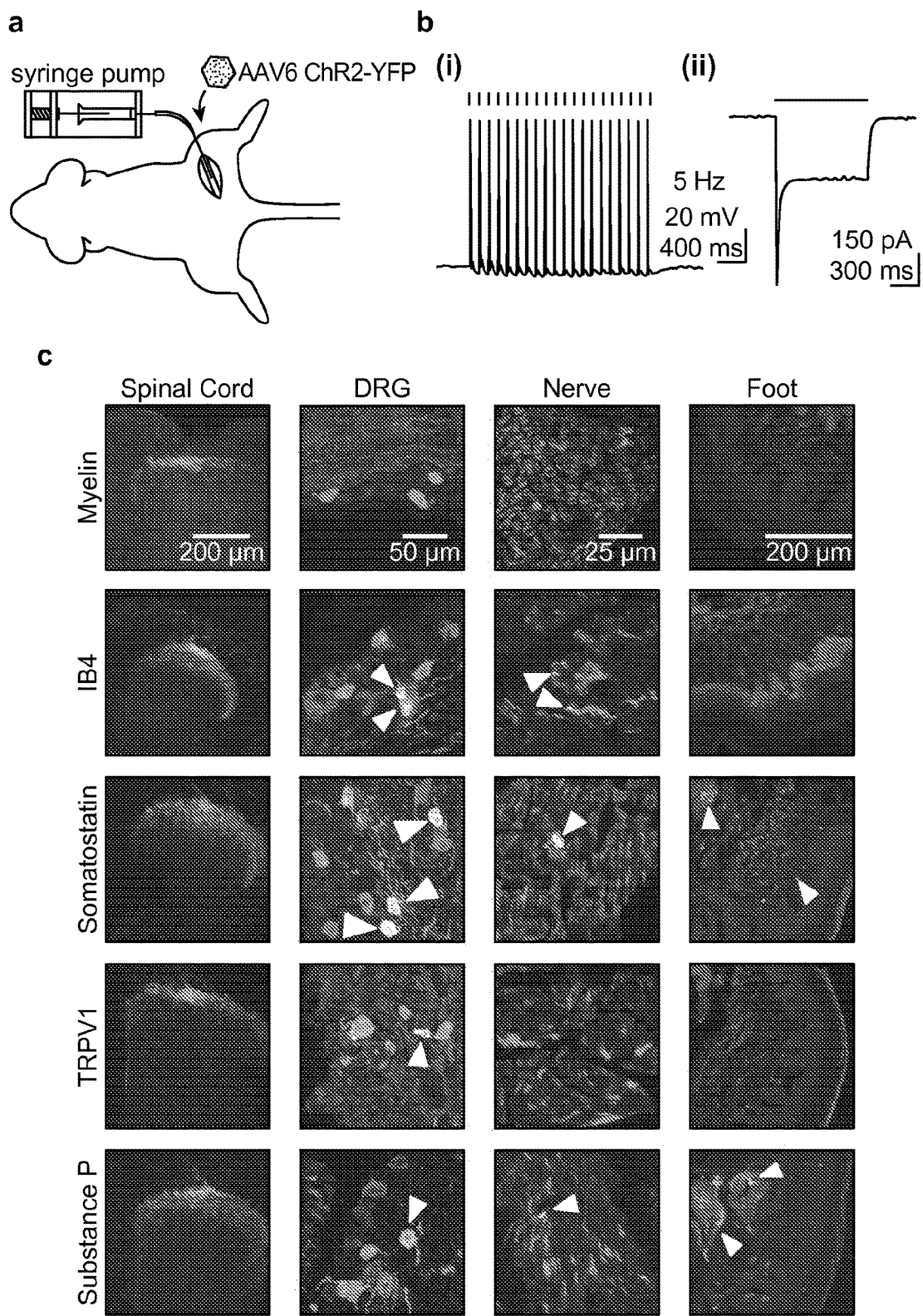
FIGS. 1A-C depict data showing that intra-sciatic injection of rAAV2/6-hSyn-ChR2(H134R)-eYFP transduced unmyelinated nociceptors that projected to spinal cord lamina.

As used herein, an "individual," "subject," or "patient" is an animal, e.g., a mammal, including a human. Mammals include, but are not limited to, ungulates, canines, felines, bovines, ovines, non-human primates, lagomorphs, and rodents (e.g., mice and rats). In one aspect, an individual is a human. In another aspect, an individual is a non-human mammal.

Amino acid substitutions in a native protein sequence may be "conservative" or "non-conservative" and such substituted amino acid residues may or may not be one encoded by the genetic code. A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain). The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine).

As used herein, an "effective dosage" or "effective amount" of a recombinant expression vector, or a pharmaceutical composition comprising a recombinant expression vector, is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective dosage can be administered in one or more administrations. For purposes of this disclosure, an effective dosage of a recombinant expression vector, or a pharmaceutical composition comprising a recombinant expression vector, is an amount sufficient to accomplish prophylactic or therapeutic treatment either directly or indirectly. For example, an effective dosage of a recombinant expression vector, or a pharmaceutical composition comprising a recombinant expression vector, can be an amount sufficient to reduce pain (e.g., neuropathic pain). As is understood in the clinical context, an effective dosage of a recombinant expression vector, or a pharmaceutical composition comprising a recombinant expression vector, may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this disclosure, beneficial or desired clinical results include, but are not limited to, one or more of the following: decreasing symptoms resulting from the disease, increasing the quality of life of those suffering from the disease, decreasing the dose of other medications required to treat the disease, delaying the progression of the disease, and/or prolonging survival of individuals. For example, "treatment" or "treating" can refer to reduction in pain.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an opsin" includes a plurality of such opsin and reference to "the nociceptor" includes reference to one or more nociceptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides compositions and methods for controlling pain in an individual. The present disclosure provides methods for identifying agents that control pain.

Methods of Reducing Pain

The present disclosure provides compositions and methods for controlling pain in an individual. In some cases, methods for controlling pain according to the present disclosure generally involve introducing into a neuron of an individual a nucleic acid comprising a nucleotide sequence encoding an opsin that provides for hyperpolarization of the cell in response to light of a wavelength that activates the opsin; such a method provides for reduction of pain. The nucleic acid enters the neuron (e.g., a primary afferent neuron, such as a small- or a large-diameter primary afferent neuron; e.g., a nociceptor), the opsin is produced in the neuron, and the opsin is inserted into the cell membrane. The terms "opsin," "light-responsive protein," "light-responsive polypeptide," "light-activated protein," and "light-activated polypeptide," are used interchangeably herein.

In some cases, a nucleic acid comprising a nucleotide sequence encoding an opsin that provides for hyperpolarization of the cell in response to light of a wavelength that activates the opsin provides for expression of the opsin in a neuron (e.g., primary afferent neuron; e.g., a nociceptor). In some cases, a nucleic acid comprising a nucleotide sequence encoding an opsin that provides for hyperpolarization of the cell in response to light of a wavelength that activates the opsin provides for expression of the opsin in a sub-population of nociceptors. Targeting expression of a light-activated polypeptide to a sub-population of nociceptors can be achieved by one or more of: selection of the vector (e.g., AAV6; AAV1; AAV8; etc.); selection of a promoter; and delivery means. For example, injection into the sciatic nerve can provide for production of a light-activated polypeptide in unmyelinated nociceptors (putative C-fibers).

The present disclosure provides methods for reducing pain, e.g., pain such as acute pain, chronic pain, neuropathic pain, nociceptive pain, allodynia, inflammatory pain, inflammatory hyperalgesia, neuropathies, neuralgia, diabetic neuropathy, human immunodeficiency virus-related neuropathy, nerve injury, rheumatoid arthritic pain, osteoarthritic pain, burns, back pain, eye pain, visceral pain, cancer pain (e.g. bone cancer pain), dental pain, headache, migraine, carpal tunnel syndrome, fibromyalgia, neuritis, sciatica, pelvic hypersensitivity, pelvic pain, post herpetic neuralgia, post-operative pain, post stroke pain, and menstrual pain.

Pain can be classified as acute or chronic. Acute pain begins suddenly and is short-lived (usually in twelve weeks or less). It is usually associated with a specific cause such as a specific injury and is often sharp and severe. It is the kind of pain that can occur after specific injuries resulting from surgery, dental work, a strain, or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain. In some cases, a method of the present disclosure is effective in reducing acute pain. In some cases, a method of the present disclosure is effective in reducing chronic pain.

Clinical pain is present when discomfort and abnormal sensitivity feature among the patient's symptoms. Individuals can present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive pain, inflammatory pain, and neuropathic pain. In some cases, a method of the present disclosure is effective in reducing nociceptive pain. In some cases, a method of the present disclosure is effective in reducing inflammatory pain. In some cases, a method of the present disclosure is effective in reducing neuropathic pain.

Nociceptive pain is induced by tissue injury or by intense stimuli with the potential to cause injury. Moderate to severe acute nociceptive pain is a prominent feature of pain from central nervous system trauma, strains/sprains, burns, myocardial infarction and acute pancreatitis, post-operative pain (pain following any type of surgical procedure), posttraumatic pain, renal colic, cancer pain and back pain. Cancer pain may be chronic pain such as tumor related pain (e.g.

bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain can be defined as pain initiated or caused by a primary lesion or dysfunction in the nervous system. Etiologies of neuropathic pain include, e.g., peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy, and vitamin deficiency.

The inflammatory process is a complex series of biochemical and cellular events, activated in response to tissue injury or the presence of foreign substances, which results in swelling and pain. Arthritic pain is a common inflammatory pain.

Other types of pain include: pain resulting from musculoskeletal disorders, including myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardical infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome, and temporomandibular myofascial pain.

In some cases, a subject method of reducing pain involves introducing into a nociceptor (a sensory neuron that responds to potentially damaging stimuli by sending nerve signals to the spinal cord and brain) a nucleic acid comprising a nucleotide sequence encoding an opsin that provides for hyperpolarization of the nociceptor in response to light of a wavelength that activates the opsin, thereby reducing pain. The nociceptor can be a thermal nociceptor, a mechanical nociceptor, a chemical nociceptor, or other type of nociceptor. Nociceptive markers include, but are not limited to, IB4, Substance P, TRPV1, and somatostatin.

Whether pain is reduced can be determined in a human subject using a variety of pain scales. Patient self-reporting can be used to assess whether pain is reduced; see, e.g., Katz and Melzack (1999) *Surg. Clin. North Am.* 79:231. Alternatively, an observational pain scale can be used. The LANSS Pain Scale can be used to assess whether pain is reduced; see, e.g., Bennett (2001) *Pain* 92:147. A visual analog pain scale can be used; see, e.g., Schmader (2002) *Clin. J. Pain* 18:350. The Likert pain scale can be used; e.g., where 0 is no pain, 5 is moderate pain, and 10 is the worst pain possible. Self-report pain scales for children include, e.g., Faces Pain Scale; Wong-Baker FACES Pain Rating Scale; and Colored Analog Scale. Self-report pain scales for adults include, e.g., Visual Analog Scale; Verbal Numerical Rating Scale; Verbal Descriptor Scale; and Brief Pain Inventory. Pain measurement scales include, e.g., Alder Hey Triage Pain Score (Stewart et al. (2004) *Arch. Dis. Child.* 89:625); Behavioral Pain Scale (Payen et al. (2001) *Critical Care Medicine* 29:2258); Brief Pain Inventory (Cleeland and Ryan (1994) *Ann. Acad. Med. Singapore* 23:129); Checklist of Nonverbal Pain Indicators (Feldt (2000) *Pain Manag. Nurs.* 1:13); Critical-Care Pain Observation Tool (Gelinas et al. (2006) *Am. J. Crit. Care* 15:420); COMFORT scale (Ambuel et al. (1992) *J. Pediatric Psychol.* 17:95); Dallas Pain Questionnaire (Ozguler et al. (2002) *Spine* 27:1783); Dolorimeter Pain Index (Hardy et al. (1952) *Pain Sensations and Reactions* Baltimore: The Williams & Wilkins Co.); Faces Pain Scale—Revised (Hicks et al. (2001) *Pain* 93:173); Face Legs Activity Cry Consolability Scale; McGill Pain Questionnaire (Melzack (1975) *Pain* 1:277); Descriptor Differential Scale (Gracely and Kwilosz (1988) *Pain* 35:279); Numerical 11 point Box (Jensen et al. (1989) *Clin. J. Pain* 5:153); Numeric Rating Scale (Hartrick et al. (2003) *Pain Pract.* 3:310); Wong-Baker FACES Pain Rating Scale; and Visual Analog Scale (Huskisson (1982) *J. Rheumatol.* 9:768).

In some cases, the light used to activate an opsin expressed in a neuron (e.g., a nociceptor) has an intensity of from about 0.05 mW/mm$^2$ to about 0.1 mW/mm$^2$, from about 0.1 mW/mm$^2$ to about 0.2 mW/mm$^2$, from about 0.2 mW/mm$^2$ to about 0.3 mW/mm$^2$, from about 0.3 mW/mm$^2$ to about 0.4 mW/mm$^2$, from about 0.4 mW/mm$^2$ to about 0.5 mW/mm$^2$, from about 0.5 mW/mm$^2$ to about 0.6 mW/mm$^2$, from about 0.6 mW/mm$^2$ to about 0.7 mW/mm$^2$, from about 0.7 mW/mm$^2$ to about 0.8 mW/mm$^2$, from about 0.8 mW/mm$^2$ to about 0.9 mW/mm$^2$, or from about 0.9 mW/mm$^2$ to about 1.0 mW/mm$^2$. In some cases, the light used to activate an opsin expressed in a neuron (e.g., a nociceptor) has an intensity of from about 1.0 mW/mm$^2$ to about 1.1 mW/mm$^2$, from about 1.1 mW/mm$^2$ to about 1.2 mW/mm$^2$, from about 1.2 mW/mm$^2$ to about 1.3 mW/mm$^2$, from 1.3 mW/mm$^2$ to about 1.4 mW/mm$^2$, from about 1.4 mW/mm$^2$ to about 1.5 mW/mm$^2$, from about 1.5 mW/mm$^2$ to about 1.6 mW/mm$^2$, from about 1.6 mW/mm$^2$ to about 1.7 mW/mm$^2$, from about 1.7 mW/mm$^2$ to about 1.8 mW/mm$^2$, from about 1.8 mW/mm$^2$ to about 1.9 mW/mm$^2$, from about 1.9 mW/mm$^2$ to about 2.0 mW/mm$^2$, from about 2.0 mW/mm$^2$ to about 2.5 mW/mm$^2$, from about 2.5 mW/mm$^2$ to about 3 mW/mm$^2$, from about 3 mW/mm$^2$ to about 3.5 mW/mm$^2$, from about 3.5 mW/mm$^2$ to about 4 mW/mm$^2$, from about 4 mW/mm$^2$ to about 4.5 mW/mm$^2$, from about 4.5 mW/mm$^2$ to about 5 mW/mm$^2$, from about 5 mW/mm$^2$ to about 5.5 mW/mm$^2$, from about 5.5 mW/mm$^2$ to about 6 mW/mm$^2$, from about 6 mW/mm$^2$ to about 7 mW/mm$^2$, or from about 7 mW/mm$^2$ to about 10 mW/mm$^2$. In some cases, the light used to activate an opsin expressed in a neuron (e.g., a nociceptor) has an intensity of from about 0.05 mW/mm$^2$ to about 0.1 mW/mm$^2$. In some cases, the light used to activate an opsin expressed in a neuron (e.g., a nociceptor) has an intensity of about 0.25 mW/mm$^2$. In some cases, the light used to activate an opsin expressed in a neuron (e.g., a nociceptor) has an intensity of about 1 mW/mm$^2$.

In some cases, the light is delivered transdermally or transcutaneously. In some cases, an implantable light source is used; and the light is delivered to a site within the body. In some cases, the light is delivered to a treatment site within the body. In some cases, the light is delivered intracranially.

A nucleic acid comprising a nucleotide sequence encoding an opsin that provides for hyperpolarization of the cell in response to light of a wavelength that activates the opsin can be introduced into a neuron (e.g., a nociceptor) by any convenient means. For example, a nucleic acid comprising a nucleotide sequence encoding an opsin that provides for hyperpolarization of the cell in response to light of a wavelength that activates the opsin can be introduced (e.g., injected) into a nerve bundle or nerve fiber, such that the nucleic acid enters a neuron (e.g., a nociceptor), where the opsin is produced in the neuron and is inserted into the cell membrane. A nucleic acid comprising a nucleotide sequence encoding an opsin that provides for hyperpolarization of the cell in response to light of a wavelength that activates the opsin can be introduced (e.g., injected) proximal to a nerve. Stereotactic injection can be used; see, e.g., Stein et al., *J. Virol*, 73:34243429, 1999; Davidson et al., *PNAS*, 97:3428-3432, 2000; Davidson et al., *Nat. Genet.* 3:219-223, 1993; and Alisky & Davidson, *Hum. Gene Ther.* 11:2315-2329, 2000, the contents of each of which are hereby incorporated by reference herein in their entireties.

A nucleic acid comprising a nucleotide sequence encoding an opsin that provides for hyperpolarization of the cell in response to light of a wavelength that activates the opsin can be introduced (e.g., injected) intramuscularly. A nucleic acid comprising a nucleotide sequence encoding an opsin that provides for hyperpolarization of the cell in response to light of a wavelength that activates the opsin can be administered via any means, including, e.g., intravenous, intramuscular, intracranial, into a nerve, at or near a treatment site, and the like. Administration of an opsin-encoding nucleic acid can be carried out via injection; via implantation at or near a treatment site of a composition comprising a nucleic acid encoding a light-activated polypeptide; via a catheter; or via any other means of delivery Administration of an opsin-encoding nucleic acid can be carried out via topical, intradermal, intravenous, intrathecal, or intrapleural administration. Administration of an opsin-encoding nucleic acid can be carried out via intradermal administration.

A light-activated protein (opsin) can be implanted into or proximal to a nerve using a number of different methods. Example methods include, but are not limited to, the use of various delivery devices, such as gelatin capsules, liquid injections and the like. Such methods also include the use of stereotactic surgery techniques such as frames or computerized surgical navigation systems to implant or otherwise access areas of the body.

In some cases, a nucleic acid comprising a nucleotide sequence encoding a light-responsive opsin protein can be delivered directly to the neurons responsible for pain, where the delivery can be accomplished with a needle, catheter, or related device, using neurosurgical techniques known in the art, such as by stereotactic injection or fluoroscopy. Other methods to deliver a nucleic acid comprising a nucleotide sequence encoding a light-responsive opsin protein to the nerves of interest can also be used, such as, but not limited to, transfection with ionic lipids or polymers, electroporation, optical transfection, impalefection, or via gene gun.

Hyperpolarizing Light-Responsive Polypeptides

As discussed above, methods for controlling pain according to the present disclosure generally involve introducing into a neuron of an individual a nucleic acid comprising a nucleotide sequence encoding a light-activated polypeptide (an opsin) that provides for hyperpolarization of the cell in response to light of a wavelength that activates the light-activated polypeptide. A light-activated polypeptide can be a polypeptide that allows one or more ions to pass through the plasma membrane of a target cell when the protein is illuminated with light of an activating wavelength. Light-activated proteins may be characterized as ion pump proteins, which facilitate the passage of a small number of ions through the plasma membrane per photon of light, or as ion channel proteins, which allow a stream of ions to freely flow through the plasma membrane when the channel is open. Suitable light-activated proteins for use in a subject method of reducing pain include hyperpolarizing light-activated polypeptides.

Examples of suitable light-responsive polypeptides include, e.g., the Halorhodopsin family of light-responsive chloride pumps (e.g., NpHR, NpHR2.0, NpHR3.0, NpHR3.1). As another example, the GtR3 proton pump can be used to promote neural cell membrane hyperpolarization in response to light. As another example, eArch (a proton pump) can be used to promote neural cell membrane hyperpolarization in response to light. As another example, an ArchT opsin protein or a Mac opsin protein can be used to promote neural cell membrane hyperpolarization in response to light.

Enhanced Intracellular Transport Amino Acid Motifs

In some embodiments, the light-responsive opsin proteins expressed in a cell can be fused to one or more amino acid sequence motifs selected from the group consisting of a signal peptide, an ER export signal, a membrane trafficking signal, and/or an N-terminal golgi export signal. The one or more amino acid sequence motifs which enhance light-responsive protein transport to the plasma membranes of mammalian cells can be fused to the N-terminus, the C-terminus, or to both the N- and C-terminal ends of the light-responsive protein. In some cases, the one or more amino acid sequence motifs which enhance light-responsive protein transport to the plasma membranes of mammalian cells is fused internally within a light-activated polypeptide. Optionally, the light-responsive protein and the one or more amino acid sequence motifs may be separated by a linker. In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22).

Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYI-PLDQIDINV (SEQ ID NO:22)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGAL-SAVGRELLFVTNPVVVNGS (SEQ ID NO:23))

2) the β2 subunit signal peptide of the neuronal nicotinic acetylcholine receptor (e.g., MAGHSNSMALFSFSLL-WLCSGVLGTEF (SEQ ID NO:24));

3) a nicotinic acetylcholine receptor signal sequence (e.g., MGLRALMLWLLAAAGLVRESLQG (SEQ ID NO:25)); and 4) a nicotinic acetylcholine receptor signal sequence (e.g., MRGTPLLLVVSLFSLLQD (SEQ ID NO:26)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

ER export sequences that are suitable for use in a modified opsin include, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the signal peptide sequence in the protein can be deleted or substituted with a signal peptide sequence from a different protein.

Arch

In some embodiments, a suitable light-activated protein is an Archaerhodopsin (Arch) proton pump (e.g., a proton pump derived from *Halorubrum sodomense*) that can transport one or more protons across the plasma membrane of a cell when the cell is illuminated with light. The light can have a wavelength between about 530 and about 595 nm or can have a wavelength of about 560 nm. In some embodiments, the Arch protein can comprise an amino acid sequence that is at least 75%, 85%, 90%, 91%, 92%, 93%, 94%, 95%, 96%, 97%, 98%, 99%, or 100% identical to the sequence shown in SEQ ID NO:1 (Arch). The Arch protein can additionally comprise substitutions, deletions, and/or insertions introduced into a native amino acid sequence to increase or decrease sensitivity to light, increase or decrease sensitivity to particular wavelengths of light, and/or increase or decrease the ability of the Arch protein to transport ions across the plasma membrane of a target cell. Additionally, the Arch protein can contain one or more conservative amino acid substitutions and/or one or more non-conservative amino acid substitutions. The Arch protein comprising substitutions, deletions, and/or insertions introduced into the native amino acid sequence suitably retains the ability to transport ions across the plasma membrane of a target cell in response to light.

In some embodiments, an Arch protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the Arch protein comprises an N-terminal signal peptide and a C-terminal ER export signal. In some embodiments, the Arch protein comprises an N-terminal signal peptide and a C-terminal trafficking signal. In some embodiments, the Arch protein comprises an N-terminal signal peptide, a C-terminal ER export signal, and a C-terminal trafficking signal. In some embodiments, the Arch protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

ArchT

In some embodiments, a suitable light-activated protein is an Archaerhodopsin (ArchT) proton pump (e.g., a proton pump derived from *Halorubrum* sp. TP009) that can transport one or more protons across the plasma membrane of a cell when the cell is illuminated with light. The light can have a wavelength between about 530 and about 595 nm or can have a wavelength of about 560 nm. In some embodiments, the Arch protein can comprise an amino acid sequence that is at least 75%, 85%, 90%, 91%, 92%, 93%, 94%, 95%, 96%, 97%, 98%, 99%, or 100% identical to the sequence shown in SEQ ID NO:3 (ArchT). The ArchT protein can additionally comprise substitutions, deletions, and/or insertions introduced into a native amino acid sequence to increase or decrease sensitivity to light, increase or decrease sensitivity to particular wavelengths of light, and/or increase or decrease the ability of the ArchT protein to transport ions across the plasma membrane of a target cell. Additionally, the ArchT protein can contain one or more conservative amino acid substitutions and/or one or more non-conservative amino acid substitutions. The ArchT protein comprising substitutions, deletions, and/or insertions introduced into the native amino acid sequence suitably retains the ability to transport ions across the plasma membrane of a target cell in response to light.

In some cases, the ArchT polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCY-ENEVALTSK (SEQ ID NO:29); FXYENE (SEQ ID NO:30) (where X is any amino acid), e.g., FCYENEV (SEQ ID NO:31); and the like.

GtR3

In some embodiments, the light-responsive proton pump protein can be responsive to blue light and can be derived from *Guillardia theta*, wherein the proton pump protein can be capable of mediating a hyperpolarizing current in the cell when the cell is illuminated with blue light. The light can have a wavelength between about 450 and about 495 nm or can have a wavelength of about 490 nm. In another embodiment, the light-responsive proton pump protein can comprise an amino acid sequence at least 85%, 90%, 91%, 92%, 93%, 94%, 95%, 96%, 97%, 98%, 99%, or 100% identical to the sequence shown in SEQ ID NO:4 (GtR3). The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to hyperpolarize the plasma membrane of a neuronal cell in response to light.

In other aspects of the methods disclosed herein, the light-responsive proton pump protein can comprise a core amino acid sequence at least 75%, 85%, 90%, 91%, 92%, 93%, 94%, 95%, 96%, 97%, 98%, 99%, or 100% identical to the sequence shown in SEQ ID NO:4 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCY-ENEVALTSK (SEQ ID NO:29); FXYENE (SEQ ID NO:30) (where X is any amino acid), e.g., FCYENEV (SEQ ID NO:31); and the like.

Also provided herein are isolated polynucleotides encoding any of the light-responsive proton pump proteins described herein, such as a light-responsive proton pump protein comprising a core amino acid sequence at least 75%, 85%, 90%, 91%, 92%, 93%, 94%, 95%, 96%, 97%, 98%, 99%, or 100% identical to the sequence shown in SEQ ID NO:4. Also provided herein are expression vectors (such as a viral vector described herein) comprising a polynucleotide encoding the proteins described herein, such as a light-responsive proton pump protein comprising a core amino acid sequence at least about 90%, 91%, 92%, 93%, 94%, 95%, 96%, 97%, 98%, 99%, or 100% identical to the sequence shown in SEQ ID NO:4.

Oxy

In some embodiments, a light-activated protein is an *Oxyrrhis marina* (Oxy) proton pump that can transport one or more protons across the plasma membrane of a cell when the cell is illuminated with light. The light can have a wavelength between about 500 and about 560 nm or can have a wavelength of about 530 nm. In some embodiments, the Oxy protein can comprise an amino acid sequence that is at least 75%, 85%, 90%, 91%, 92%, 93%, 94%, 95%, 96%, 97%, 98%, 99%, or 100% identical to the sequence shown in SEQ ID NO:5. The Oxy protein can additionally comprise substitutions, deletions, and/or insertions introduced into a native amino acid sequence to increase or decrease sensitivity to light, increase or decrease sensitivity to particular wavelengths of light, and/or increase or decrease the ability of the Oxy protein to transport ions across the plasma membrane of a target cell. Additionally, the Oxy protein can contain one or more conservative amino acid substitutions and/or one or more non-conservative amino acid substitutions. The Oxy protein comprising substitutions, deletions, and/or insertions introduced into the native amino acid sequence suitably retains the ability to transport ions across the plasma membrane of a target cell in response to light.

In some embodiments, an Oxy protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the Oxy protein comprises an N-terminal signal peptide and a C-terminal ER export signal. In some embodiments, the Oxy protein comprises an N-terminal signal peptide and a C-terminal trafficking signal. In some embodiments, the Oxy protein comprises an N-terminal signal peptide, a C-terminal ER export signal, and a C-terminal trafficking signal. In some embodiments, the Oxy protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

Mac

In some embodiments, the light-responsive proton pump protein can be responsive to light and can be derived from *Leptosphaeria maculans*, wherein the proton pump protein can be capable of pumping protons across the membrane of a cell when the cell is illuminated with 520 nm to 560 nm light. The light can have a wavelength between about 520 nm to about 560 nm. In another embodiment, the light-responsive proton pump protein can comprise an amino acid sequence at least 75%, 85%, 90%, 91%, 92%, 93%, 94%, 95%, 96%, 97%, 98%, 99%, or 100% identical to the sequence shown in SEQ ID NO:6 or SEQ ID NO:7 (Mac; Mac 3.0). The light-responsive proton pump protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive proton pump protein to regulate the polarization state of the plasma membrane of the cell. Additionally, the light-responsive proton pump protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to pump protons across the plasma membrane of a neuronal cell in response to light.

In other aspects of the methods disclosed herein, the light-responsive proton pump protein can comprise a core amino acid sequence at least 75%, 85%, 90%, 91%, 92%, 93%, 94%, 95%, 96%, 97%, 98%, 99%, or 100% identical to the sequence shown in SEQ ID NO:6 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton pump protein comprises an N-terminal signal peptide and a C-terminal ER export signal. In some embodiments, the light-responsive proton pump protein comprises an N-terminal signal peptide and a C-terminal trafficking signal. In some embodiments, the light-responsive proton pump protein comprises an N-terminal signal peptide, a C-terminal ER Export signal, and a C-terminal trafficking signal. In some embodiments, the light-responsive proton pump protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

Also provided herein are isolated polynucleotides encoding any of the light-responsive proton pump proteins described herein, such as a light-responsive proton pump protein comprising a core amino acid sequence at least 75%, 85%, 90%, 91%, 92%, 93%, 94%, 95%, 96%, 97%, 98%, 99%, or 100% identical to the sequence shown in SEQ ID NO:6. Also provided herein are expression vectors (such as a viral vector described herein) comprising a polynucleotide encoding the proteins described herein, such as a light-responsive proton pump protein comprising a core amino acid sequence at least 85%, 90%, 91%, 92%, 93%, 94%, 95%, 96%, 97%, 98%, 99%, or 100% identical to the sequence shown in SEQ ID NO:6.

Further disclosure related to light-activated proton pump proteins can be found in International Patent Application No. PCT/US2011/028893, the disclosure of which is hereby incorporated by reference in its entirety.

NpHR

In some cases, a suitable light-responsive chloride pump proteins expressed on the plasma membranes of the neurons described above can be derived from *Natronomonas pharaonic*. In some embodiments, the light-responsive chloride pump proteins can be responsive to amber light as well as red light and can mediate a hyperpolarizing current in the neuron when the light-responsive chloride pump proteins are illuminated with amber or red light. The wavelength of light which can activate the light-responsive chloride pumps can be between about 580 and 630 nm. In some embodiments, the light can be at a wavelength of about 589 nm or the light can have a wavelength greater than about 630 nm (e.g. less than about 740 nm). In another embodiment, the light has a wavelength of around 630 nm. In some embodiments, the light-responsive chloride pump protein can hyperpolarize a neural membrane for at least about 90 minutes when exposed to a continuous pulse of light. In some embodiments, the light-responsive chloride pump protein can comprise an amino acid sequence at least about 75%, 85%, 90%, 91%, 92%, 93%, 94%, 95%, 96%, 97%, 98%, 99%, or 100% identical to the sequence shown in SEQ ID NO:16. Additionally, the light-responsive chloride pump protein can comprise substitutions, deletions, and/or insertions introduced into a native amino acid sequence to increase or decrease sensitivity to light, increase or decrease sensitivity to particular wavelengths of light, and/or increase or decrease the ability of the light-responsive protein to regulate the polarization state of the plasma membrane of the cell. In some embodiments, the light-responsive chloride pump protein contains one or more conservative amino acid substitutions. In some embodiments, the light-responsive protein contains one or more non-conservative amino acid substitutions. The light-responsive protein comprising substitutions, deletions, and/or insertions introduced into the native amino acid sequence suitably retains the ability to hyperpolarize the plasma membrane of a neuronal cell in response to light.

Additionally, in other aspects, the light-responsive chloride pump protein can comprise a core amino acid sequence at least about 75%, 85%, 90%, 91%, 92%, 93%, 94%, 95%, 96%, 97%, 98%, 99%, or 100% identical to the sequence shown in SEQ ID NO:16 and an endoplasmic reticulum (ER) export signal. This ER export signal can be fused to the C-terminus of the core amino acid sequence or can be fused to the N-terminus of the core amino acid sequence. In some embodiments, the ER export signal is linked to the core amino acid sequence by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal can comprise the amino acid sequence FXYENE (SEQ ID NO:30), where X can be any amino acid. In another embodiment, the ER export signal can comprise the amino acid sequence VXXSL, where X can be any amino acid. In some embodiments, the ER export signal can comprise the amino acid sequence FCYENEV (SEQ ID NO:31).

Endoplasmic reticulum (ER) export sequences that are suitable for use in a modified opsin of the present disclosure include, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (where X is any amino acid) (SEQ ID NO:30), e.g., FCYENEV (SEQ ID NO:31); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In other aspects, the light-responsive chloride pump proteins described herein can comprise a light-responsive protein expressed on the cell membrane, wherein the protein comprises a core amino acid sequence at least 75%, 85%, 90%, 91%, 92%, 93%, 94%, 95%, 96%, 97%, 98%, 99%, or 100% identical to the sequence shown in SEQ ID NO:16 and a trafficking signal (e.g., which can enhance transport of the light-responsive chloride pump protein to the plasma membrane). The trafficking signal may be fused to the C-terminus of the core amino acid sequence or may be fused to the N-terminus of the core amino acid sequence. In some embodiments, the trafficking signal can be linked to the core amino acid sequence by a linker which can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22).

In some aspects, the light-responsive chloride pump protein can comprise a core amino acid sequence at least 75%, 85%, 90%, 91%, 92%, 93%, 94%, 95%, 96%, 97%, 98%, 99%, or 100% identical to the sequence shown in SEQ ID NO:16 and at least one (such as one, two, three, or more) amino acid sequence motifs which enhance transport to the plasma membranes of mammalian cells selected from the group consisting of an ER export signal, a signal peptide, and a membrane trafficking signal. In some embodiments, the light-responsive chloride pump protein comprises an N-terminal signal peptide, a C-terminal ER Export signal, and a C-terminal trafficking signal. In some embodiments, the C-terminal ER Export signal and the C-terminal trafficking signal can be linked by a linker. The linker can comprise any of about 5, 10, 20, 30, 40, 50, 75, 100, 125, 150, 175, 200, 225, 250, 275, 300, 400, or 500 amino acids in length. The linker can also further comprise a fluorescent protein, for example, but not limited to, a yellow fluorescent protein, a red fluorescent protein, a green fluorescent protein, or a cyan fluorescent protein. In some embodiments the ER Export signal can be more C-terminally located than the trafficking signal. In other embodiments the trafficking signal is more C-terminally located than the ER Export signal. In some embodiments, the signal peptide comprises the amino acid sequence MTETLPPVTESAVALQAE (SEQ ID NO:32). In another embodiment, the light-responsive chloride pump protein comprises an amino acid sequence at least 95% identical to SEQ ID NO:17.

Moreover, in other aspects, the light-responsive chloride pump proteins can comprise a core amino acid sequence at least 75%, 85%, 90%, 91%, 92%, 93%, 94%, 95%, 96%, 97%, 98%, 99%, or 100% identical to the sequence shown in SEQ ID NO:16, wherein the N-terminal signal peptide of SEQ ID NO:16 is deleted or substituted. In some embodiments, other signal peptides (such as signal peptides from other opsins) can be used. The light-responsive protein can further comprise an ER transport signal and/or a membrane trafficking signal described herein. In some embodiments, the light-responsive chloride pump protein comprises an amino acid sequence at least 95% identical to SEQ ID NO:18.

In some embodiments, the light-responsive opsin protein is a NpHR opsin protein comprising an amino acid sequence at least 75%, at least 85%, at least 90%, at least 95%, at least 96%, at least 97%, at least 98%, at least 99% or 100% identical to the sequence shown in SEQ ID NO:16. In some embodiments, the NpHR opsin protein further comprises an endoplasmic reticulum (ER) export signal and/or a membrane trafficking signal. For example, the NpHR opsin protein comprises an amino acid sequence at least 95% identical to the sequence shown in SEQ ID NO:16 and an endoplasmic reticulum (ER) export signal. In some embodiments, the amino acid sequence at least 95% identical to the sequence shown in SEQ ID NO:16 is linked to the ER export signal through a linker. In some embodiments, the ER export signal comprises the amino acid sequence FXYENE (SEQ ID NO:30), where X can be any amino acid. In another embodiment, the ER export signal comprises the amino acid sequence VXXSL, where X can be any amino acid. In some embodiments, the ER export signal comprises the amino acid sequence FCYENEV (SEQ ID NO:31). In some embodiments, the NpHR opsin protein comprises an amino acid sequence at least 95% identical to the sequence shown in SEQ ID NO:16, an ER export signal, and a membrane trafficking signal. In other embodiments, the NpHR opsin protein comprises, from the N-terminus to the C-terminus, the amino acid sequence at least 95% identical to the sequence shown in SEQ ID NO:16, the ER export signal, and the membrane trafficking signal. In other embodiments, the NpHR opsin protein comprises, from the N-terminus to the C-terminus, the amino acid sequence at least 95% identical to the sequence shown in SEQ ID NO:16, the membrane trafficking signal, and the ER export signal. In some embodiments, the membrane trafficking signal is derived from the amino acid sequence of the human inward rectifier potassium channel Kir2.1. In some embodiments, the membrane trafficking signal comprises the amino acid sequence KSRITSEGEYIPLDQIDINV (SEQ ID NO:22). In some embodiments, the membrane trafficking signal is linked to the amino acid sequence at least 95% identical to the sequence shown in SEQ ID NO:16 by a linker. In some embodiments, the membrane trafficking signal is linked to the ER export signal through a linker. The linker may comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the light-responsive opsin protein further comprises an N-terminal signal peptide. In some embodiments, the light-responsive opsin protein comprises the amino acid sequence of SEQ ID NO:17. In some embodiments, the light-responsive opsin protein comprises the amino acid sequence of SEQ ID NO:18.

Also provided herein are polynucleotides encoding any of the light-responsive chloride ion pump proteins described herein, such as a light-responsive protein comprising a core amino acid sequence at least 75%, 85%, 90%, 91%, 92%, 93%, 94%, 95%, 96%, 97%, 98%, 99%, or 100% identical to the sequence shown in SEQ ID NO:16, an ER export signal, and a membrane trafficking signal. In another embodiment, the polynucleotides comprise a sequence which encodes an amino acid at least 95% identical to SEQ ID NO:17 and SEQ ID NO:18. The polynucleotides may be in an expression vector (such as, but not limited to, a viral vector described herein). The polynucleotides may be used for expression of the light-responsive chloride ion pump proteins.

Further disclosure related to light-responsive chloride pump proteins can be found in U.S. Patent Application Publication Nos: 2009/0093403 and 2010/0145418 as well as in International Patent Application No: PCT/US2011/028893, the disclosures of each of which are hereby incorporated by reference in their entireties.

*Dunaliella salina* Light-Activated Polypeptide

In some embodiments, a suitable light-responsive ion channel protein can be responsive to 470 nm-510 nm light and can be derived from *Dunaliella salina*, wherein the ion channel protein can be capable of mediating a hyperpolarizing current in the cell when the cell is illuminated with light. The light can have a wavelength between about 470 nm and about 510 nm or can have a wavelength of about 490 nm. In some embodiments, the light-responsive ion channel protein can comprise an amino acid sequence at least 75%, 85%, 90%, 91%, 92%, 93%, 94%, 95%, 96%, 97%, 98%, 99%, or 100% identical to the sequence shown in SEQ ID NO:15. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can contain one or more conservative amino acid substitutions and/or one or more non-conservative amino acid substitutions. The light-responsive ion channel protein comprising substitutions, deletions, and/or insertions introduced into the native amino acid sequence suitably retains the ability to transport ions across the plasma membrane of a neuronal cell in response to light.

In other aspects of the methods disclosed herein, the light-responsive ion channel protein can comprise a core amino acid sequence at least 75%, 85%, 90%, 91%, 92%, 93%, 94%, 95%, 96%, 97%, 98%, 99%, or 100% identical to the sequence shown in SEQ ID NO:15 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton ion channel comprises an N-terminal signal peptide and a C-terminal ER export signal. In some embodiments, the light-responsive ion channel protein comprises an N-terminal signal peptide and a C-terminal trafficking signal. In some embodiments, the light-responsive ion channel protein comprises an N-terminal signal peptide, a C-terminal ER Export signal, and a C-terminal trafficking signal. In some embodiments, the light-responsive ion channel protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the light-responsive channel proteins described herein, such as a light-responsive ion channel protein comprising a core amino acid sequence at least 85%, 90%, 91%, 92%, 93%, 94%, 95%, 96%, 97%, 98%, 99%, or 100% identical to the sequence shown in SEQ ID NO:15. Also provided herein are expression vectors (such as a viral vector described herein) comprising a polynucleotide encoding the proteins described herein, such as a light-responsive channel protein comprising a core amino acid sequence at least 85%, 90%, 91%, 92%, 93%, 94%, 95%, 96%, 97%, 98%, 99%, or 100% identical to the sequence shown in SEQ ID NO:15.

Polynucleotides and Vectors

As discussed above, methods for controlling pain according to the present disclosure generally involve introducing into a neuron (e.g., a nociceptor) of an individual a nucleic acid comprising a nucleotide sequence encoding an opsin that provides for hyperpolarization of the cell in response to light of a wavelength that activates the opsin. Suitable nucleic acids comprise a nucleotide sequence that encodes one or more of the light-activated polypeptides (opsins) described herein (e.g., one or more light-activated polypeptides as described herein). In some embodiments, a polynucleotide comprises an expression cassette, wherein the expression cassette contains a plurality of components (e.g., coding sequences; transcription control sequences; etc.) that are utilized to express one or more proteins encoded by the polynucleotide in a target cell.

In some embodiments, a portion of a polynucleotide encoding a light-activated polypeptide is operably linked to a promoter sequence. Any suitable promoter that functions in a target cell can be used for expression of a polynucleotide encoding a light-activated polypeptide. In certain embodiments, a promoter sequence can be a promoter that is specific to a particular target cell type or to a particular tissue type, such as a particular neuron or a pan-neuronal promoter. Initiation control regions of promoters, which are useful to drive expression of polynucleotides in a specific animal cell, are numerous and familiar to those skilled in the art. Virtually any promoter capable of driving expression of the subject polynucleotides can be used. In some embodiments, the promoter used to drive expression of a subject protein can be the Thy1 promoter (See, e.g., Llewellyn, et al., 2010, Nat. Med., 16(10):1161-1166). In some embodiments, the promoter used to drive expression of a subject protein can be a human synapsin (hSyn) promoter, a human elongation factor 1-α (EF1α) promoter, a cytomegalovirus (CMV) promoter, a CMV early enhancer/chicken β actin (CAG) promoter, a synapsin-I promoter (e.g., a human synapsin-I promoter), a human synuclein 1 promoter, a human Thy1 promoter, a calcium/calmodulin-dependent kinase II alpha (CAMKIIα) promoter, or any other promoter capable of driving expression of the a subject nucleic acid sequence in a target cell.

Neuron-specific promoters and other control elements (e.g., enhancers) are known in the art, and can be operably linked to an opsin-encoding nucleotide sequence. Suitable neuron-specific control sequences include, but are not limited to, a neuron-specific enolase (NSE) promoter (see, e.g., EMBL HSENO2, X51956; see also, e.g., U.S. Pat. No. 6,649,811, 5,387,742); an aromatic amino acid decarboxylase (AADC) promoter; a neurofilament promoter (see, e.g., GenBank HUMNFL, L04147); a synapsin promoter (see, e.g., GenBank HUMSYNIB, M55301); a thy-1 promoter (see, e.g., Chen et al. (1987) Cell 51:7-19); a serotonin receptor promoter (see, e.g., GenBank S62283); a tyrosine hydroxylase promoter (TH) (see, e.g., Nucl. Acids. Res. 15:2363-2384 (1987) and Neuron 6:583-594 (1991)); a GnRH promoter (see, e.g., Radovick et al., Proc. Natl. Acad. Sci. USA 88:3402-3406 (1991)); an L7 promoter (see, e.g., Oberdick et al., Science 248:223-226 (1990)); a DNMT promoter (see, e.g., Bartge et al., Proc. Natl. Acad. Sci. USA 85:3648-3652 (1988)); an enkephalin promoter (see, e.g., Comb et al., EMBO J. 17:3793-3805 (1988)); a myelin basic protein (MBP) promoter; a CMV enhancer/platelet-derived growth factor-β promoter (see, e.g., Liu et al. (2004) *Gene Therapy* 11:52-60); a motor neuron-specific gene Hb9 promoter (see, e.g., U.S. Pat. No. 7,632,679; and Lee et al. (2004) *Development* 131:3295-3306); and an alpha subunit of $Ca^{2+}$-calmodulin-dependent protein kinase II (CaMKIIα) promoter (see, e.g., Mayford et al. (1996) *Proc. Natl. Acad. Sci. USA* 93:13250).

In some embodiments, a promoter may be an inducible promoter. For example, the promoter may be induced by a trans-acting factor that responds to an exogenously administered drug. Examples of inducible promoters include, but are not limited to, tetracycline-on or tetracycline-off promoters, or tamoxifen-inducible CreER.

In some embodiments, a subject polynucleotide may comprise a ribosomal skip sequence that can be used to generate two separate proteins from the same transcript. In such embodiments, a subject polynucleotide will typically include a coding sequence that encodes a light-activated protein as well as a response protein. In these embodiments, a ribosomal skip sequence may be placed between the two coding sequences to produce two distinct proteins (namely, the light-activated protein and the response protein) from the same transcript.

As noted above, in some cases, the nucleic acid is a recombinant expression vector comprising a nucleotide sequence encoding a light-activated polypeptide or any variant thereof as described herein. Suitable expression vectors include vectors comprising a nucleotide sequence that encodes an RNA (e.g., an mRNA) that when transcribed from the polynucleotides of the vector will result in the accumulation of a subject protein on the plasma membranes of target cells. Vectors which may be used include, without limitation, lentiviral, herpes simplex virus, adenoviral, and adeno-associated virus (AAV) vectors. Lentiviral vectors include, but are not limited to human immunodeficiency virus (HIV)-based vectors. Lentiviral vectors may be pseudotyped with the envelope proteins of other viruses, including, but not limited to vesicular stomatitis virus (VSV), rabies, Mo-murine leukemia virus (MLV), baculovirus and Ebola. Such vectors may be prepared using standard methods in the art.

In some embodiments, a vector may be a recombinant AAV vector. AAV vectors are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome that contains the rep gene involved in viral replication and expression of the viral genes; and the right-hand part of the genome that contains the cap gene encoding the capsid proteins of the virus.

AAV vectors may be prepared using standard methods in the art. Adeno-associated viruses of any serotype are suitable (see, e.g., Blacklow, pp. 165-174 of "Parvoviruses and Human Disease" J. R. Pattison, ed. (1988); Rose, Comprehensive Virology 3:1, 1974; P. Tattersall "The Evolution of Parvovirus Taxonomy" In Parvoviruses (J R Kerr, S F Cotmore, M E Bloom, R M Linden, C R Parrish, Eds.) p 5-14, Hudder Arnold, London, UK (2006); and D E Bowles, S E Rabinowitz, R J Samulski "The Genus Dependovirus" (J R Kerr, S F Cotmore, M E Bloom, R M Linden, C R Parrish, Eds.) p 15-23, Hudder Arnold, London, UK (2006), the disclosures of each of which are hereby incorporated by reference herein in their entireties). Methods for purifying for vectors may be found in, for example, U.S. Pat. Nos. 6,566,118, 6,989,264, and 6,995,006 and WO/1999/011764 titled "Methods for Generating High Titer Helper-free Preparation of Recombinant AAV Vectors", the disclosures of which are herein incorporated by reference in their entirety. Methods of preparing AAV vectors in a baculovirus system are described in, e.g., WO 2008/024998. AAV vectors can be self-complementary or single-stranded. Preparation of hybrid vectors is described in, for example, PCT Application No. PCT/US2005/027091, the disclosure of which is herein incorporated by reference in its entirety. The use of vectors derived from the AAVs for transferring genes in vitro and in vivo has been described (See e.g., International Patent Application Publication Nos.: 91/18088 and WO 93/09239; U.S. Pat. Nos. 4,797,368, 6,596,535, and 5,139,941; and European Patent No.: 0488528, all of which are hereby incorporated by reference herein in their entireties). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication-defective recombinant AAVs according to the present disclosure can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In some embodiments, the vector(s) for use in the methods of the present disclosure are encapsidated into a virus particle (e.g. AAV virus particle including, but not limited to, AAV1, AAV2, AAV3, AAV4, AAV5, AAV6, AAV7, AAV8, AAV9, AAV10, AAV11, AAV12, AAV13, AAV14, AAV15, and AAV16). Accordingly, the present disclosure includes a recombinant virus particle (recombinant because it contains a recombinant polynucleotide) comprising any of the vectors described herein. Methods of producing such particles are known in the art and are described in U.S. Pat. No. 6,596, 535, the disclosure of which is hereby incorporated by reference in its entirety. In some cases, AAV6 is used. In some cases, AAV1 is used.

Pharmaceutical Compositions

Aspects of the present disclosure include pharmaceutical compositions that polynucleotides, vectors, or components thereof, described above. The subject pharmaceutical compositions may be administered to a subject for purposes of genetically modifying a target cell so that the target cell expresses one or more light-activated proteins. A subject pharmaceutical composition may, in some embodiments, comprise a pharmaceutically acceptable excipient. In some embodiments, a pharmaceutical composition may comprise components to facilitate delivery of the subject polynucleotides or vectors to a target cell, including but not limited to transfection reagents or components thereof, such as lipids, polymers, and the like.

In some embodiments, a subject pharmaceutical composition will be suitable for injection into a subject, e.g., will be sterile. For example, in some embodiments, a subject pharmaceutical composition will be suitable for injection into a subject, e.g., where the composition is sterile and is free of detectable pyrogens and/or other toxins.

Pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public as well, and may be incorporated into the pharmaceutical compositions of the present disclosure without limitation.

Delivery Devices

In some cases, a delivery device is used to deliver a nucleic acid encoding a light-activated polypeptide, or a pharmaceutical composition comprising same, to a target cell. The delivery device may provide regular, irregular, programmed, or clinician- or patient-activated doses of the nucleic acid or pharmaceutical composition to one or more target cells to ensure that the target cells continue to express the encoded light-activated polypeptide.

Suitable delivery devices may generally include one or more components, such as reservoirs, pumps, actuators, tubing components, needles, catheters, and any other suitable components for delivering the nucleic acid or pharmaceutical composition to a target cell or tissue of an individual. Delivery devices may also include components that facilitate computerized operation, such as a power source, a processor comprising a memory, a user input device, and/or a graphical user interface. In some embodiments, a delivery device may be completely or partially implantable within a patient. In some embodiments, a delivery device may be operated by a caregiver, wherein the device is introduced into a portion of the patient's body, e.g., into the patient's brain, and a subject pharmaceutical composition is delivered to a target tissue, e.g., a portion of the patient's brain. In some embodiments, following delivery of the pharmaceutical composition, the device may be removed. In other embodiments, the device may be kept in place for later delivery of additional pharmaceutical compositions.

Light-Generating Devices

In carrying out a subject method of controlling pain, a light-generating device can be used to deliver light to target cells that express one or more light-activated polypeptides. Light-generating devices suitable for use with a method of the present disclosure can generally produce light of a variety of different wavelengths from one or more light sources on the device. In some embodiments, a light-generating device may include a light cuff or sleeve that can be placed around or near target cells expressing one or more subject proteins. In some embodiments, a portion of the light source or the entire light source may be implantable. The subject light-generating devices may be of any useful configuration for stimulating the light-activated proteins disclosed herein. In some embodiments, for example, a light-generating device may comprise components that facilitate exclusive illumination of a target cell or tissue. For example, in some embodiments, a light-generating device may exclusively direct light to a target cell, a portion of a target cell, e.g., a particular axon of a nerve cell, or a specific anatomical structure, such as, e.g. a bundle of nerve fibers, a target tissue, or a portion of the spinal cord. By "exclusively direct light" is meant that the light-generating device only delivers light to the specific target structure, and does not illuminate other structures. For examples, in some embodiments, a light-generating device may be configured to illuminate an axon of a nerve cell, but not illuminate any other portion of the nerve cell. In this way, the light from the light-generating device only affects light-activated proteins in the specific target structure that is illuminated.

In some embodiments, a light-generating device may not completely surround the region containing a target cell expressing a light-activated protein, but, rather, can have a U-shape. In some embodiments, a light-generating device can have an attachment arm that can be used to guide the light-generating device to a specific region or target structure, e.g., a specific neuronal region. The attachment arm can be removed following implantation of the light-generating device or can be left in place to fix the position of the light-generating device in proximity to the target cells of interest.

In some embodiments, the subject light-generating devices may comprise an inner body, the inner body having at least one means for generating light which is connected to a power source. In some embodiments, the power source can be an internal battery for powering the light-generating device. In some embodiments, an implantable light-generating device may comprise an external antenna for receiving wirelessly transmitted electromagnetic energy from an external source for powering device. The wirelessly transmitted electromagnetic energy can be a radio wave, a microwave, or any other electromagnetic energy source that can be transmitted from an external source to power the light-generating device. In some embodiments, the light-generating device is controlled by, e.g., an integrated circuit produced using semiconductor or other processes known in the art.

In some embodiments, the light-generating device may comprise a light emitting diode (LED). In some embodiments, the LED can generate blue and/or green light. In other embodiments, the LED can generate amber and/or yellow light. In some embodiments, several micro LEDs are embedded into the inner body of the light-generating device. In other embodiments, the light-generating device is a solid state laser diode or any other means capable of generating light. The light-generating device can generate light having a wavelength and intensity sufficient to activate a subject light-activated protein. In some embodiments, a light-generating device produces light having an intensity of any of about 0.05 mW/mm$^2$, 0.1 mW/mm$^2$, 0.2 mW/mm$^2$, 0.3 mW/mm$^2$, 0.4 mW/mm$^2$, 0.5 mW/mm$^2$, about 0.6 mW/mm$^2$, about 0.7 mW/mm$^2$, about 0.8 mW/mm$^2$, about 0.9 mW/mm$^2$, about 1.0 mW/mm$^2$, about 1.1 mW/mm$^2$, about 1.2 mW/mm$^2$, about 1.3 mW/mm$^2$, about 1.4 mW/mm$^2$, about 1.5 mW/mm$^2$, about 1.6 mW/mm$^2$, about 1.7 mW/mm$^2$, about 1.8 mW/mm$^2$, about 1.9 mW/mm$^2$, about 2.0 mW/mm$^2$, about 2.1 mW/mm$^2$, about 2.2 mW/mm$^2$, about 2.3 mW/mm$^2$, about 2.4 mW/mm$^2$, about 2.5 mW/mm$^2$, about 3 mW/mm$^2$, about 3.5 mW/mm$^2$, about 4 mW/mm$^2$, about 4.5 mW/mm$^2$, about 5 mW/mm$^2$, about 5.5 mW/mm$^2$, about 6 mW/mm$^2$, about 7 mW/mm$^2$, about 8 mW/mm$^2$, about 9 mW/mm$^2$, or about 10 mW/mm$^2$, inclusive, including values in between these numbers. In some embodiments, the light-generating device produces light having an intensity of at least about 10 Hz, such as up to about 25 Hz, such as up to about 50 Hz, such as up to about 75 Hz, such as up to about 100 Hz.

Suitable light-generating devices are generally capable of generating light having a wavelength ranging from about 350 nm, up to about 360 nm, up to about 370 nm, up to about 380 nm, up to about 390 nm, up to about 400 nm, up to about 410 nm, up to about 420 nm, up to about 430 nm, up to about 440 nm, up to about 450 nm, up to about 460 nm, up to about 470 nm, up to about 480 nm, up to about 490 nm, up to about 500 nm, up to about 510 nm, up to about 520 nm, up to about 530 nm, up to about 540 nm, up to about 550 nm, up to about 560 nm, up to about 570 nm, up to about 580 nm, up to about 590 nm, up to about 600 nm, up to about 610 nm, up to about 620 nm, up to about 630 nm, up to about 640 nm, up to about 650 nm, up to about 660 nm, up to about 670 nm, up to about 680 nm, up to about 690 nm, up to about 700 nm, up to about 710 nm, up to about 720 nm, up to about 730 nm, up to about 740 nm, and/or up to about 750 nm.

In some embodiments, a suitable light-generating device may include one or more optical fibers that can transmit light from a light source and deliver the light to a target structure. The optical fibers may comprise plastic or glass materials, and in some embodiments may be suitably flexible to facilitate placement of the light-generating device in locations that could not be accommodated by rigid structures. For example, in some embodiments, a light-generating device may comprise a light source that generates light, as well as one or more optical fibers that can be placed in various locations on or in the patient's body. Light from the light source can pass through the optical fiber, passing around corners and bends in the optical fiber, and emerge at the end of the optical fiber to deliver light to a target structure.

In some embodiments, a suitable light-generating device may comprise a plurality of light sources that can be used to illuminate a target tissue with different wavelengths of light. For example, in some embodiments, a light-generating device may comprise a first light source that generates light of a first wavelength, e.g., red light, and a second light source that generates light of a second wavelength, e.g., green light. Such light-generating devices may be used to simultaneously illuminate the same target tissue with light of both wavelengths, or may alternately illuminate the target tissue with light of the first wavelength and light of the second wavelength. In some embodiments, such light generating devices may be used to deliver light from the same light source different target tissues. For example, in some embodiments a light-generating device may deliver light of a first wavelength to a first target tissue, and may deliver light of a second wavelength to a different target tissue.

Control Devices

In some cases, a control device that can control, or modulate, the amount of light that is emitted from the light-generating device is used in a subject method. In some embodiments, a control device may be configured to modulate the wavelength and/or the intensity of light that is delivered to a target tissue from a light-generating device. In some embodiments, a control device may be configured to modulate the frequency and/or duration of light that is delivered to a target tissue from a light-generating device. For example, in some embodiments, a control device may be configured to deliver pulses of light from the light-generating device to a target tissue. The control device can modulate the frequency and/or duration of the light pulses such that the target tissue is illuminated with light from the light-generating device, e.g., at a regular or irregular rate, according to a user input, etc. In some embodiments, a control device can produce pulses of light from the light-generating device that have a duration ranging from about 1 millisecond or less, up to about 1 second, up to about 10 seconds, up to about 20 seconds, up to about 30 seconds, up to about 40 seconds, up to about 50 seconds, up to about 60 seconds or more. In some embodiments, a control device can produce pulses of light from the light-generating device that have a frequency of 1 pulse per millisecond, up to about 1 pulse per second, up about 1 pulse per minute, up to about 1 pulse per 10 minutes, up to about 1 pulse per 20 minutes, up to about 1 pulse per 30 minutes.

In some embodiments, a suitable control device may comprise a power source that can be mounted to a wireless transmitter. In some embodiments, a suitable control device may comprise a power source that can be mounted to a transmitting coil. In some embodiments, a battery can be connected to the power source for providing power thereto. A switch can be connected to the power source, allowing an operator (e.g., a patient or caregiver) to manually activate or deactivate the power source. In some embodiments, upon activation of the switch, the power source can provide power to the light-generating device through electromagnetic coupling between the transmitting coil on the control device and an antenna (which may be an external antenna or an internal antenna) of an implantable light-generating device (such as a light cuff or sleeve). The transmitting coil can establish an electromagnetic coupling with the external antenna of the implantable light-generating device when in proximity thereof, for supplying power to the light-generating device and for transmitting one or more control signals to the light-generating device. In some embodiments, the electromagnetic coupling between the transmitting coil of the control device and the external antenna of the implantable light-generating device can be radio-frequency magnetic inductance coupling. When radio-frequency magnetic inductance coupling is used, the operational frequency of the radio wave can be between about 1 and 20 MHz, inclusive, including any values in between these numbers (for example, about 1 MHz, about 2 MHz, about 3 MHz, about 4 MHz, about 5 MHz, about 6 MHz, about 7 MHz, about 8 MHz, about 9 MHz, about 10 MHz, about 11 MHz, about 12 MHz, about 13 MHz, about 14 MHz, about 15 MHz, about 16 MHz, about 17 MHz, about 18 MHz, about 19 MHz, or about 20 MHz). In some cases, the operational frequency of the radio wave can be between about 20 MHz and 5 GHz, e.g., from about 20 MHz to about 50 MHz, from about 50 MHz to about 250 MHz, from about 250 MHz to about 500 MHz, from about 500 MHz to about 750 MHz, from about 750 MHz to about 1 GHz, from about 1 GHz to about 2 GHz, from about 2 GHz to about 3 GHz, from about 3 GHz to about 4 GHz, or from about 4 GHz to about 5 GHz. For example, where midfield radiofrequency coupling is used, the operational frequency can be from 690 MHz to 2.2 GHz. Other coupling techniques may be used, such as an optical receiver, infrared, or a biomedical telemetry system (See, e.g., Kiourti, "Biomedical Telemetry: Communication between Implanted Devices and the External World, Opticon 1826, (8): Spring, 2010).

Non-Human Animal Model of Pain

The present disclosure provides a non-human animal model of nociceptive pain, where the non-human animal expresses in a neuron (e.g., a primary afferent neuron, such as a small- or a large-diameter primary afferent neuron; e.g., a nociceptor) of the animal a nucleic acid comprising a nucleotide sequence encoding an opsin polypeptide that provides for depolarization of the nociceptor in response to light of a wavelength that activates the opsin. Illumination of the depolarizing opsin, expressed in a membrane of the neuron (e.g., primary afferent neuron, such as a small- or a large-diameter primary afferent neuron; e.g., nociceptor) in the non-human animal, induces pain in the animal.

A subject non-human animal model is useful for identifying agents that control pain (as described below). A subject non-human animal model is useful for research applications, e.g., to investigate the role of nociceptor activity in the genesis of pain (e.g., neuropathic pain). In some cases, a subject non-human animal model of pain is a rat. In some cases, a subject non-human animal model of pain is a mouse.

In some embodiments, the non-human animal model is not a transgenic animal, e.g., the non-human animal model does not include a nucleic acid encoding a light-activated polypeptide integrated into the genome of a germ cell. In some embodiments, the non-human animal model comprises a nucleic acid encoding a light-activated polypeptide in a primary afferent neuron, such as a nociceptor, where the nucleic acid may be integrated into the genome of the primary afferent neuron (e.g., nociceptor). In some embodiments, the non-human animal model comprises a nucleic acid encoding a light-activated polypeptide in a primary afferent neuron (e.g., nociceptor), and not in a non-neuronal cell, where the nucleic acid is integrated into the genome of the nociceptor. In some embodiments, the non-human animal model comprises a nucleic acid encoding a light-activated polypeptide in a primary afferent neuron (e.g., nociceptor), and not in a non-neuronal cell of the animal, where the nucleic acid is not integrated into the genome of the nociceptor.

In some cases, a Cre-dependent DIO-AAV6 construct (see, e.g., Sohal et al. (2009) Nature 459:698) comprising a nucleotide sequence encoding a depolarizing light-activated polypeptide can be used with a nociceptor-specific Cre mouse line, to achieve opsin expression restricted to subpopulations of nociceptors. For example, a nucleotide sequence encoding a depolarizing light-responsive polypeptide is included within a Cre-dependent DIO-AAV6 construct; and the construct is introduced into nociceptors in a nociceptor-specific Cre mouse.

Depolarizing Light-Activated Proteins

As discussed above, a subject non-human animal model of pain expresses in a neuron (e.g., a primary afferent neuron, such as a small- or a large-diameter primary afferent neuron; e.g., a nociceptor) of the animal a nucleic acid comprising a nucleotide sequence encoding an opsin polypeptide that provides for depolarization of the nociceptor in response to light of a wavelength that activates the opsin.

Examples of suitable light-responsive polypeptides include, e.g., members of the Channelrhodopsin family of light-responsive cation channel proteins such as *Chlamydomonas rheinhardtii* channelrhodopsin 2 (ChR2); a step-function opsin (SFO); a stabilized SFO (SSFO); a chimeric opsin such as C1V1; a *Volvox carteri*-derived channelrhodopsin (VChR1), etc. Such light-responsive polypeptides can be used to promote neural cell membrane depolarization in response to a light stimulus.

Enhanced Intracellular Transport Amino Acid Motifs

Light-responsive opsin proteins having components derived from evolutionarily simpler organisms may not be expressed or tolerated by mammalian cells or may exhibit impaired subcellular localization when expressed at high levels in mammalian cells. Consequently, in some embodiments, the light-responsive opsin proteins expressed in a cell can be fused to one or more amino acid sequence motifs selected from the group consisting of a signal peptide, an endoplasmic reticulum (ER) export signal, a membrane trafficking signal, and/or an N-terminal golgi export signal. The one or more amino acid sequence motifs which enhance light-responsive protein transport to the plasma membranes of mammalian cells can be fused: a) to the N-terminus of the light-responsive protein; b) to the C-terminus of the light-responsive protein; c) to both the N- and C-terminal ends of the light-responsive protein; or d) internally within the light-responsive protein. Optionally, the light-responsive protein and the one or more amino acid sequence motifs may be separated by a linker.

In some embodiments, the light-responsive protein can be modified by the addition of a trafficking signal (ts) which enhances transport of the protein to the cell plasma membrane. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)).

A trafficking sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Signal sequences that are suitable for inclusion in a light-activated polypeptide can comprise an amino acid sequence having at least 85%, 90%, 91%, 92%, 93%, 94%, 95%, 96%, 97%, 98%, 99%, or 100%, amino acid sequence identity to an amino acid sequence such as one of the following:

1) the signal peptide of hChR2 (e.g., MDYGGAL-SAVGRELLFVTNPVVVNGS (SEQ ID NO:23))

2) the β2 subunit signal peptide of the neuronal nicotinic acetylcholine receptor (e.g., MAGHSNSMALFSFSLL-WLCSGVLGTEF (SEQ ID NO:24));

3) a nicotinic acetylcholine receptor signal sequence (e.g., MGLRALMLWLLAAAGLVRESLQG (SEQ ID NO:25)); and 4) a nicotinic acetylcholine receptor signal sequence (e.g., MRGTPLLLVVSLFSLLQD (SEQ ID NO:26)).

A signal sequence can have a length of from about 10 amino acids to about 50 amino acids, e.g., from about 10 amino acids to about 20 amino acids, from about 20 amino acids to about 30 amino acids, from about 30 amino acids to about 40 amino acids, or from about 40 amino acids to about 50 amino acids.

Endoplasmic reticulum (ER) export sequences that are suitable for use in a light-responsive polypeptide include, e.g., VXXSL (where X is any amino acid) (e.g., VKESL (SEQ ID NO:27); VLGSL (SEQ ID NO:28); etc.); NANS-FCYENEVALTSK (SEQ ID NO:29); FXYENE (SEQ ID NO:30) (where X is any amino acid), e.g., FCYENEV (SEQ ID NO:31); and the like. An ER export sequence can have a length of from about 5 amino acids to about 25 amino acids, e.g., from about 5 amino acids to about 10 amino acids, from about 10 amino acids to about 15 amino acids, from about 15 amino acids to about 20 amino acids, or from about 20 amino acids to about 25 amino acids.

In some embodiments, the native signal peptide sequence in the protein can be deleted or substituted with a heterologous signal peptide sequence from a different protein.

ChR

In some aspects, the light-responsive cation channel protein can be derived from *Chlamydomonas reinhardtii*, wherein the cation channel protein can be capable of transporting cations across a cell membrane when the cell is illuminated with light. In another embodiment, the light-responsive cation channel protein can comprise an amino acid sequence at least 75%, 85%, 90%, 91%, 92%, 93%, 94%, 95%, 96%, 97%, 98%, 99%, or 100% identical to the sequence shown in SEQ ID NO:8. The light used to activate the light-responsive cation channel protein derived from *Chlamydomonas reinhardtii* can have a wavelength between about 460 and about 495 nm or can have a wavelength of about 480 nm. Additionally, light pulses having a temporal frequency of about 100 Hz can be used to activate the light-responsive protein. In some embodiments, activation of the light-responsive cation channel derived from *Chlamydomonas reinhardtii* with light pulses having a temporal frequency of about 100 Hz can cause depolarization of the neurons expressing the light-responsive cation channel. The light-responsive cation channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive cation channel protein to regulate the polarization state of the plasma membrane of the cell. Additionally, the light-responsive cation channel protein can contain one or more conservative amino acid substitutions and/or one or more non-conservative amino acid substitutions. The light-responsive proton pump protein comprising substitutions, deletions, and/or insertions introduced into the native amino acid sequence suitably retains the ability to transport cations across a cell membrane.

In some embodiments, the light-responsive cation channel comprises a T159C substitution of the amino acid sequence set forth in SEQ ID NO:8. In some embodiments, the light-responsive cation channel comprises a L132C substitution of the amino acid sequence set forth in SEQ ID NO:8. In some embodiments, the light-responsive cation channel comprises an E123T substitution of the amino acid sequence set forth in SEQ ID NO:8. In some embodiments, the light-responsive cation channel comprises an E123A substitution of the amino acid sequence set forth in SEQ ID NO:8. In some embodiments, the light-responsive cation channel comprises a T159C substitution and an E123T substitution of the amino acid sequence set forth in SEQ ID NO:8. In some embodiments, the light-responsive cation channel comprises a T159C substitution and an E123A substitution of the amino acid sequence set forth in SEQ ID NO:8. In some embodiments, the light-responsive cation channel comprises a T159C substitution, an L132C substitution, and an E123T substitution of the amino acid sequence set forth in SEQ ID NO:8. In some embodiments, the light-responsive cation channel comprises a T159C substitution, an L132C substitution, and an E123A substitution of the amino acid sequence set forth in SEQ ID NO:8. In some embodiments, the light-responsive cation channel comprises an L132C substitution and an E123T substitution of the amino acid sequence set forth in SEQ ID NO:8. In some embodiments, the light-responsive cation channel comprises an L132C substitution and an E123A substitution of the amino acid sequence set forth in SEQ ID NO:8.

In some embodiments, a ChR2 protein comprises at least one (such as one, two, three, or more) amino acid sequence motifs that enhance transport to the plasma membranes of target cells selected from the group consisting of a signal peptide, an ER export signal, and a membrane trafficking signal. In some embodiments, the ChR2 protein comprises an N-terminal signal peptide and a C-terminal ER export signal. In some embodiments, the ChR2 protein comprises an N-terminal signal peptide and a C-terminal trafficking signal. In some embodiments, the ChR2 protein comprises an N-terminal signal peptide, a C-terminal ER export signal, and a C-terminal trafficking signal. In some embodiments, the ChR2 protein comprises a C-terminal ER export signal and a C-terminal trafficking signal. In some embodiments, the C-terminal ER export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)).

In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

Step Function Opsins and Stabilized Step Function Opsins Based on ChR2

In other embodiments, the light-responsive polypeptide is a step function opsin (SFO) protein or a stabilized step function opsin (SSFO) protein that can have specific amino acid substitutions at key positions in the retinal binding pocket of the protein. In some embodiments, the SFO protein can have a mutation at amino acid residue C128 of SEQ ID NO:8. In other embodiments, the SFO protein has a C128A mutation in SEQ ID NO:8. In other embodiments, the SFO protein has a C128S mutation in SEQ ID NO:8. In another embodiment, the SFO protein has a C128T mutation in SEQ ID NO:8. In some embodiments, the SFO protein can comprise an amino acid sequence at least 75%, 85%, 90%, 91%, 92%, 93%, 94%, 95%, 96%, 97%, 98%, 99%, or 100% identical to the sequence shown in SEQ ID NO:9, and comprises an alanine, serine, or threonine at amino acid 128.

In some embodiments, the SSFO protein can have a mutation at amino acid residue D156 of SEQ ID NO:8. In other embodiments, the SSFO protein can have a mutation at both amino acid residues C128 and D156 of SEQ ID NO:8. In one embodiment, the SSFO protein has an C128S and a D156A mutation in SEQ ID NO:8. In another embodiment, the SSFO protein can comprise an amino acid sequence at least 75%, 85%, 90%, 91%, 92%, 93%, 94%, 95%, 96%, 97%, 98%, 99%, or 100% identical to the sequence shown in SEQ ID NO:10; and comprises an alanine, serine, or threonine at amino acid 128; and comprises a alanine at amino acid 156. In another embodiment, the SSFO protein can comprise a C128T mutation in SEQ ID NO:8. In some embodiments, the SSFO protein comprises C128T and D156A mutations in SEQ ID NO:8.

In some embodiments the SFO or SSFO proteins provided herein can be capable of mediating a depolarizing current in the cell when the cell is illuminated with blue light. In other embodiments, the light can have a wavelength of about 445 nm. Additionally, in some embodiments the light can be delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

Further disclosure related to SFO or SSFO proteins can be found in International Patent Application Publication No. WO 2010/056970, the disclosure of which is hereby incorporated by reference in its entirety.

In some cases, the ChR2-based SFO or SSFO comprises a membrane trafficking signal and/or an ER export signal. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

C1V1 Chimeric Cation Channels

In other embodiments, the light-responsive cation channel protein can be a C1V1 chimeric protein derived from the VChR1 protein of *Volvox carteri* and the ChR1 protein from *Chlamydomonas reinhardti*, wherein the protein comprises the amino acid sequence of VChR1 having at least the first and second transmembrane helices replaced by the first and second transmembrane helices of ChR1; is responsive to light; and is capable of mediating a depolarizing current in the cell when the cell is illuminated with light. In some embodiments, the C1V1 protein can further comprise a replacement within the intracellular loop domain located between the second and third transmembrane helices of the chimeric light responsive protein, wherein at least a portion of the intracellular loop domain is replaced by the corresponding portion from ChR1. In another embodiment, the portion of the intracellular loop domain of the C1V1 chimeric protein can be replaced with the corresponding portion from ChR1 extending to amino acid residue A145 of the ChR1. In other embodiments, the C1V1 chimeric protein can further comprise a replacement within the third transmembrane helix of the chimeric light responsive protein, wherein at least a portion of the third transmembrane helix is replaced by the corresponding sequence of ChR1. In yet another embodiment, the portion of the intracellular loop domain of the C1V1 chimeric protein can be replaced with the corresponding portion from ChR1 extending to amino acid residue W163 of the ChR1. In other embodiments, the C1V1 chimeric protein can comprise an amino acid sequence at least 75%, 85%, 90%, 91%, 92%, 93%, 94%, 95%, 96%, 97%, 98%, 99%, or 100% identical to the sequence shown in SEQ ID NO:11.

In some embodiments, the C1V1 protein can mediate a depolarizing current in the cell when the cell is illuminated with green light. In other embodiments, the light can have a wavelength of between about 540 nm to about 560 nm. In some embodiments, the light can have a wavelength of about 542 nm. In some embodiments, the C1V1 chimeric protein is not capable of mediating a depolarizing current in the cell when the cell is illuminated with violet light. In some embodiments, the chimeric protein is not capable of mediating a depolarizing current in the cell when the cell is illuminated with light having a wavelength of about 405 nm. Additionally, in some embodiments, light pulses having a temporal frequency of about 100 Hz can be used to activate the C1V1 protein.

In some cases, the C1V1 polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

C1V1 Variants

In some aspects, a suitable light-responsive polypeptide comprises substituted or mutated amino acid sequences, wherein the mutant polypeptide retains the characteristic light-activatable nature of the precursor C1V1 chimeric polypeptide but may also possess altered properties in some specific aspects. For example, the mutant light-responsive C1V1 chimeric proteins described herein can exhibit an increased level of expression both within an animal cell or on the animal cell plasma membrane; an altered responsiveness when exposed to different wavelengths of light, particularly red light; and/or a combination of traits whereby the chimeric C1V1 polypeptide possess the properties of low desensitization, fast deactivation, low violet-light activation for minimal cross-activation with other light-responsive cation channels, and/or strong expression in animal cells.

Accordingly, provided herein are C1V1 chimeric light-responsive opsin proteins that can have specific amino acid substitutions at key positions throughout the retinal binding pocket of the VChR1 portion of the chimeric polypeptide. In some embodiments, the C1V1 protein can have an amino acid substitution at amino acid residue E122 of SEQ ID NO:11. In some embodiments, the C1V1 protein can have a substitution at amino acid residue E162 of SEQ ID NO:11. In other embodiments, the C1V1 protein can have a substitution at both amino acid residues E162 and E122 of SEQ ID NO:11. In other embodiments, the C1V1 protein can comprise an amino acid sequence at least 75%, 85%, 90%, 91%, 92%, 93%, 94%, 95%, 96%, 97%, 98%, 99%, or 100% identical to the sequence shown in SEQ ID NO:12, SEQ ID NO:13, or SEQ ID NO:14; and can include one or more of the aforementioned amino acid substitutions.

In some aspects, the C1V1-E122 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In other embodiments, the C1V1-E122 mutant chimeric protein can mediate a depolarizing current in the cell when the cell is illuminated with red light. In some embodiments, the red light can have a wavelength of about 630 nm. In some embodiments, the C1V1-E122 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E122 mutant chimeric protein. In some embodiments, activation of the C1V1-E122 mutant chimeric protein with light pulses having a frequency of 100 Hz can cause depolarization of the neurons expressing the C1V1-E122 mutant chimeric protein.

In other aspects, the C1V1-E162 mutant chimeric protein is capable of mediating a depolarizing current in the cell when the cell is illuminated with light. In some embodiments the light can be green light. In other embodiments, the light can have a wavelength of between about 535 nm to about 540 nm. In some embodiments, the light can have a wavelength of about 542 nm. In other embodiments, the light can have a wavelength of about 530 nm. In some embodiments, the C1V1-E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. Additionally, in some embodiments, light pulses having a temporal frequency of about 100 Hz can be used to activate the C1V1-E162 mutant chimeric protein. In some embodiments, activation of the C1V1-E162 mutant chimeric protein with light pulses having a frequency of 100 Hz can cause depolarization-induced synaptic depletion of the neurons expressing the C1V1-E162 mutant chimeric protein.

In yet other aspects, the C1V1-E122/E162 mutant chimeric protein is capable of mediating a depolarizing current in the cell when the cell is illuminated with light. In some embodiments the light can be green light. In other embodiments, the light can have a wavelength of between about 540 nm to about 560 nm. In some embodiments, the light can have a wavelength of about 546 nm. In some embodiments, the C1V1-E122/E162 mutant chimeric protein does not mediate a depolarizing current in the cell when the cell is illuminated with violet light. In some embodiments, the chimeric protein does not mediate a depolarizing current in the cell when the cell is illuminated with light having a wavelength of about 405 nm. In some embodiments, the C1V1-E122/E162 mutant chimeric protein can exhibit less activation when exposed to violet light relative to C1V1 chimeric proteins lacking mutations at E122/E162 or relative to other light-responsive cation channel proteins. Additionally, in some embodiments, light pulses having a temporal frequency of about 100 Hz can be used to activate the C1V1-E122/E162 mutant chimeric protein. In some embodiments, activation of the C1V1-E122/E162 mutant chimeric protein with light pulses having a frequency of 100 Hz can cause depolarization-induced synaptic depletion of the neurons expressing the C1V1-E122/E162 mutant chimeric protein.

In some cases, the C1V1 variant polypeptide comprises a membrane trafficking signal and/or an ER export signal. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

*Volvox carteri* Light-Activated Polypeptide

In some embodiments, a suitable light-responsive polypeptide is a cation channel derived from *Volvox carteri* (VChR1) and is activated by illumination with light of a wavelength of from about 500 nm to about 600 nm, e.g., from about 525 nm to about 550 nm, e.g., 545 nm. In some embodiments, the light-responsive ion channel protein can comprise an amino acid sequence at least 75%, 85%, 90%, 91%, 92%, 93%, 94%, 95%, 96%, 97%, 98%, 99%, or 100% identical to the sequence shown in SEQ ID NO:19. The light-responsive ion channel protein can additionally comprise substitutions, deletions, and/or insertions introduced into a native amino acid sequence to increase or decrease sensitivity to light, increase or decrease sensitivity to particular wavelengths of light, and/or increase or decrease the ability of the light-responsive ion channel protein to regulate the polarization state of the plasma membrane of the cell. Additionally, the light-responsive ion channel protein can contain one or more conservative amino acid substitutions and/or one or more non-conservative amino acid substitutions. The light-responsive ion channel protein comprising substitutions, deletions, and/or insertions introduced into the native amino acid sequence suitably retains the ability to transport ions across the plasma membrane of a neuronal cell in response to light.

In some cases, a light-responsive cation channel protein can comprise a core amino acid sequence at least 75%, 85%, 90%, 91%, 92%, 93%, 94%, 95%, 96%, 97%, 98%, 99%, or 100% identical to the sequence shown in SEQ ID NO:19 and at least one (such as one, two, three, or more) amino acid sequence motifs which enhance transport to the plasma membranes of mammalian cells selected from the group consisting of a signal peptide, an ER export signal, and a membrane trafficking signal. In some embodiments, the light-responsive proton ion channel comprises an N-terminal signal peptide and a C-terminal ER export signal. In some embodiments, the light-responsive ion channel protein comprises an N-terminal signal peptide and a C-terminal trafficking signal. In some embodiments, the light-responsive ion channel protein comprises an N-terminal signal peptide, a C-terminal ER Export signal, and a C-terminal trafficking signal. In some embodiments, the light-responsive ion channel protein comprises a C-terminal ER Export signal and a C-terminal trafficking signal. In some embodiments, the C-terminal ER Export signal and the C-terminal trafficking signal are linked by a linker. The linker can comprise any of about 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

Also provided herein are isolated polynucleotides encoding any of the light-responsive channel proteins described herein, such as a light-responsive ion channel protein comprising a core amino acid sequence at least 85%, 90%, 91%, 92%, 93%, 94%, 95%, 96%, 97%, 98%, 99%, or 100% identical to the sequence shown in SEQ ID NO:19. Also provided herein are expression vectors (such as a viral vector described herein) comprising a polynucleotide encoding the proteins described herein, such as a light-responsive channel protein comprising a core amino acid sequence at least 85%, 90%, 91%, 92%, 93%, 94%, 95%, 96%, 97%, 98%, 99%, or 100% identical to the sequence shown in SEQ ID NO:19.

Step Function Opsins and Stabilized Step Function Opsins Based on VChR1

In other embodiments, the light-responsive polypeptide is a SFO or an SSFO based on VChR1. In some embodiments, the SFO protein can have a mutation at amino acid residue C123 of SEQ ID NO:19. In other embodiments, the SFO protein has a C123A mutation in SEQ ID NO:19. In other embodiments, the SFO protein has a C123S mutation in SEQ ID NO:19. In another embodiment, the SFO protein has a C123T mutation in SEQ ID NO:19. In some embodiments, the SFO protein can comprise an amino acid sequence at least 75%, 85%, 90%, 91%, 92%, 93%, 94%, 95%, 96%, 97%, 98%, 99%, or 100% identical to the sequence shown in SEQ ID NO:20, and comprises an alanine, serine, or threonine at amino acid 123.

In some embodiments, the SFO protein can have a mutation at amino acid residue D151 of SEQ ID NO:19. In other embodiments, the SFO protein can have a mutation at both amino acid residues C123 and D151 of SEQ ID NO:19. In one embodiment, the SFO protein has an C123S and a D151A mutation in SEQ ID NO:19. In another embodiment, the SSFO protein can comprise an amino acid sequence at least 75%, 85%, 90%, 91%, 92%, 93%, 94%, 95%, 96%, 97%, 98%, 99%, or 100% identical to the sequence shown in SEQ ID NO:21; and comprises an alanine, serine, or threonine at amino acid 122; and comprises a alanine at amino acid 151.

In some embodiments the SFO or SSFO proteins provided herein can be capable of mediating a depolarizing current in the cell when the cell is illuminated with blue light. In other embodiments, the light can have a wavelength of about 560 nm. Additionally, in some embodiments the light can be delivered as a single pulse of light or as spaced pulses of light due to the prolonged stability of SFO and SSFO photocurrents. In some embodiments, activation of the SFO or SSFO protein with single pulses or spaced pulses of light can cause depolarization of a neuron expressing the SFO or SSFO protein. In some embodiments, each of the disclosed step function opsin and stabilized step function opsin proteins can have specific properties and characteristics for use in depolarizing the membrane of a neuronal cell in response to light.

In some cases, the VChR1-based SFO or SSFO comprises a membrane trafficking signal and/or an ER export signal. In some embodiments, the trafficking signal can be derived from the amino acid sequence of the human inward rectifier potassium channel Kir2.1. In other embodiments, the trafficking signal can comprise the amino acid sequence KSRITSEGEYIPLDQIDINV (SEQ ID NO:22). Trafficking sequences that are suitable for use can comprise an amino acid sequence having at least 85%, 90%, 91%, 92%, 93%, 94%, 95%, 96%, 97%, 98%, 99%, or 100%, amino acid sequence identity to an amino acid sequence such a trafficking sequence of human inward rectifier potassium channel Kir2.1 (e.g., KSRITSEGEYIPLDQIDINV (SEQ ID NO:22)). In some cases, the ER export signal is, e.g., VXXSL (where X is any amino acid) (e.g., VKESL (SEQ ID NO:27); VLGSL (SEQ ID NO:28); etc.); NANSFCYENEVALTSK (SEQ ID NO:29); FXYENE (SEQ ID NO:30) (where X is any amino acid), e.g., FCYENEV (SEQ ID NO:31); and the like.

Screening Methods

The present disclosure provides methods of identifying an agent that is suitable for use in controlling pain.

Methods of Identifying an Agent That Reduces Pain

In some cases, a subject method involves: a) contacting a non-human animal (e.g., a non-human mammal such as a rat or a mouse) of the present disclosure with a test agent, where the non-human animal expresses a depolarizing light-activated polypeptide in a primary afferent neuron, such as a nociceptor; and b) determining the effect, if any, of the test agent on pain when the depolarizing light-activated polypeptide is illuminated (activated) with light. A test agent that reduces pain in the non-human animal, compared to the level of pain induced by light activation of the depolarizing light-activated polypeptide in the absence of the test agent, indicates that the test agent is a candidate agent for controlling (reducing) pain. In some cases, the non-human animal is a subject non-human animal model, as described above.

For example, a test agent that reduces pain by at least about 5%, at least about 10%, at least about 15%, at least about 20%, at least about 25%, or more than 25% (e.g., 25% to 50%; 50% to 75%; etc.) is considered a candidate agent for reducing pain.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 daltons and less than about 2,500 daltons. Candidate agents can comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, and derivatives, structural analogs or combinations thereof.

Assays of the present disclosure include controls, where suitable controls include a non-human animal model that expresses a depolarizing light-responsive polypeptide in a nociceptor, and that has been exposed to activating light, but has not been administered the test agent.

Whether a test agent reduces pain in the non-human animal can be determined using any of a variety of assays known in the art. For example, test that measure pain through one or more behaviors such as withdrawal, licking, immobility, and vocalization, can be used. Suitable tests include, e.g.: a) the formalin assay; b) the von Frey test; c) a thermal assay such as tail withdrawal assay, a hot plate assay, a tail flick test (Rao et al. (1996) *Neuropharmacol.* 35:393); d) the Hargreaves assay; and the like. See, e.g., Mogil, et al. (2001) *Methods in Pain Research*, Frontiers in Neuroscience; and Carter and Shieh (2010) *Nociception: Guide to Research Techniques in Neuroscience*, Burlington, Mass., Academic Press, pp 51-52; and Bannon and Malmberg (2007) *Current Protocols in Neuroscience*, Wiley Online Library. Suitable tests include those described in the Examples.

Methods of Identifying Agents that Increase the Minimum Intensity of Light Required to Produce a Pain Response The present disclosure provides a method of identifying an agent that reduces pain, the method comprising: a)

contacting a non-human animal (e.g., a non-human mammal such as a rat or a mouse) of the present disclosure with a test agent, where the non-human animal expresses a depolarizing light-activated polypeptide in a primary afferent neuron, such as a nociceptor; and b) determining the effect, if any, of the test agent on the minimum amount of light required to induce pain following administration of the test agent.

A test agent that increases the amount of light required to induce pain is a candidate agent for reducing pain. For example, a test agent that increases the amount of light (as expressed in $mW/mm^2$) required to induce pain by at least 10%, at least 15%, at least 20%, at least 25%, at least 50%, at least 75%, at least 100% (or 2-fold), at least 2.5-fold, at least 5-fold, at least 10-fold, or more than 10-fold, is considered a candidate agent for reducing pain.

For example, if the minimum light intensity of light required to produce a pain response in the non-human animal is 0.5 $mW/mm^2$, and the test agent increased the minimum amount of light required to induce pain to 0.75 $mW/mm^2$, the test agent would be considered a candidate agent for reducing pain.

As used herein, the term "determining" refers to both quantitative and qualitative determinations and as such, the term "determining" is used interchangeably herein with "assaying," "measuring," and the like.

The terms "candidate agent," "test agent," "agent", "substance" and "compound" are used interchangeably herein. Candidate agents encompass numerous chemical classes, typically synthetic, semi-synthetic, or naturally occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.) and can also be used. Alternatively, libraries of natural compounds in the form of bacterial, fungal, plant and animal extracts are available from Pan Labs (Bothell, Wash.) or are readily producible.

Candidate agents can be small organic or inorganic compounds having a molecular weight of more than 50 daltons and less than about 2,500 daltons. Candidate agents can comprise functional groups necessary for structural interaction with proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, and derivatives, structural analogs or combinations thereof.

Assays of the present disclosure include controls, where suitable controls include a non-human animal model that expresses a depolarizing light-responsive polypeptide in a nociceptor, and that has been exposed to activating light, but has not been administered the test agent. In some cases, a control is a non-human animal model that has been administered an agent known not to affect pain.

Whether a test agent increases the minimum amount of light required to induce a pain response in the non-human animal can be determined using any of a variety of assays known in the art. For example, test that measure pain through one or more behaviors such as withdrawal, licking, immobility, and vocalization, can be used. Suitable tests include, e.g.: a) the formalin assay; b) the von Frey test; c) a thermal assay such as tail withdrawal assay, a hot plate assay, a tail flick test (Rao et al. (1996) *Neuropharmacol.* 35:393); d) the Hargreaves assay; and the like. See, e.g., Mogil, et al. (2001) *Methods in Pain Research*, Frontiers in Neuroscience; and Carter and Shieh (2010) *Nociception: Guide to Research Techniques in Neuroscience*, Burlington, Mass., Academic Press, pp 51-52; and Bannon and Malmberg (2007) *Current Protocols in Neuroscience*, Wiley Online Library. Suitable tests include those described in the Examples.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Bidirectional Control of Pain

It is demonstrated here that optogenetics can be used to bidirectionally control acute pain in both normal and pathological states. A gene transduction strategy was used that is adaptable and clinically relevant. Adeno-associated virus serotype 6 (AAV6) was used. AAV6 has many attractive features; it has been used for gene delivery in non-human primates, and is a leading candidate for future use in human clinical trials[15]. It is also capable of retrograde transport, and can specifically transduce nociceptors through intraneural delivery, removing the need for risky dorsal root ganglion injections.

Materials and Methods

Animal Test Subjects and Experiments

All surgical and behavioral procedures were approved by the Stanford University Administrative Panel on Lab Animal Care. Female C57BL/6 mice (1-4 months old) were housed in groups of 5 under a 12:12 light:dark cycle. Food and water were available ad libitum.

Intraneural Injection of
AAV6-hSyn-ChR2(H134R)-eYFP and
AAV6-hSyn-eNpHR3.0-eYFP

Mice were anesthetized with 2-2.5% isoflurane, placed on a heating pad maintained at 37° C., and allowed to reach a stable plane of anesthesia, which was periodically checked through examination of breathing rate and a toe-pinch test. Fur was shaved from the femur, bilaterally or unilaterally, depending on the injection, using an electrical razor. A hair removal cream (Nair) was used to remove any remaining hair from the incision site. The incision site was then sterilized with alternating applications of ethanol and Betadine solution, and the mouse legs taped to the surgical table. 100 µl of 1 mg/ml Rimadyl was injected. Sterilized forceps and spring scissors were then used to make a 2 cm incision immediately above the femur. The gluteus superficialis and biceps femoris muscles were identified and the connective tissue between them cut to expose the sciatic nerve cavity. Retractors were used to keep the cavity open and allow for clear access to the nerve. The nerve was carefully freed from the underlying fascia using blunted micromanipulators and spring scissors. 100 µl of 0.25% Bupivacaine was injected into the incision site to simultaneously prevent the nerve from drying and induce local anesthesia. A 35G beveled needle (Nanofil# NF35BV-2, World Precision Instruments) was carefully inserted into the nerve, and 2.5-4 µl of virus solution injected at 1 µl/min, using a 25 µl syringe (Hamilton Company), connected to a Harvard PHD Syringe pump (Harvard Apparatus). When possible, 2 separate injections were made into the common peroneal and tibial branches of the sciatic nerve, to ensure that the nerve was filled uniformly. ChR2 injected mice received $3 \times 10^{10}$ vg (from UNC Vector Core), while NpHR injected mice received either $1 \times 10^{11}$ vg or $3 \times 10^{11}$ vg (from UNC Vector Core and Virovek, respectively). Depending on the mouse, this procedure was performed either unilaterally or bilaterally. The incision was then sutured closed using 5-0 suture.

Isolation, Culture and Electrophysiology of Opsin-Expressing DRG Neurons

Isolation of DRG

Dorsal root ganglion (DRG) excision, culture and electrophysiology procedures were largely based on previously reported protocols[23]. Mice, three to four weeks after intraneural injection, were deeply anesthetized with isoflurane 5% and fur was shaved from the back. Mice were then perfused with 4° C. sterile phosphate buffered saline. The following isolation steps were rapidly performed, and completed within 5 minutes after perfusion. After removing the skin from the back, using sterile procedure, the muscles along the vertebral column were cut and bone rongeurs used to peel away any muscle or tendon superficial to the vertebrae. The rongeurs were used to break away the vertebral bone directly dorsal to the spinal cord, starting at the base of the spine, and moving rostrally. Muscle lateral to the spinal cord was peeled away until the sciatic nerve branches could be visualized, and bones were broken lateral to the spinal cord to free the path of the nerve. Each nerve branch was cut using small spring scissors, pulled proximally with forceps until the dorsal root ganglion could be visualized, and cut proximal to the DRG. The DRG was then placed in 4° C., sterile MEM-complete solution (minimal essential media, MEM vitamins, antibiotics, and 10% fetal bovine serum). Three DRGs were excised from each expressing side of the mouse.

DRG Culture

Excised DRGs were desheathed and transferred to MEM-Collagenase solution (minimal essential media, vitamins, antibiotics, no fetal bovine serum, 0.125% collagenase). The tissue was incubated at 37° C. for 45 minutes in a water bath and then triturated in 2.5 ml TripleE Express (Invitrogen). The trypsin was quenched with 2.5 ml MEM-complete with 80 ug/ml DNase I, 100 µg/ml trypsin inhibitor from chicken egg white and 2.5 mg/ml $MgSO_4$. Cells were centrifuged, and resuspended in MEM-complete at a cell density of 500,000 cells/ml. 100 ul of the cell suspension was carefully placed as a bubble on matrigel-coated coverslips, and then incubated at 37° C., 3% $CO_2$, 90% humidity. Two hours after initial incubation, the cultured neurons were flooded with 1 ml of MEM-complete. Cells were maintained 2-7 days in culture with fresh media changes as needed until electrophysiology was performed.

Electrophysiology

A Spectra X Light engine (Lumencor) or DG4 xenon lamp (Sutter Instruments) was used to identify fluorescent protein expression, and deliver light pulses for opsin activation. A 475/28 filter was used to apply blue light for ChR2, and a 586/20 filter was used to apply yellow light for NpHR. Light power density through the microscope objective was measured with a power meter (ThorLabs). Whole-cell recordings were obtained with patch pipettes (4-6 MΩ) pulled from borosilicate glass capillaries (Sutter Instruments) with a horizontal puller (P-2000, Sutter Instruments). The external recording solution contained (in mM): 125 NaCl, 2 KCl, 2 $CaCl_2$, 2$MgCl_2$, 30 glucose, 25 HEPES, and 1 µM tetrodotoxin when necessary to eliminate escape spikes for peak photocurrent measurements. The internal recording solution contained (in mM): 130 K-gluconate, 10 mM KCl, 10 HEPES, 10 EGTA, 2 $MgCl_2$. Recordings were made using a MultiClamp700B amplifier (Molecular Devices), and pClamp10.3 software (Molecular Devices) was used to record and analyze data. Signals were filtered at 4 kHz using a Bessel filter and digitized at 10 kHz with a Digidata 1440A analog-digital interface (MolecularDevices). Peak and steady-state photocurrents were measured from a 1 s light pulse in voltage-clamp mode, where cells were held at −50 mV. Series resistances were carefully monitored and recordings were not used if the series resistance changed significantly (by >20%) or reached 20 MΩ.

Latency to Light Measurement

Experimental Protocol

Approximately 1 to 5 weeks after intraneural injection, mice were placed in a plastic enclosure with a thin, transparent, plastic floor and allowed to habituate to the test setup for 30 minutes prior to testing. A multimode optical fiber (Thor Labs, #AFS105/125Y) attached to a laser (OEM Laser Systems, 473 nm, 1 mW/mm$^2$) was directed at the footpad through the floor. To begin the trial, the animal was required to: (1) be awake, (2) have all four paws on the floor, and (3) be at rest, not preparing to walk. Latency was calculated from when the footpad was illuminated to when the paw was withdrawn. To avoid experimenter bias, no subjective criteria were applied to the end-point for latency calculation, i.e. normal ambulation was also considered to end the trial. A maximum latency of 1 minute was set to ensure practicality of data collection. Individual trials were at least 2 minutes apart, and each mouse had five trials, which were averaged together. All trials were video recorded at 30 frames per second and latencies calculated through video analysis post-collection.

Statistics

A one-way ANOVA was used to analyze changes in ChR2+ mice's latencies in response to blue light in weeks 1-5 as compared with ChR2+ mice's response to yellow light. Dunnett's post-hoc multiple-comparisons test was used to determine which latencies were significantly different from yellow-light controls. Effect sizes were calculated using g, an extension of Hedges' g for multiple groups[24].

Place Aversion

Construction of 2 Chamber Place Aversion Setup

A 2 chamber place setup was built with an entryway connecting the two 10 cm×12 cm chambers. The floor of each chamber, one red, the other blue, was illuminated with a 10×12 array of light-emitting diodes (Blue LEDs: 475 nm, Red LEDs: 625 nm, Cree) and directed with mirrors such that the light power density was equivalent in each room (0.15 mW/mm$^2$).

Experimental Protocol

A single mouse was allowed to explore the 2 chamber set up for 10 minutes prior to testing with the LED array floors turned off. Then, the mouse's location was recorded using a video camera and analyzed using BIOBSERVE Viewer[2]. The mouse position was recorded with the lights off for 10 minutes, and then the lights were switched on, and the position recorded for a further 30 minutes.

Statistics

A two-sided paired Student's t-test was used to examine whether changes in mouse position preference between the 'fights-off' and 'lights-on' condition were statistically significant. The percentage change between the two conditions was then calculated for each ChR2+ and NpHR+ mice. These percentages were then compared using a two-sided, unpaired, Student's t-test for heteroscedastic populations). Effect sizes were calculated using Hedges' g.

Measurement of Mechanical Withdrawal Thresholds

Mechanical allodynia was investigated through von Frey testing. Mice were allowed to habituate to the test setup for 1 hour prior to testing. Hairs of various forces were applied to the bottom of the foot using the Up-and-down method[25,26] for approximately 2 seconds.

The appearance of any of the following behaviors was considered as a withdrawal response: (1) rapid flinch or withdrawal of the paw, (2) spreading of the toes, or (3) immediate licking of the paw. If the animal moved the paw for some other reason before the end of the 2 seconds, the test was considered ambiguous and repeated. Depending on the opsin used, we then performed simultaneous illumination of the mouse's paw with blue light (473 nm, 0.15 mW/mm$^2$) or yellow light (593 nm, 0.15 mW/mm$^2$) The von Frey test was conducted by a single examiner for all data collected, who was always blinded to whether the mice being tested had opsin expression or not.

Statistics

Changes in von Frey threshold were tested for statistical significance using the non-parametric two-sided Wilcoxon signed-rank test. Effect sizes were calculated using Hedges' g.

Measurement of Thermal Withdrawal Latency

A modified Hargreaves plantar test apparatus was used to measure changes in thermal sensitivity with different types of illumination. The standard Hargreaves test glass plate was raised slightly to allow placement of an LED ring above the infrared emitter. The LED ring was calibrated to emit 0.15 mW/mm$^2$ of blue (475 nm, Cree) or yellow (590 nm, OSRAM Opto Semiconductors) light. To control for light-induced confounds, withdrawal latency to infrared heat when mice received on-spectrum illumination (blue light for ChR2 injected mice, and yellow light for NpHR injected mice) was compared with off-spectrum illumination (vice versa). Withdrawal latency was automatically measured between onset of infrared light and the first paw withdrawal. Infrared intensity was kept constant across all trials, and the tester was always blinded as to whether the mice being tested had opsin expression or not.

Statistics

Changes in thermal withdrawal latency were compared between off-spectrum and on-spectrum illumination conditions using a two-sided, paired, Student's t-test. Effect sizes were calculated using Hedges' g.

Chronic Constriction Injury

The chronic constriction injury model used here was adapted from an existing protocol[27]. Animals were anesthetized with isoflurane and the sciatic nerve was exposed unilaterally in a similar fashion to the sciatic nerve exposure used for the intraneural injections. One 7-0 prolene double-knot ligature was tied around the nerve such that the ligature was just able to slide along the nerve, and the free ends of the suture were cut short. Non-absorbable 5-0 suture was used to close the wound. In order to promote development of neuropathic pain, no post-operative analgesics were administered.

Immunohistochemistry, Imaging, and Quantification of Transduction

Immunohistochemistry

Mice were euthanized with 100 μl Beuthanasia-D, and transcardially perfused with 10 ml of 4° C. phosphate-buffered saline (1×PBS) and 10 ml of 4% paraformaldehyde (PFA). Bone rongeurs, spring scissors and forceps were used to carefully remove the sciatic nerve, associated dorsal root ganglia and the spinal cord together from the mouse. The feet were removed separately. All tissue was placed in 4% PFA overnight, stored at 4° C. Following this, samples were transferred to 30% sucrose (in 1×PBS) and stored for varying lengths of time (at minimum 1 day). Samples were later dissected under microscopic guidance, and frozen separately in Tissue-Tek O.C.T. Samples were cut at 20 thickness using a cryostat (Leica CM3050S), and mounted on slides. All samples were rinsed 3×10 min in 1×PBS to remove any residual OCT. For all targets except myelin, samples were then blocked in 0.3% Triton-X100, 2% Normal Donkey Serum (NDS), dissolved in 1×PBS for 1 hour. Samples were then incubated overnight with primary antibody solutions with 0.3% Triton-X100, 5% NDS, dissolved in 1×PBS. The next day, samples were rinsed 3×10 min with 1×PBS, and then incubated for 1 hour with secondary antibody solutions dissolved in 1×PBS. Samples were then rinsed 3×10 min in 1×PBS, and coverslipped with PVA DABCO. Primary antibodies used were Rat anti-Substance P (1:500, #556312, BD Pharmingen), Biotin-IB4 (1:50, #B-1205, Vector Laboratories), Rabbit anti-Somatostatin Receptor 2 (1:250, #ab134152, Abcam) and Rabbit anti-VR1 (for TRPV1, 1:500, #ab31895, Abeam). Secondary antibodies used were Cy5 Donkey anti-Rabbit (1:500, #711-175-152, Jackson Laboratories), Cy3 Donkey anti-Rat (1:500, #711-165-152, Jackson Laboratories) and Streptavidin-Texas Red (3:100, #SA-5006, Vector Laboratories). For myelin, samples were permeabilized for 1 hour using 0.2% Triton-X100 dissolved in 1×PBS. Samples were then incubated with FluoroMyelin Red (1:300, #F34652, Molecular Probes) for 20 min. Following this, samples were rinsed 3×10 min in 1×PBS, and coverslipped with PVA DABCO.

Confocal Imaging

Samples were imaged using a Leica TCS SP5 confocal scanning laser microscope, using a 20× oil immersion objective, and analyzed using Leica LAS AF software. Images were later processed using Fiji[28], which was used to stitch together z-stacks, balance image brightness and contrast, and modify colors to account for color-blindness.

Quantification

DRGs from 3 different mice injected with AAV6-ChR2 were examined for co-expression with Substance P, TRPV1, Somatostatin and IB4, and examined nerve samples from 3 different mice for co-expression with myelin. For each marker, the percentage of marker-expressing neurons/axons that were YFP positive, and the percentage of YFP positive neurons/axons that were positive for the given marker, were quantified.

Results

AAV6-hSyn-ChR2(H134R)-eYFP was injected into the sciatic nerve of mice (FIG. 1a). Two to four weeks after injection, electrophysiological recordings from isolated ChR2 positive neurons in the dorsal root ganglia revealed that ChR2 was functional, and expressing cells could fire action potentials when stimulated at 5-10 Hz with 1 $mW/mm^2$ 475 nm light (FIG. 1b; FIG. 6). In addition, ChR2 was expressed throughout the neuron, terminating in central projections to the dorsal horn of the spinal cord, with little expression seen in deeper laminae or in ascending dorsal columns, suggesting that the transduced neurons were nociceptors projecting to Rexed's lamina I/II (FIG. 1c) Immunohistochemistry showed considerable overlap between ChR2 expression and nociceptive markers, such as IB4, Substance P, TRPV1, and Somatostatin. No overlap was observed between ChR2 and myelin, indicating that no proprioceptors were transduced in the sciatic nerve; instead, expression was restricted to unmyelinated nociceptors (putative C-fibers) (Table 1, provided in FIG. 9). Further, transduced dorsal root ganglia neurons were smaller in diameter than untransduced neurons (FIG. 6), consistent with prior histological evidence regarding C-fiber size[17].

The behavioral effect of optogenetic activation of these transduced nociceptors was examined. Mice were allowed to freely explore a chamber with a transparent floor. After habituation, blue light (1 $mW/mm^2$) was shown on the plantar hindpaws of ChR2 injected mice with the aim of optogenetically activating nociceptor nerve endings in the skin, and observed characteristic pain-like behavior (FIG. 2a). In response to blue light, mice flinched, engaged in prolonged foot-licking or vocalized: operant behaviors associated with pain[18]. To quantify this effect, the time between light onset and any paw withdrawal was measured, regardless of whether such withdrawal was due to pain or normal exploratory behavior. This latency reduced dramatically 2 weeks after injection (P=0.034, effect size: 2.10), and remained low for 3 weeks thereafter (week 3: P=0.027, effect size=2.17; week 4: P=0.026, effect size=2.19), as compared with latencies recorded from YFP-injected mice, and ChR2 injected mice that received off-spectrum yellow light illumination (FIG. 2b). Latencies increased 5 weeks following injection, potentially due to shutdown of transgene expression in some tested mice, as has been previously reported with AAV6 in mice[19]. Despite stimulation being entirely transcutaneous, ChR2 injected mice were light sensitive, withdrawing in a few hundred milliseconds in response to low intensities of blue light (1 $mW/mm^2$) Lower levels of illumination showed progressively less of an effect, while an increase in illumination intensity past 1 $mW/mm^2$ did not result in any additional decrease in latency (FIG. 2c).

To test if optogenetic induction of pain was tunable, it was asked if lower intensities of illumination (0.25 $mW/mm^2$) that did not prove immediately aversive would cause more subtle effects. A place aversion apparatus was constructed, in which the floor of each chamber was illuminated with an LED array that emitted either off-spectrum (red, 625 nm) or on-spectrum (blue, 475 nm) light (FIG. 2d). ChR2 injected mice when exploring the blue chamber did not show any outward signs of pain, and did not engage in foot-licking or flinch from the light, but showed an 80-20% preference for the red chamber over the blue chamber (P=0.0013, effect size=3.11). YFP injected mice showed no significant preference (FIG. 2e,f). Such aversion is potentially caused by low levels of pain that do not rise to levels that induce reflexive withdrawal, but still cause changes in operant behavior.

It was reasoned that such low levels of optogenetic stimulation may also act to sensitize ChR2 injected mice to otherwise inoffensive stimuli. To demonstrate this, von Frey testing of the mechanical withdrawal threshold and Hargreaves testing of the thermal withdrawal latency was conduced, but with concurrent illumination of the relevant paw with low intensities of blue light (0.15 $mW/mm^2$, FIG. 3a, b). While such illumination was insufficient to induce immediate aversion (FIG. 2c), it did significantly lower von Frey thresholds (FIG. 3b) by 50% (P=0.027, effect size=0.904), and lower Hargreaves latency (FIG. 3f, g) by 55% (P=0.00038, effect size=2.77). Such sensitization may occur through sub-threshold depolarization induced in nociceptor free nerve endings, which may render them more sensitive to otherwise innocuous stimuli. Wild type mice showed no significant difference in behavior between illuminated and non-illuminated tests.

To complement our ability to optogenetically induce pain, methods were developed to optogenetically inhibit action potential generation in nociceptors. Such inhibition could have great therapeutic value, and provide a type of spatially and temporally restricted control over action potential generation not possible with pharmacology or electrical stimulation.

Figure 7:
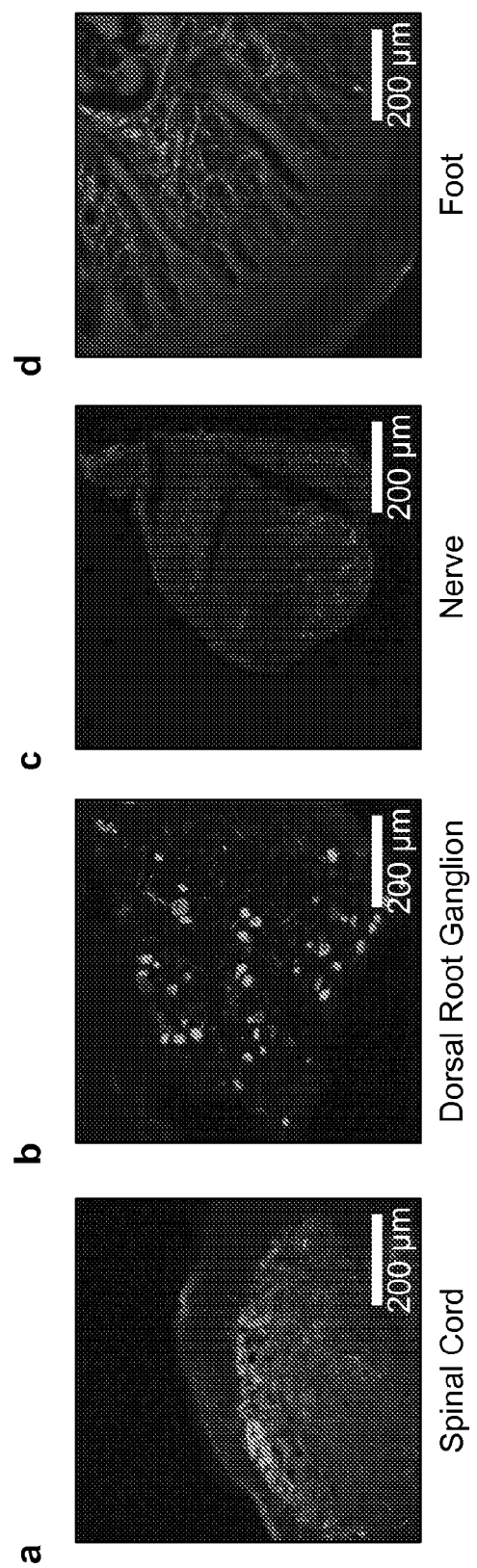
FIGS. 7A-D depict representative images of NpHR transduction observed after intra-sciatic injection of AAV2/6-hSyn-eNpHR3.0-eYFP.
Figure 8:
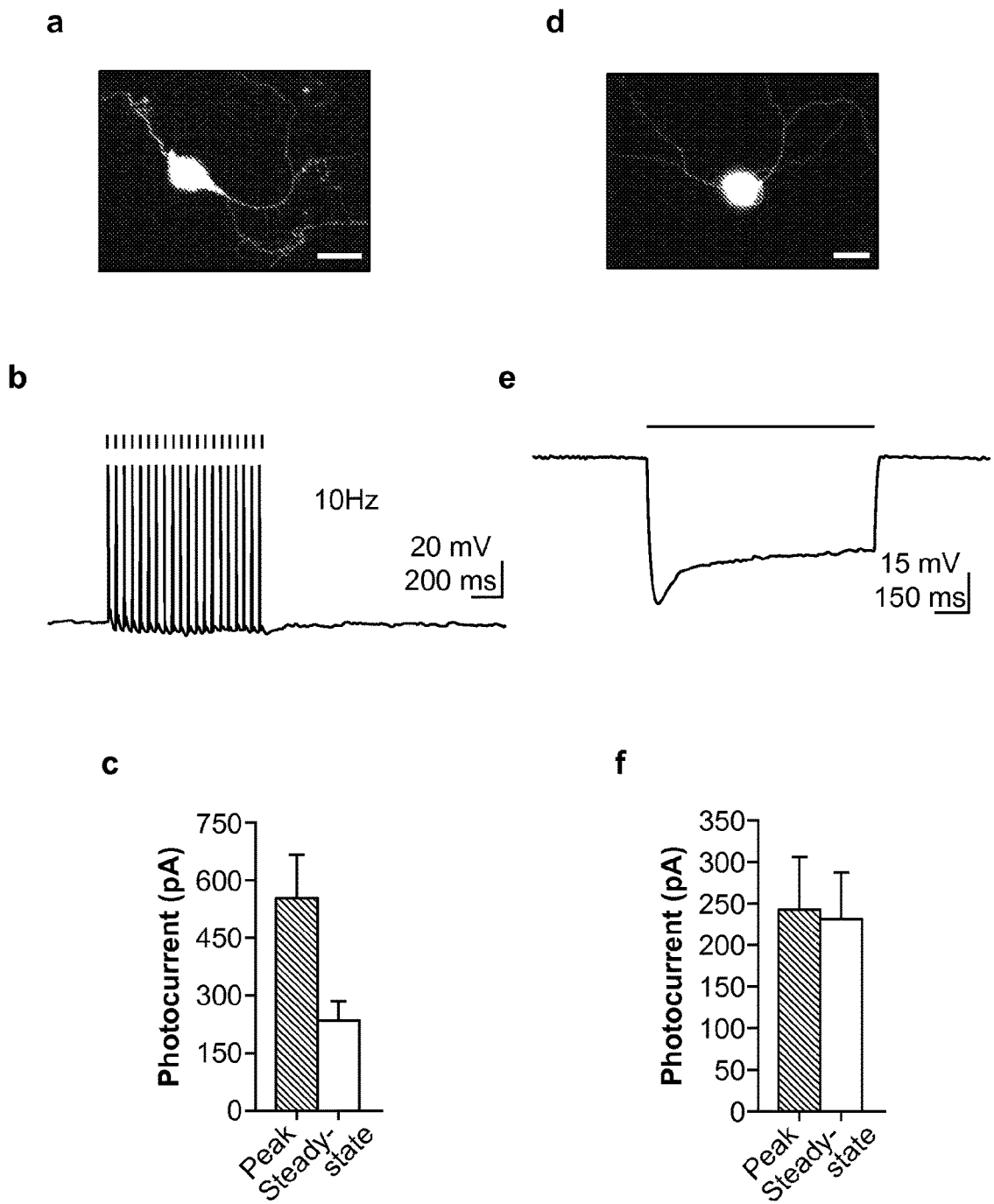
FIGS. 8A-F depict electrophysiological recording from ChR2+ and NpHR+ DRG neurons.

Mice were injected in the sciatic nerve with AAV6-hSyn-eNpHR3.0-eYFP; and similar transduction profiles to our ChR2 results were observed (FIG. 7). Electrophysiological recordings of isolated cultured NpHR positive DRG neurons revealed strong hyperpolarization in response to constant yellow light illumination that was sufficient to block action potential initiation (FIG. 3c; FIG. 8).

NpHR-injected mice were tested using similarly modified von Frey and Hargreaves apparatuses that emitted yellow (593 nm) light. The NpHR-injected mice, when illuminated with 1.1-1.7 mW/mm$^2$ light, had a 69% increase (P=0.0043, effect size=0.802) in their von Frey withdrawal thresholds (FIG. 3d, e). Low intensities of yellow light (0.15 mW/mm$^2$) were sufficient to increase Hargreaves withdrawal latency by 97% (P=0.00019, effect size=2.05). Wild type mice showed no significant change in behavior upon illumination with yellow light.

Finally, whether the ability to optogenetically inhibit nociception was therapeutically relevant was determined by testing in an animal model of neuropathic pain. Baseline von Frey and Hargreaves testing were performed on NpHR-injected mice, replicating our initial findings that yellow light desensitized mice to mechanical and thermal stimuli (FIG. 4a,4b). A chronic constriction injury was performed to induce symptoms of neuropathic pain in these mice. As expected, mice showed thermal and mechanical allodynia following the injury. Mice were then illuminated with yellow light while performing von Frey and Hargreaves testing. It was observed that optogenetic inhibition could reverse mechanical allodynia, increasing von Frey thresholds from 36 to 94% of pre-injury, non-illuminated levels (P=0.0020, effect size=0.920, FIG. 4a) Similarly, optogenetic inhibition also reversed thermal hyperalgesia in NpHR injected mice, increasing Hargreaves withdrawal latency from 55% to 128% of normal, non-illuminated levels (P=0.012, effect size=1.91, FIG. 4b). In both cases, YFP injected controls showed no significant changes with illumination, both before, and after chronic constriction injury.

Thus, the data show that opsins can be successfully expressed with high specificity in nociceptors through a relatively simple injection procedure that does not require transgenesis. Moreover, sufficiently strong opsin expression and trafficking to achieve robust behavioral effects through non-invasive transcutaneous illumination were observed. It is believed that this is due to expression of opsins in dermal and subdermal free nerve endings, which can be illuminated with minimal optical attenuation. Interestingly, effects of optogenetic illumination on mechanical and thermal thresholds were observed even when this illumination had low intensity. This may be due to the resting potential and baseline excitability of free nerve endings, which may allow relatively small optically induced membrane currents to still influence downstream neurotransmitter release. Optogenetic effects were observed over a 3-week period, from 2 to 5 weeks following AAV6 injection.

The optogenetic capabilities reported here can be widely used by scientists who seek non-invasive ways to perturb nociceptive function. In particular, as opsin expression is specific to unmyelinated nociceptors, optogenetics could be used to understand the role of nociceptor activity in the genesis of neuropathic pain, through chronic bidirectional optogenetic control. Researchers who seek greater specificity and who do not wish to develop custom transgenic mice for each individual opsin could instead use Cre-dependent DIO-AAV6[22] in concert with any of the many different nociceptor-specific Cre lines, to achieve opsin expression restricted to sub-populations of nociceptors. Non-invasive, transcutaneous optogenetic inhibition can be used as a treatment for pain, e.g., intractable chronic pain.

FIG. 1: Intra-sciatic injection of rAAV2/6-hSyn-ChR2 (H134R)-eYFP transduced unmyelinated nociceptors that projected to spinal cord lamina I. a) Injection schematic b) Electrophysiology of dissociated ChR2+ DRG neurons. Representative whole-cell current-clamp recordings showing optogenetically induced action potentials in response to 475 nm light (5 Hz, 1 mW/mm$^2$) and representative whole-cell voltage-clamp recordings in response to a light pulse (1 s, 475 nm, 1 mW/mm$^2$) The cell is held at −50 mV. c) Expression profile at the spinal cord, DRG, nerve and foot; ChR2 is shown in green, cellular markers in magenta, overlay in white. ChR2 did not colocalize with myelinated neurons, but did colocalize with nociceptive markers including IB4, Somatostatin, TRPV1 and Substance P.

Figure 2:
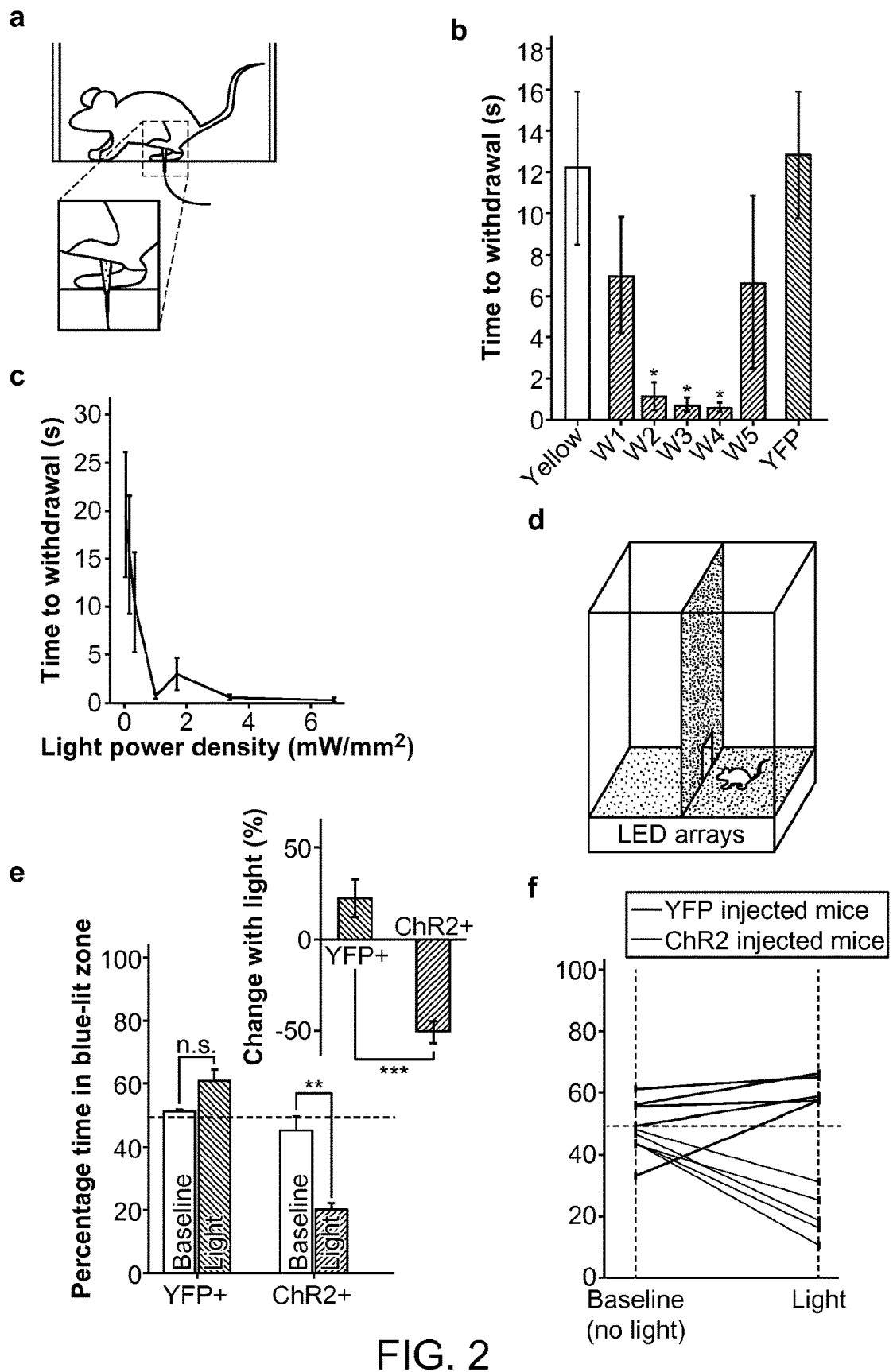
FIGS. 2A-F depict data showing that transdermal illumination of ChR2$^+$ mice resulted in tunable pain-like behavior.

FIG. 2: Transdermal illumination of ChR2+ mice resulted in tunable pain-like behavior. a) Experimental schematic b) Time-dependence of light-sensitivity in ChR2+ mice (Light: 1 mw/mm$^2$) (n=4 mice). Latencies in response to blue light were significantly lower compared to yellow light latencies, from week 2 to week 4 following injection (One-way ANOVA: F(6,21)=3.98; P=0.0082; Dunnett's test: P (week 2)=0.034, P (week 3)=0.027, P (week 4)=0.026; effect size (week 2)=2.10, effect size (week 3)=2.17, effect size (week 4)=2.19). Latencies recorded from YFP+ controls and from ChR2+ mice at week 1 and week 5 were not significant (P (week 1)=0.55, P (week 5)=0.49, P (YFP+)=0.99). c) Light-sensitivity decreased with increase in intensity of blue light, steeply until intensity was 1 mW/mm$^2$, stabilizing past this threshold. d) Place aversion schematic e) YFP+ mice showed a non-significant preference for the blue-lit areas (19.9% increase in time spent in blue-lit areas, P=0.06, n=5), while ChR2 mice were significantly averse to blue-lit areas (55.6% decrease in time spent in blue-lit areas, effect size=3.11, P=0.0013, n=5). Inset: these two percent changes were statistically different from each other. (P=0.00061) f) Individual traces for place aversion data. All grouped data are shown as mean±s.e.m.

Figure 3:
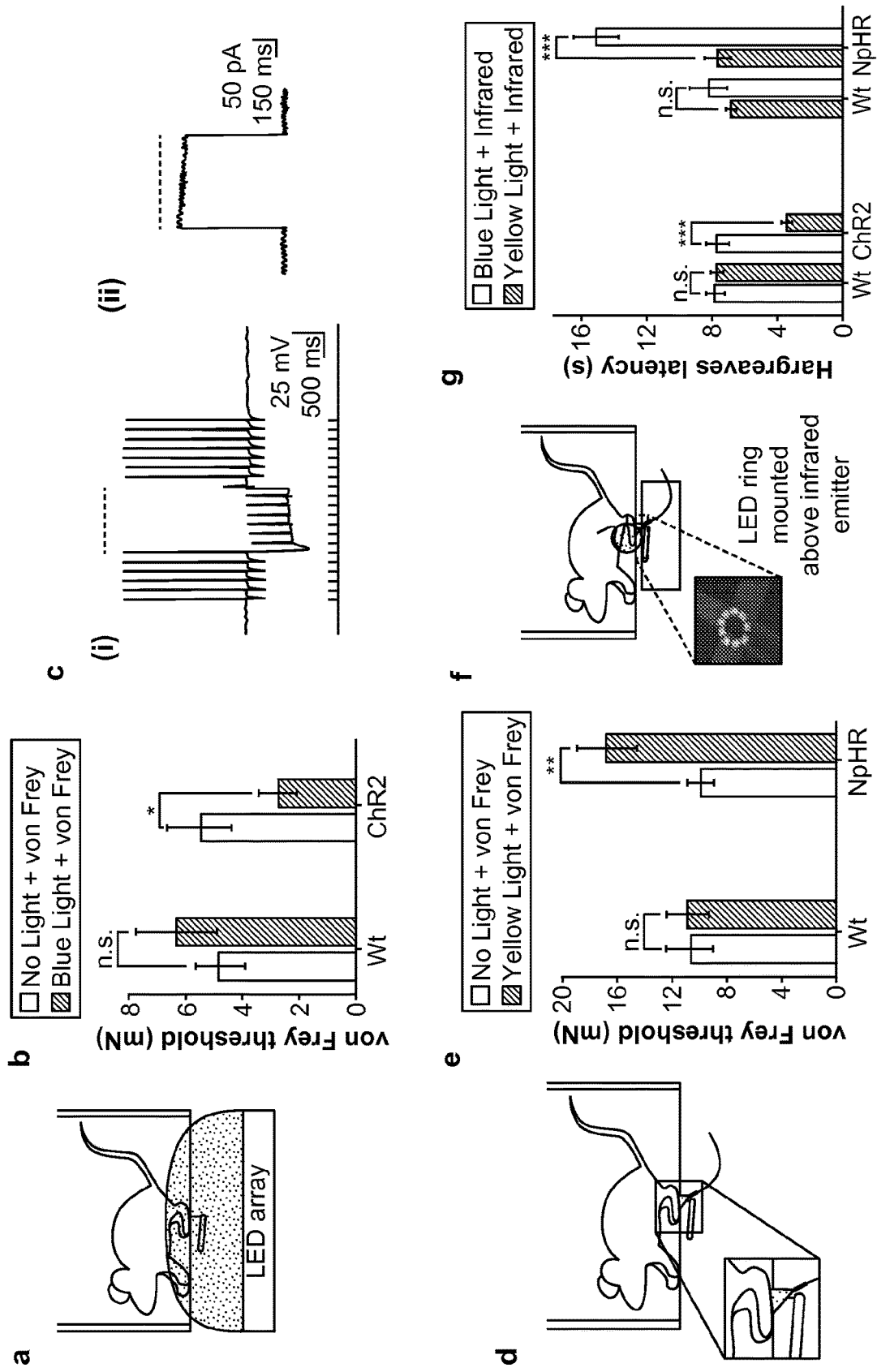
FIGS. 3A-G depict responses in blue light-sensitized ChR2-expressing mice and yellow light-desensitized NpHR-expressing mice to mechanical and thermal stimuli.

FIG. 3: Blue light sensitized ChR2 expressing mice and yellow light desensitized NpHR expressing mice to mechanical and thermal stimuli. a) Schematic of ChR2-mediated sensitization (0.15 mW/mm$^2$ blue light intensity) b) von Frey thresholds reduced 50% in ChR2+ mice (effect size=0.904, P=0.027, n=10 paws), while wild-types showed no significant change (P=0.50, n=10 paws). c) i) Representative whole-cell voltage-clamp recording showing outward photocurrent in an NpHR-expressing DRG neuron, in response to a 1 s, 586 nm light pulse (indicated by yellow bar). ii) Representative whole-cell current-clamp recordings showing yellow (586 nm) light-mediated inhibition of electrically evoked spikes (400 pA current injection, 5 ms pulse width) in an NpHR-expressing DRG neuron. d) Schematic of NpHR-mediated inhibition (1.1-1.7 mW/mm$^2$ light intensity) e) von Frey thresholds increased 69% NpHR+ mice (effect size=0.802, P=0.0043, n=24 paws) while wild-type mice showed no significant change (P=0.71, n=20 paws). f) Schematic of optogenetic modulation of thermal thresholds. Blue/Yellow light intensity (0.15 mW/mm$^2$) g) Withdrawal latency to infrared stimulus decreased 55% in ChR2+ mice during blue light illumination (effect size=2.77, P=0.00038, n=7 paws) and increased 97% in NpHR+ mice during yellow light illumination (effect size=2.05, P=0.00019, n=10 paws) (compared to off-spectrum illumination), while wild-type latencies did not significantly change (P=0.91, n=9 paws, controls for ChR2+ mice, P=0.26, n=10 paws, controls for NpHR+ mice). All grouped data are shown as mean±s.e.m.

Figure 4:
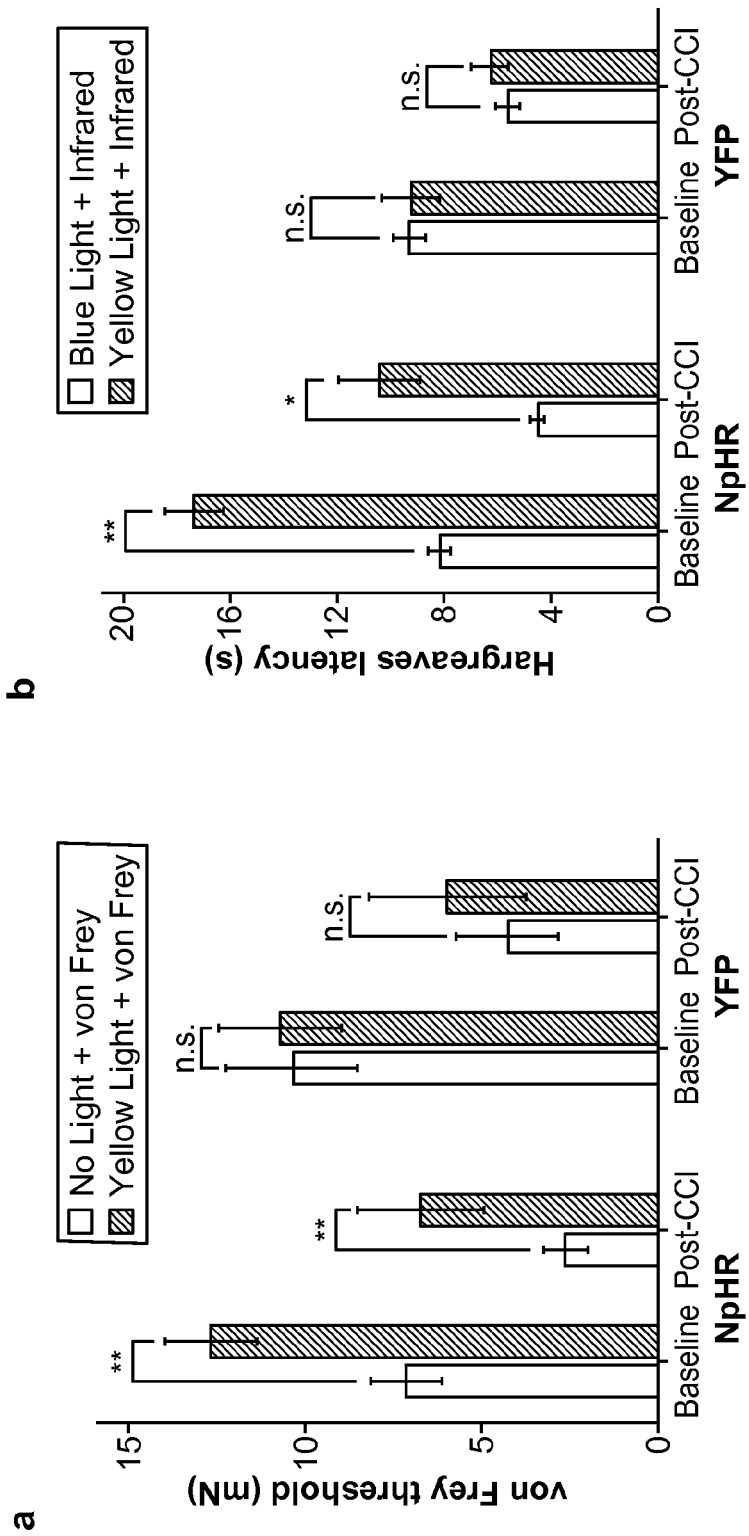
FIGS. 4A and 4B depict data showing that yellow light stimulation of NpHR$^+$ mice reversed mechanical allodynia and thermal hyperalgesia caused by a chronic constriction injury.

FIG. 4: Yellow light stimulation of NpHR+ mice reversed mechanical allodynia and thermal hyperalgesia caused by a chronic constriction injury (CCI). a) Before CCI, yellow light significantly increased von Frey thresholds of NpHR+ mice (78% increase, effect size=1.43, P=0.0020, n=10 paws), but not of YFP+ mice (P=0.41, n=12 paws). After CCI, von Frey thresholds of all mice significantly reduced (NpHR+ mice, 64% reduction, effect size=1.61, P=0.0020, n=10 paws; YFP+ mice, 59% reduction, effect size=1.03, P=0.00049, n=12 paws). Yellow light significantly increased von Frey thresholds of NpHR+ mice to near pre-CCI levels (258% increase, effect size=0.92, P=0.0020, n=10 paws), but did not significantly change the thresholds of YFP+ mice (P=0.57, n=12 paws). b) Before CCI, yellow light significantly increased withdrawal latency to infrared stimulus in NpHR+ mice (112% increase, effect size=3.95, P=0.00025, n=7 paws, compared to off-spectrum illumination), while YFP+ mice showed no significant change (P=0.97, n=9 paws). After CCI, all mice showed a reduction in withdrawal latency to infrared stimulus during off-spectrum illumination (NpHR+ mice, 45% reduction, effect size=3.75, P=0.00077, n=7 paws; YFP+ mice, 40% reduction, effect size=2.06, P=0.0038, n=9 paws). Yellow light significantly increased this latency in NpHR+ mice (132% increase, effect size=1.91, P=0.012, n=7 paws) beyond initial pre-CCI latencies, but did not significantly change latency in YFP+ mice (P=0.53, n=9 paws). All grouped data are shown as mean±s.e.m.

FIG. 6: Size distribution of opsin transduction. Intraneural injection of a) AAV6:ChR2 and b) AAV6:NpHR results in opsin transduction that is specific to smaller diameter nociceptors (n=205 ChR2+ neurons, 666 ChR2− neurons, n=217 NpHR+ neurons, 355 NpHR− neurons). AAV6:ChR2 transduced 80% of neurons<16 µm, AAV6:NpHR transduced 75% of neurons<16 µm.

FIG. 7: Representative images of NpHR transduction observed after intra-sciatic injection of AAV2/6-hSyn-eNpHR3.0-eYFP.

FIG. 8: Electrophysiological recording from ChR2+ and NpHR+ DRG neurons. a) Image of ChR2+ DRG neuron, scale bar 25 µm. b) Sample whole-cell current-clamp recordings showing spikes evoked by 10 Hz blue (475 nm) light pulse trains (5 ms pulse widths) in a ChR2+ DRG neuron. Cell is held at −50 mV, light power density is 1 mW/mm$^2$. c) Summary graph of peak and steady-state photocurrents in response to 1 s, 475 nm blue light. Mean±SEM is plotted, n=7. d) Image of NpHR+ DRG neuron, scale bar 25 µm. e) Sample whole-cell current-clamp recordings showing yellow (586 nm) light-mediated hyperpolarization in an NpHR+ DRG neuron. Cell is held at −48 mV, light power density is 1 mW/mm$^2$. f) Summary graph of peak and steady-state photocurrents in response to 1 s, 586 nm yellow light. Mean±SEM is plotted, n=10.

FIG. 9 presents Table 1. Analysis of opsin transduction profiles. Co-localization percentages calculated from analysis of DRGs from 3 different ChR2+ and NphR+ mice each. Somatostatin+, VR1+ and IB4+ neurons are the major components of the opsin+ pool.

REFERENCES

1. Dubin, A. E. & Patapoutian, A. Review series Nociceptors: the sensors of the pain pathway. *The Journal of Clinical Investigation* 120, 3760-3772 (2010).
2. Costigan, M., Scholz, J. & Woolf, C. J. Neuropathic pain: a maladaptive response of the nervous system to damage. *Annual Review of Neuroscience* 32, 1-32 (2009).
3. Fenno, L., Yizhar, O. & Deisseroth, K. The Development and Application of Optogenetics. *Annual Review of Neuroscience* 34, 389-412 (2011).
4. Liske, H. et al. Optical inhibition of motor nerve and muscle activity in vivo. *Muscle & Nerve* 47, 916-921 (2013).
5. Llewellyn, M. E., Thompson, K. R., Deisseroth, K. & Delp, S. L. Orderly recruitment of motor units under optical control in vivo. *Nature Medicine* 16, 1161-5 (2010).
6. Ji, Z.-G. et al. Light-evoked somatosensory perception of transgenic rats that express channelrhodopsin-2 in dorsal root ganglion cells. *PLOS One* 7, e32699 (2012).
7. Wang, H. & Zylka, M. J. Mrgprd-expressing polymodal nociceptive neurons innervate most known classes of substantia gelatinosa neurons. *The Journal of Neuroscience: the official journal of the Society for Neuroscience* 29, 13202-9 (2009).
8. Daou, I. et al. Light-induced nociception: Remote optogenetic control of peripheral pain pathways in freely moving mice. *Society for Neuroscience Conference* 575.06/1111 (2012).
9. Mourot, A. et al. Rapid optical control of nociception with an ion-channel photo switch. *Nature Methods* 9, 396-402 (2012).
10. Kokel, D. et al. Photochemical activation of TRPA1 channels in neurons and animals. *Nature Chemical Biology* 9, 257-263 (2013).
11. Mattis, J. et al. Principles for applying optogenetic tools derived from direct comparative analysis of microbial opsins. *Nature Methods* 9, (2012).
12. Williams, J. C. & Denison, T. From optogenetic technologies to neuromodulation therapies. *Science Translational Medicine* 5, 177ps6 (2013).
13. Chow, B. Y. & Boyden, E. S. Optogenetics and translational medicine. *Science Translational Medicine* 5, 177ps5 (2013).
14. Towne, C., Schneider, B. L., Kieran, D., Redmond, D. E. & Aebischer, P. Efficient transduction of non-human primate motor neurons after intramuscular delivery of recombinant AAV serotype 6. *Gene Therapy* (2009).
15. Asokan, A., Schaffer, D. V & Samulski, R. J. The AAV vector toolkit: poised at the clinical crossroads. *Molecular Therapy* 20, 699-708 (2012).
16. Towne, C., Pertin, M., Beggah, A. T., Aebischer, P. & Decosterd, I. Recombinant adeno-associated virus serotype 6 (rAAV2/6)-mediated gene transfer to nociceptive neurons through different routes of delivery. *Molecular Pain* 5, 52 (2009).
17. Ruscheweyh, R., Forsthuber, L. & Schoffnegger, D. Modification of Classical Neurochemical Markers in Identified Primary Afferent Neurons With Aβ-, Aδ-, and C-Fibers After Chronic Constriction Injury in. *The Journal of Comparative Neurology* 336, 325-336 (2007).
18. Mogil, J. S. Animal models of pain: progress and challenges. *Nature Reviews Neuroscience* 10, 283-294 (2009).
19. Mason, M. R. J. et al. Comparison of AAV serotypes for gene delivery to dorsal root ganglion neurons. *Molecular Therapy: the journal of the American Society of Gene Therapy* 18, 715-24 (2010).
20. Bennett, G. J. & Xie, Y. K. A peripheral mononeuropathy in rat that produces disorders of pain sensation like those seen in man. *Pain* 33, 87-107 (1988).
21. Gao, G.-P. et al. Novel adeno-associated viruses from rhesus monkeys as vectors for human gene therapy. *Proceedings of the National Academy of Sciences of the United States of America* 99, 11854-9 (2002).

22. Sohal, V. S., Zhang, F., Yizhar, O. & Deisseroth, K. Parvalbumin neurons and gamma rhythms enhance cortical circuit performance. *Nature* 459, 698-702 (2009).
23. Gold, M. S. Whole-Cell Recording in Isolated Primary Sensory Neurons. *Pain Research: Methods in Molecular Biology* 851, 73-97 (2012).
24. Hentschke, H. & Stüttgen, M. C. Computation of measures of effect size for neuroscience data sets. *The European Journal of Neuroscience* 34, 1887-94 (2011).
25. Chaplan, S. R., Bach, F. W., Pogrel, J. W., Chung, J. M. & Yaksh, T. L. Quantitative assessment of tactile allodynia in the rat paw. *Journal of Neuroscience Methods* 53, 55-63 (1994).
26. Dixon, W. J. Efficient Analysis of Experimental Observations. *Annual Review of Pharmacology and Toxicology* 20, 441-462 (1980).
27. Sommer, C. & Schafers, M. Painful mononeuropathy in C57BL/Wld mice with delayed Wallerian degeneration: differential effects of cytokine production and nerve regeneration on thermal and mechanical hypersensitivity. *Brain Research* 784, 154-162
28. Schindelin, J. et al. Fiji: an open-source platform for biological-image analysis. *Nature Methods* 9, 676-82 (2012).

Example 2: Intraneurally Injected AAV8 Selectively Transduces Neurons that Project to Spinal Cord Dorsal Columns and Deep Spinal Cord Laminae Large-diameter primary afferent neurons are responsible for mediating diverse sensory processes including pressure, vibration, pleasurable touch, and painful touch. In the context of pain research, these neurons are known to be significantly modified in various chronic pain disorders. Spontaneous ('ectopic') firing in these neurons is thought to be one of the major contributors to the development of inflammatory and neuropathic pain, either through their directly driving central pain pathways, or through modifying spinal cord circuitry to induce central sensitization. Optogenetic inhibition of these afferent neurons would reduce symptoms of neuropathic pain. Optogenetic stimulation of these afferent neurons may also act to reduce pain in some conditions, through multi-step circuit processes in the spinal cord that form part of the 'pain gate'. The data shown below indicate that an adeno-associated virus vector (AAV8) can specifically infect large-diameter primary afferent neurons that mediate sensation of touch.

Methods

All surgical and behavioral procedures were approved by the Stanford University Administrative Panel on Lab Animal Care. Under anesthesia, the sciatic nerve of C57BL/6 mice (6-8 weeks) was exposed; and 3-5 µl of AAV8-CMV-GFP (1-2E10 viral genomes (vg)) was injected into the exposed nerve. 2-4 weeks following injection, the mice were euthanized through transcardial perfusion. The mice were dissected and sectioned, and tissue from the spinal cords, nerves and paws was imaged.

Results

Figure 10:
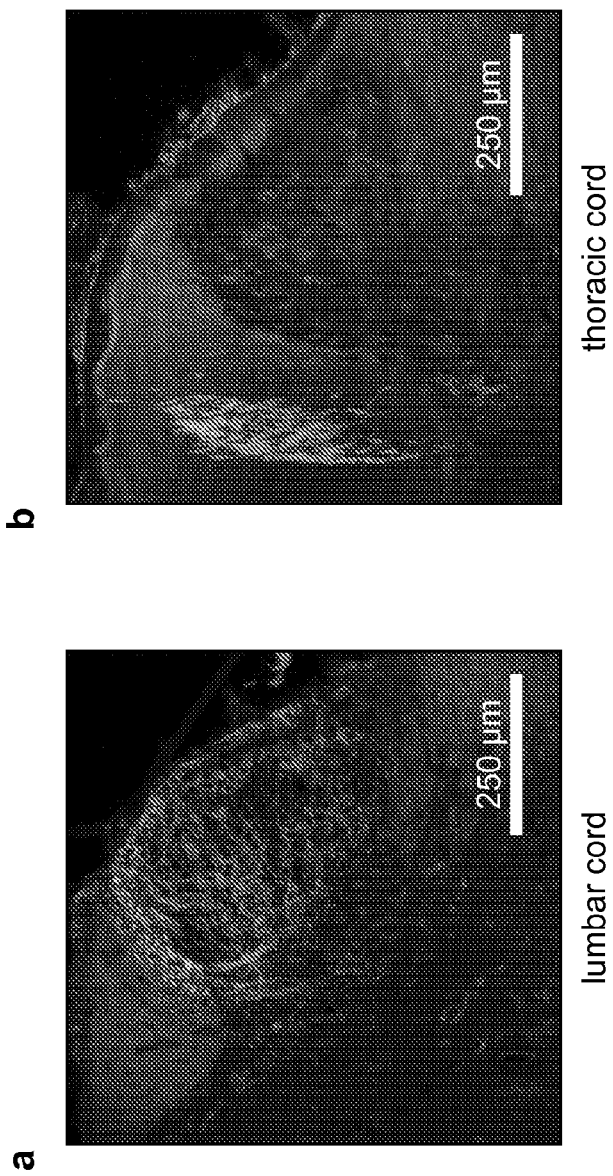
FIGS. 10A and 10B depict AAV8 transduction in the lumbar and thoracic spinal cord.

Primary afferent neurons successfully infected by AAV8-CMV-GFP projected to deep spinal cord laminae (FIG. 10A) in the lumbar spinal cord. In more rostral regions of the cord, expression was seen primarily in the fasciculus gracilis, in the dorsal columns (FIG. 10B). This expression persisted until the brainstem.

Example 3: Delivery of Optogenetic Proteins to Sensory Neurons of the Trigeminal Ganglion Neuropathic pain can arise in the trigeminal ganglion and is often characterized by episodic, lancinating, triggerable, often shock-like facial pain. The disease can result from infection (e.g. herpes virus), facial trauma, stroke or surgical nerve damage. The data in this example demonstrate delivery of the inhibitory opsin, eNpHR3.0, to the sensory neurons of the trigeminal ganglion in rats. The data presented in this example demonstrate that optogenetics can be used to control pain involving the trigeminal ganglion.

Methods

Under anesthesia, 10-week old Sprague Dawley rats were stereotaxically injected with $1 \times 10^{11}$ vg of AAV5-hSyn-eNpHR3.0 into the trigeminal ganglion. Animals were euthanized 4 weeks later, and the trigeminal ganglion was dissected, sectioned and imaged using a confocal microscope.

Results

Four weeks following direct injection of AAV5-eNpHR3.0-YFP, strong expression of the inhibitory protein in sensory neurons of the trigeminal ganglion was observed. These results demonstrate that primary sensory neurons other than those of spinal cord dorsal root ganglia can be targeted with opsins and can be inhibited to control pain transmitted by these neurons. The data also demonstrate the feasibility of opsin delivery using direct injection. The data are depicted in FIG. 11.

Figure 11:
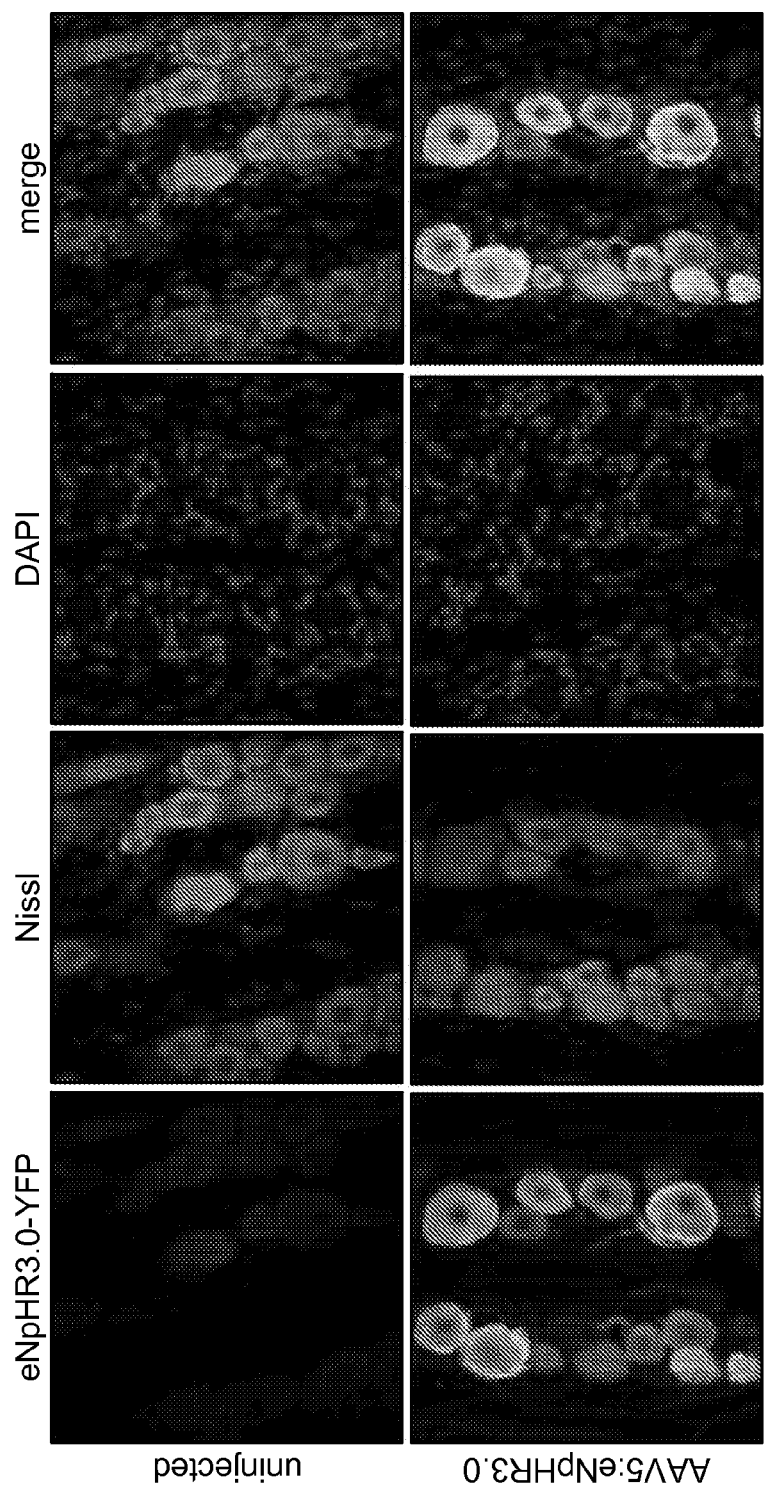
FIG. 11 depicts expression of eNpHR3.0 in trigeminal ganglion sensory neurons following direct injection into ganglion.

FIG. 11. Expression of eNpHR3.0 in trigeminal ganglion sensory neurons following direct injection into ganglion. eNpHR3.0 was fused to yellow fluorescent protein to facilitate visualization (green). Neurons were stained with Nissl (red). All cell nuclei were labelled with DAPI (blue).

Example 4: Delivery of Opsins and Inhibition of Pain in Animals with Prior Neuropathic Pain The data presented below demonstrate that AAV6 delivery of NpHR, following chronic constriction injury (CCI) and development of pain, can reduce pain.

Methods

Naïve C57B16 mice were habituated to the Von Frey mechanical testing procedure and then baseline mechanical thresholds recorded. Mice were then subjected to a CCI; 10 days following nerve injury, mechanical thresholds were recorded and only those animals that had developed neuropathic pain (as determined by a 25% or greater reduction in mechanical thresholds) were kept in the study. AAV6 expressing either NpHR or YFP under control of the human synapsin promoter ($5 \times 10^{10}$ vg total) was delivered to the sciatic nerve of the mice. Thirty days following NpHR or YFP delivery, mechanical thresholds were recorded in the presence or absence of yellow light application to the targeted paw.

Results

Thirty days following AAV6 delivery we observed that application of light to the targeted paw significantly increased mechanical threshold levels to pre-CCI levels in animals expressing NpHR but not YFP. The data are shown in FIG. 12.

Figure 12:
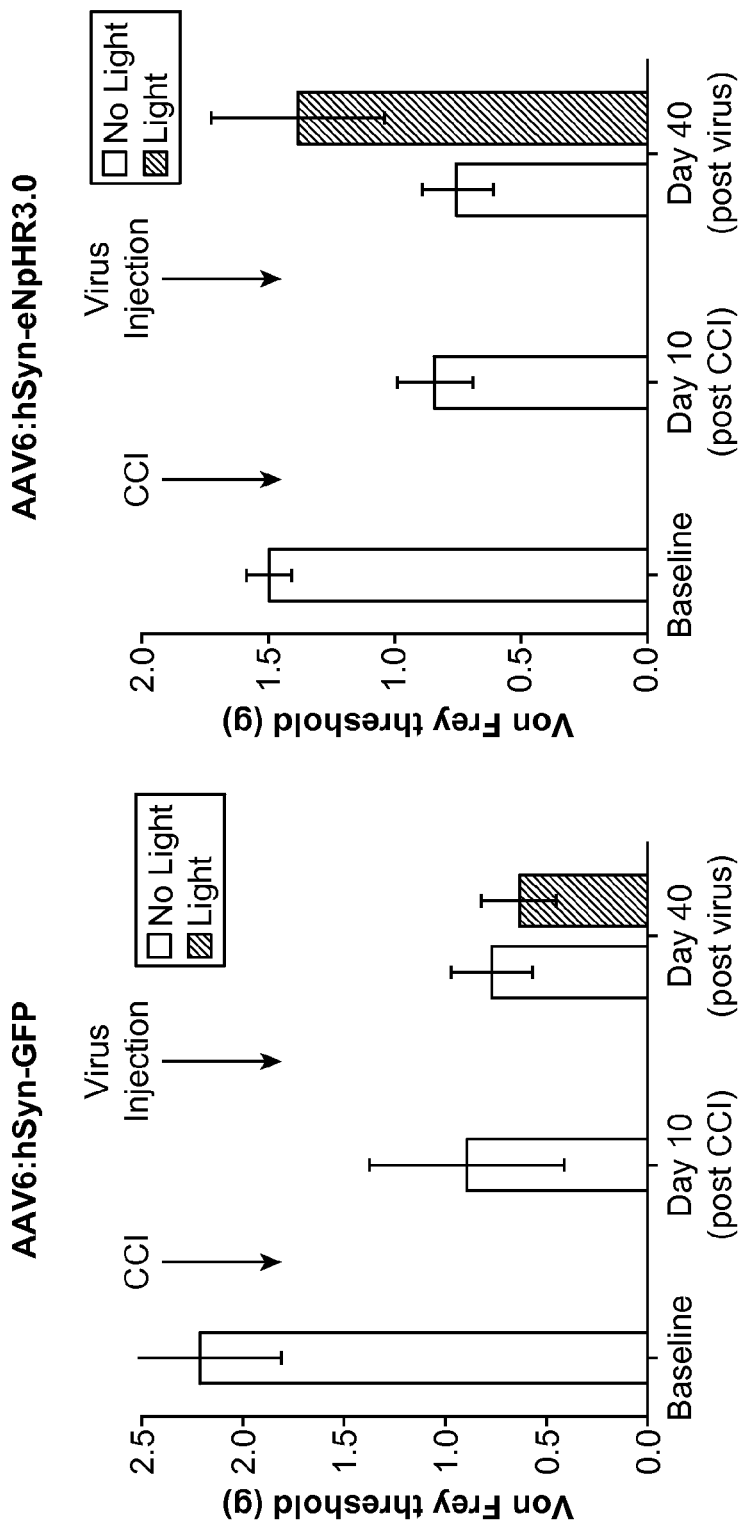
FIG. 12 depicts mechanical thresholds for mice expressing GFP or eNpHR3.0 in nociceptive fibers using AAV6.

FIG. 12. Mechanical thresholds for mice expressing GFP or eNpHR3.0 in nociceptive fibers using AAV6. Forty days following CCI thresholds were recorded in the presence or absence of yellow light. Animals in the eNpHR3.0 group had significantly higher mechanical thresholds in the presence of light ($p<0.05$). Mechanical thresholds in the YFP group were unchanged.

These results demonstrate that the optogenetic approach described here can be applied to nerves that have preexisting neuropathic pain.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for controlling pain in an individual, the method comprising:
   a) administering, via direct or intrathecal administration, to the individual a recombinant expression vector comprising a nucleotide sequence encoding a hyperpolarizing opsin polypeptide, wherein the opsin polypeptide is expressed in a nociceptor in the individual; and
   b) activating the opsin polypeptide with light, thereby controlling the pain in the individual.

2. The method of claim 1, wherein the light is delivered transdermally.

3. The method of claim 1, wherein the opsin comprises an amino acid sequence having at least about 75% amino acid sequence identity to one of SEQ ID NOs:1, 3, 4, 6, 15, and 16.

4. The method of claim 1, wherein the pain is neuropathic pain.

5. The method of claim 1, wherein the nociceptor is one that is normally activated by a thermal, mechanical, or chemical stimulus.

6. The method of claim 1, wherein the nucleotide sequence is operably linked to a promoter that provides for selective expression in a neuron.

7. The method of claim 1, wherein the individual is a mammal.

8. The method of claim 1, wherein activation of the opsin provides for an at least 10% reduction in pain.

9. The method of claim 1, wherein the light is delivered to a treatment site within the body.

10. The method of claim 1, wherein light is delivered through a light-generating device.

11. The method of claim 10, wherein the light-generating device is a light cuff or sleeve.

12. The method of claim 10, wherein the light-generating device comprises a light source and one or more optical fibers that is placed on the body of the individual.

13. The method of claim 10, wherein the light-generating device comprises a light-emitting diode.

14. The method of claim 13, wherein the light-emitting diode can generate blue light, green light, amber light, or yellow light.

15. The method of claim 1, wherein the opsin comprises an amino acid sequence having at least about 85% amino acid sequence identity to one of SEQ ID NOs:1, 3, 4, 6, 15, and 16.

16. The method of claim 1, wherein the opsin comprises an amino acid sequence having at least about 95% amino acid sequence identity to one of SEQ ID NOs:1, 3, 4, 6, 15, and 16.

17. The method of claim 1, wherein said introducing is via intrathecal administration.

18. The method of claim 1, wherein said introducing is via intraneural administration.

19. The method of claim 1, wherein the recombinant expression vector is a recombinant adeno associated virus (AAV) vector.

20. The method of claim 19, wherein the recombinant AAV vector is a recombinant AAV6 or a recombinant AAV8 vector.

* * * * *

SEQUENCE LISTING

```
<160> NUMBER OF SEQ ID NOS: 32

<210> SEQ ID NO 1
<211> LENGTH: 258
<212> TYPE: PRT
<213> ORGANISM: Halorubrum sodomense

<400> SEQUENCE: 1

Met Asp Pro Ile Ala Leu Gln Ala Gly Tyr Asp Leu Leu Gly Asp Gly
 1               5                  10                  15

Arg Pro Glu Thr Leu Trp Leu Gly Ile Gly Thr Leu Leu Met Leu Ile
                20                  25                  30

Gly Thr Phe Tyr Phe Leu Val Arg Gly Trp Gly Val Thr Asp Lys Asp
            35                  40                  45

Ala Arg Glu Tyr Tyr Ala Val Thr Ile Leu Val Pro Gly Ile Ala Ser
        50                  55                  60

Ala Ala Tyr Leu Ser Met Phe Phe Gly Ile Gly Leu Thr Glu Val Thr
 65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp

<210> SEQ ID NO 2
<211> LENGTH: 531
<212> TYPE: PRT
<213> ORGANISM: Artificial Sequence
<220> FEATURE:
```

<223> OTHER INFORMATION: Derived from Archaerhodopsin-3 from Halorubrum sodomense

<400> SEQUENCE: 2

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Leu Val Arg Gly Trp Gly Val Thr Asp Lys Asp
        35                  40                  45

Ala Arg Glu Tyr Tyr Ala Val Thr Ile Leu Val Pro Gly Ile Ala Ser
50                  55                  60

Ala Ala Tyr Leu Ser Met Phe Phe Gly Ile Gly Leu Thr Glu Val Thr
65                  70                  75                  80

Val Gly Gly Glu Met Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
            100                 105                 110

Val Asp Arg Val Thr Ile Gly Thr Leu Val Gly Val Asp Ala Leu Met
        115                 120                 125

Ile Val Thr Gly Leu Ile Gly Ala Leu Ser His Thr Ala Ile Ala Arg
130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ser Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
        195                 200                 205

Val Gly Leu Gly Ile Glu Thr Leu Leu Phe Met Val Leu Asp Val Thr
210                 215                 220

Ala Lys Val Gly Phe Gly Phe Ile Leu Leu Arg Ser Arg Ala Ile Leu
225                 230                 235                 240

Gly Asp Thr Glu Ala Pro Glu Pro Ser Ala Gly Ala Asp Val Ser Ala
                245                 250                 255

Ala Asp Arg Pro Val Val Ala Ala Ala Lys Ser Arg Ile Thr Ser
            260                 265                 270

Glu Gly Glu Tyr Ile Pro Leu Asp Gln Ile Asp Ile Asn Val Val Ser
        275                 280                 285

Lys Gly Glu Glu Leu Phe Thr Gly Val Val Pro Ile Leu Val Glu Leu
290                 295                 300

Asp Gly Asp Val Asn Gly His Lys Phe Ser Val Ser Gly Glu Gly Glu
305                 310                 315                 320

Gly Asp Ala Thr Tyr Gly Lys Leu Thr Leu Lys Phe Ile Cys Thr Thr
                325                 330                 335

Gly Lys Leu Pro Val Pro Trp Pro Thr Leu Val Thr Thr Phe Gly Tyr
            340                 345                 350

Gly Leu Gln Cys Phe Ala Arg Tyr Pro Asp His Met Lys Gln His Asp
        355                 360                 365

Phe Phe Lys Ser Ala Met Pro Glu Gly Tyr Val Gln Glu Arg Thr Ile
370                 375                 380

Phe Phe Lys Asp Asp Gly Asn Tyr Lys Thr Arg Ala Glu Val Lys Phe
385                 390                 395                 400
```

```
Glu Gly Asp Thr Leu Val Asn Arg Ile Glu Leu Lys Gly Ile Asp Phe
                405                 410                 415

Lys Glu Asp Gly Asn Ile Leu Gly His Lys Leu Glu Tyr Asn Tyr Asn
            420                 425                 430

Ser His Asn Val Tyr Ile Met Ala Asp Lys Gln Lys Asn Gly Ile Lys
                435                 440                 445

Val Asn Phe Lys Ile Arg His Asn Ile Glu Asp Gly Ser Val Gln Leu
    450                 455                 460

Ala Asp His Tyr Gln Gln Asn Thr Pro Ile Gly Asp Gly Pro Val Leu
465                 470                 475                 480

Leu Pro Asp Asn His Tyr Leu Ser Tyr Gln Ser Ala Leu Ser Lys Asp
                485                 490                 495

Pro Asn Glu Lys Arg Asp His Met Val Leu Leu Glu Phe Val Thr Ala
            500                 505                 510

Ala Gly Ile Thr Leu Gly Met Asp Glu Leu Tyr Lys Phe Cys Tyr Glu
            515                 520                 525

Asn Glu Val
    530
```

<210> SEQ ID NO 3
<211> LENGTH: 248
<212> TYPE: PRT
<213> ORGANISM: Halorubrum sp. TP009

<400> SEQUENCE: 3

```
Met Asp Pro Ile Ala Leu Gln Ala Gly Tyr Asp Leu Leu Gly Asp Gly
1               5                   10                  15

Arg Pro Glu Thr Leu Trp Leu Gly Ile Gly Thr Leu Leu Met Leu Ile
            20                  25                  30

Gly Thr Phe Tyr Phe Ile Val Lys Gly Trp Gly Val Thr Asp Lys Glu
        35                  40                  45

Ala Arg Glu Tyr Tyr Ser Ile Thr Ile Leu Val Pro Gly Ile Ala Ser
    50                  55                  60

Ala Ala Tyr Leu Ser Met Phe Phe Gly Ile Gly Leu Thr Glu Val Thr
65                  70                  75                  80

Val Ala Gly Glu Val Leu Asp Ile Tyr Tyr Ala Arg Tyr Ala Asp Trp
                85                  90                  95

Leu Phe Thr Thr Pro Leu Leu Leu Leu Asp Leu Ala Leu Leu Ala Lys
                100                 105                 110

Val Asp Arg Val Ser Ile Gly Thr Leu Val Gly Val Asp Ala Leu Met
            115                 120                 125

Ile Val Thr Gly Leu Ile Gly Ala Leu Ser His Thr Pro Leu Ala Arg
    130                 135                 140

Tyr Ser Trp Trp Leu Phe Ser Thr Ile Cys Met Ile Val Val Leu Tyr
145                 150                 155                 160

Phe Leu Ala Thr Ser Leu Arg Ala Ala Lys Glu Arg Gly Pro Glu
                165                 170                 175

Val Ala Ser Thr Phe Asn Thr Leu Thr Ala Leu Val Leu Val Leu Trp
            180                 185                 190

Thr Ala Tyr Pro Ile Leu Trp Ile Ile Gly Thr Glu Gly Ala Gly Val
                195                 200                 205

Val Gly Leu Gly Ile Glu Thr Leu Leu Phe Met Val Leu Asp Val Thr
    210                 215                 220

Ala Lys Val Gly Phe Gly Phe Ile Leu Leu Arg Ser Arg Ala Ile Leu
```

```
                225                 230                 235                 240

Gly Asp Thr Glu Ala Pro Glu Pro
                245

<210> SEQ ID NO 4
<211> LENGTH: 223
<212> TYPE: PRT
<213> ORGANISM: Guillardia theta

<400> SEQUENCE: 4

Ala Ser Ser Phe Gly Lys Ala Leu Leu Glu Phe Val Phe Ile Val Phe
1               5                   10                  15

Ala Cys Ile Thr Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
    50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
        115                 120                 125

Phe Phe Gly Met Cys Trp Phe Leu His Ile Ile Phe Ala Leu Gly Lys
    130                 135                 140

Ser Trp Ala Glu Ala Ala Lys Ala Lys Gly Gly Asp Ser Ala Ser Val
145                 150                 155                 160

Tyr Ser Lys Ile Ala Gly Ile Thr Val Ile Thr Trp Phe Cys Tyr Pro
                165                 170                 175

Val Val Trp Val Phe Ala Glu Gly Phe Gly Asn Phe Ser Val Thr Phe
            180                 185                 190

Glu Val Leu Ile Tyr Gly Val Leu Asp Val Ile Ser Lys Ala Val Phe
        195                 200                 205

Gly Leu Ile Leu Met Ser Gly Ala Ala Thr Gly Tyr Glu Ser Ile
    210                 215                 220

<210> SEQ ID NO 5
<211> LENGTH: 262
<212> TYPE: PRT
<213> ORGANISM: Oxyrrhis marina

<400> SEQUENCE: 5

Met Ala Pro Leu Ala Gln Asp Trp Thr Tyr Ala Glu Trp Ser Ala Val
1               5                   10                  15

Tyr Asn Ala Leu Ser Phe Gly Ile Ala Gly Met Gly Ser Ala Thr Ile
            20                  25                  30

Phe Phe Trp Leu Gln Leu Pro Asn Val Thr Lys Asn Tyr Arg Thr Ala
        35                  40                  45

Leu Thr Ile Thr Gly Ile Val Thr Leu Ile Ala Thr Tyr His Tyr Phe
    50                  55                  60

Arg Ile Phe Asn Ser Trp Val Ala Ala Phe Asn Val Gly Leu Gly Val
65                  70                  75                  80

Asn Gly Ala Tyr Glu Val Thr Val Ser Gly Thr Pro Phe Asn Asp Ala
```

```
                85                  90                  95
Tyr Arg Tyr Val Asp Trp Leu Leu Thr Val Pro Leu Leu Val Glu
            100                 105                 110

Leu Ile Leu Val Met Lys Leu Pro Ala Lys Glu Thr Val Cys Leu Ala
            115                 120                 125

Trp Thr Leu Gly Ile Ala Ser Ala Val Met Val Ala Leu Gly Tyr Pro
            130                 135                 140

Gly Glu Ile Gln Asp Asp Leu Ser Val Arg Trp Phe Trp Ala Cys
145                 150                 155                 160

Ala Met Val Pro Phe Val Tyr Val Gly Thr Leu Val Val Gly Leu
                165                 170                 175

Gly Ala Ala Thr Ala Lys Gln Pro Glu Gly Val Val Asp Leu Val Ser
                180                 185                 190

Ala Ala Arg Tyr Leu Thr Val Val Ser Trp Leu Thr Tyr Pro Phe Val
                195                 200                 205

Tyr Ile Val Lys Asn Ile Gly Leu Ala Gly Ser Thr Ala Thr Met Tyr
                210                 215                 220

Glu Gln Ile Gly Tyr Ser Ala Ala Asp Val Thr Ala Lys Ala Val Phe
225                 230                 235                 240

Gly Val Leu Ile Trp Ala Ile Ala Asn Ala Lys Ser Arg Leu Glu Glu
                245                 250                 255

Glu Gly Lys Leu Arg Ala
                260

<210> SEQ ID NO 6
<211> LENGTH: 313
<212> TYPE: PRT
<213> ORGANISM: Leptosphaeria maculans

<400> SEQUENCE: 6

Met Ile Val Asp Gln Phe Glu Glu Val Leu Met Lys Thr Ser Gln Leu
1               5                   10

```
Tyr Thr Ile Ala Cys Ile Ala Tyr Ile Phe Val Val Trp His Leu Val
            195                 200                 205

Leu Asn Gly Gly Ala Asn Ala Arg Val Lys Gly Glu Lys Leu Arg Ser
        210                 215                 220

Phe Phe Val Ala Ile Gly Ala Tyr Thr Leu Ile Leu Trp Thr Ala Tyr
225                 230                 235                 240

Pro Ile Val Trp Gly Leu Ala Asp Gly Ala Arg Lys Ile Gly Val Asp
                245                 250                 255

Gly Glu Ile Ile Ala Tyr Ala Val Leu Asp Val Leu Ala Lys Gly Val
                260                 265                 270

Phe Gly Ala Trp Leu Leu Val Thr His Ala Asn Leu Arg Glu Ser Asp
            275                 280                 285

Val Glu Leu Asn Gly Phe Trp Ala Asn Gly Leu Asn Arg Glu Gly Ala
        290                 295                 300

Ile Arg Ile Gly Glu Asp Asp Gly Ala
305                 310
```

```
<210> SEQ ID NO 7
<211> LENGTH: 589
<212> TYPE: PRT
<213> ORGANISM: Artificial Sequence
<220> FEATURE:
<223> OTHER INFORMATION: Derived from L. maculans rhodopsin

<400> SEQUENCE: 7

Met Ile Val Asp Gln Phe Glu Glu Val Leu Met Lys Thr Ser Gln Leu
1               5                   10                  15

Phe Pro Leu Pro Thr Ala Thr Gln Ser Ala Gln Pro Thr His Val Ala
            20                  25                  30

Pro Val Pro Thr Val Leu Pro Asp Thr Pro Ile Tyr Glu Thr Val Gly
        35                  40                  45

Asp Ser Gly Ser Lys Thr Leu Trp Val Phe Val Leu Met Leu Ile
    50                  55                  60

Ala Ser Ala Ala Phe Thr Ala Leu Ser Trp Lys Ile Pro Val Asn Arg
65                  70                  75                  80

Arg Leu Tyr His Val Ile Thr Thr Ile Thr Leu Thr Ala Ala Leu
                85                  90                  95

Ser Tyr Phe Ala Met Ala Thr Gly His Gly Val Ala Leu Asn Lys Ile
                100                 105                 110

Val Ile Arg Thr Gln His Asp His Val Pro Asp Thr Tyr Glu Thr Val
            115                 120                 125

Tyr Arg Gln Val Tyr Tyr Ala Arg Tyr Ile Asp Trp Ala Ile Thr Thr
        130                 135                 140

Pro Leu Leu Leu Leu Asp Leu Gly Leu Leu Ala Gly Met Ser Gly Ala
145                 150                 155                 160

His Ile Phe Met Ala Ile Val Ala Asp Leu Ile Met Val Leu Thr Gly
                165                 170                 175

Leu Phe Ala Ala Phe Gly Ser Glu Gly Thr Pro Gln Lys Trp Gly Trp
                180                 185                 190

Tyr Thr Ile Ala Cys Ile Ala Tyr Ile Phe Val Val Trp His Leu Val
            195                 200                 205

Leu Asn Gly Gly Ala Asn Ala Arg Val Lys Gly Glu Lys Leu Arg Ser
        210                 215                 220

Phe Phe Val Ala Ile Gly Ala Tyr Thr Leu Ile Leu Trp Thr Ala Tyr
225                 230                 235                 240
```

Pro Ile Val Trp Gly Leu Ala Asp Gly Ala Arg Lys Ile Gly Val Asp
            245                 250                 255

Gly Glu Ile Ile Ala Tyr Ala Val Leu Asp Val Leu Ala Lys Gly Val
        260                 265                 270

Phe Gly Ala Trp Leu Leu Val Thr His Ala Asn Leu Arg Glu Ser Asp
    275                 280                 285

Val Glu Leu Asn Gly Phe Trp Ala Asn Gly Leu Asn Arg Glu Gly Ala
290                 295                 300

Ile Arg Ile Gly Glu Asp Asp Gly Ala Arg Pro Val Val Ala Val Ser
305                 310                 315                 320

Lys Ala Ala Ala Lys Ser Arg Ile Thr Ser Glu Gly Glu Tyr Ile Pro
                325                 330                 335

Leu Asp Gln Ile Asp Ile Asn Val Val Ser Lys Gly Glu Glu Leu Phe
            340                 345                 350

Thr Gly Val Val Pro Ile Leu Val Glu Leu Asp Gly Asp Val Asn Gly
        355                 360                 365

His Lys Phe Ser Val Ser Gly Glu Gly Glu Gly Asp Ala Thr Tyr Gly
    370                 375                 380

Lys Leu Thr Leu Lys Phe Ile Cys Thr Thr Gly Lys Leu Pro Val Pro
385                 390                 395                 400

Trp Pro Thr Leu Val Thr Thr Phe Gly Tyr Gly Leu Gln Cys Phe Ala
                405                 410                 415

Arg Tyr Pro Asp His Met Lys Gln His Asp Phe Phe Lys Ser Ala Met
            420                 425                 430

Pro Glu Gly Tyr Val Gln Glu Arg Thr Ile Phe Phe Lys Asp Asp Gly
        435                 440                 445

Asn Tyr Lys Thr Arg Ala Glu Val Lys Phe Glu Gly Asp Thr Leu Val
    450                 455                 460

Asn Arg Ile Glu Leu Lys Gly Ile Asp Phe Lys Glu Asp Gly Asn Ile
465                 470                 475                 480

Leu Gly His Lys Leu Glu Tyr Asn Tyr Asn Ser His Asn Val Tyr Ile
                485                 490                 495

Met Ala Asp Lys Gln Lys Asn Gly Ile Lys Val Asn Phe Lys Ile Arg
            500                 505                 510

His Asn Ile Glu Asp Gly Ser Val Gln Leu Ala Asp His Tyr Gln Gln
        515                 520                 525

Asn Thr Pro Ile Gly Asp Gly Pro Val Leu Leu Pro Asp Asn His Tyr
    530                 535                 540

Leu Ser Tyr Gln Ser Ala Leu Ser Lys Asp Pro Asn Glu Lys Arg Asp
545                 550                 555                 560

His Met Val Leu Leu Glu Phe Val Thr Ala Ala Gly Ile Thr Leu Gly
                565                 570                 575

Met Asp Glu Leu Tyr Lys Phe Cys Tyr Glu Asn Glu Val
            580                 585

<210> SEQ ID NO 8
<211> LENGTH: 310
<212> TYPE: PRT
<213> ORGANISM: Chlamydomonas reinhardtii

<400> SEQUENCE: 8

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

-continued

```
Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
         50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 9
<211> LENGTH: 310
<212> TYPE: PRT
<213> ORGANISM: Artificial Sequence
<220> FEATURE:
<223> OTHER INFORMATION: Derived from Chlamydomonas reinhardtii ChR2

<400> SEQUENCE: 9

Met Asp Tyr Gly Gly Ala Leu Ser Ala Val Gly Arg Glu Leu Leu Phe
  1               5                  10                  15

Val Thr Asn Pro Val Val Asn Gly Ser Val Leu Val Pro Glu Asp
             20                  25                  30

Gln Cys Tyr Cys Ala Gly Trp Ile Glu Ser Arg Gly Thr Asn Gly Ala
             35                  40                  45

Gln Thr Ala Ser Asn Val Leu Gln Trp Leu Ala Ala Gly Phe Ser Ile
         50                  55                  60

Leu Leu Leu Met Phe Tyr Ala Tyr Gln Thr Trp Lys Ser Thr Cys Gly
 65                  70                  75                  80
```

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
                115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
290                 295                 300

Glu Ala Gly Ala Val Pro
305                 310

<210> SEQ ID NO 10
<211> LENGTH: 310
<212> TYPE: PRT
<213> ORGANISM: Artificial Sequence
<220> FEATURE:
<223> OTHER INFORMATION: Derived from Chlamydomonas reinhardtii ChR2

<400> SEQUENCE: 10

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
                50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
                100                 105                 110

Gly His Arg Val Gln Trp Leu Arg Tyr Ala Glu Trp Leu Leu Thr Ser
                115                 120                 125

```
Pro Val Ile Leu Ile His Leu Ser Asn Leu Thr Gly Leu Ser Asn Asp
    130                 135                 140

Tyr Ser Arg Arg Thr Met Gly Leu Leu Val Ser Ala Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310

<210> SEQ ID NO 11
<211> LENGTH: 344
<212> TYPE: PRT
<213> ORGANISM: Artificial Sequence
<220> FEATURE:
<223> OTHER INFORMATION: Derived from Chlamydomonas reinhardtii and
      Volvox carteri channelrhodopsins.

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
```

```
                165                 170                 175
Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
            245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
            290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
            325                 330                 335

Thr Leu Val Ala Glu Glu Glu Asp
            340

<210> SEQ ID NO 12
<211> LENGTH: 344
<212> TYPE: PRT
<213> ORGANISM: Artificial Sequence
<220> FEATURE:
<223> OTHER INFORMATION: Derived from Chlamydomonas reinhardtii and
      Volvox carteri channelrhodopsins.

<400> SEQUENCE: 12

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
            50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
            85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Leu Leu Ile His Leu Ser Asn
            165                 170                 175
```

```
Leu Thr Gly Leu Lys Asp Asp Tyr Ser Lys Arg Thr Met Gly Leu Leu
                180                 185                 190

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
        210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
        275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Asp
            340

<210> SEQ ID NO 13
<211> LENGTH: 344
<212> TYPE: PRT
<213> ORGANISM: Artificial Sequence
<220> FEATURE:
<223> OTHER INFORMATION: Derived from Chlamydomonas reinhardtii and
      Volvox carteri channelrhodopsins.

<400> SEQUENCE: 13

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190
```

Val Ser Asp Val Gly Cys Ile Val Trp Gly Ala Thr Ser Ala Met Cys
            195                 200                 205

Thr Gly Trp Thr Lys Ile Leu Phe Phe Leu Ile Ser Leu Ser Tyr Gly
    210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                245                 250                 255

Thr Phe Phe Val Ala Trp Gly Met Phe Pro Val Leu Phe Leu Leu Gly
            260                 265                 270

Thr Glu Gly Phe Gly His Ile Ser Pro Tyr Gly Ser Ala Ile Gly His
            275                 280                 285

Ser Ile Leu Asp Leu Ile Ala Lys Asn Met Trp Gly Val Leu Gly Asn
    290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                325                 330                 335

Thr Leu Val Ala Glu Glu Glu Asp
            340

<210> SEQ ID NO 14
<211> LENGTH: 344
<212> TYPE: PRT
<213> ORGANISM: Artificial Sequence
<220> FEATURE:
<223> OTHER INFORMATION: Derived from Chlamydomonas reinhardtii and
      Volvox carteri channelrhodopsins.

<400> SEQUENCE: 14

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Thr Ile Tyr Val Ala Thr Ile
            115                 120                 125

Glu Met Ile Lys Phe Ile Ile Glu Tyr Phe His Glu Phe Asp Glu Pro
            130                 135                 140

Ala Val Ile Tyr Ser Ser Asn Gly Asn Lys Thr Val Trp Leu Arg Tyr
145                 150                 155                 160

Ala Thr Trp Leu Leu Thr Cys Pro Val Leu Leu Ile His Leu Ser Asn
                165                 170                 175

Leu Thr Gly Leu Lys Asp Asp Tyr Ser Lys Arg Thr Met Gly Leu Leu
            180                 185                 190

Val Ser Asp Val Gly Cys Ile Val Trp Gly Ala Thr Ser Ala Met Cys

```
            195                 200                 205
Thr Gly Trp Thr Lys Ile Leu Phe Phe Leu Ile Ser Leu Ser Tyr Gly
            210                 215                 220

Met Tyr Thr Tyr Phe His Ala Ala Lys Val Tyr Ile Glu Ala Phe His
225                 230                 235                 240

Thr Val Pro Lys Gly Ile Cys Arg Glu Leu Val Arg Val Met Ala Trp
                    245                 250                 255

Thr Phe Phe Val Ala Trp Gly Met Phe Pro Val Leu Phe Leu Leu Gly
                260                 265                 270

Thr Glu Gly Phe Gly His Ile Ser Pro Tyr Gly Ser Ala Ile Gly His
                275                 280                 285

Ser Ile Leu Asp Leu Ile Ala Lys Asn Met Trp Gly Val Leu Gly Asn
        290                 295                 300

Tyr Leu Arg Val Lys Ile His Glu His Ile Leu Leu Tyr Gly Asp Ile
305                 310                 315                 320

Arg Lys Lys Gln Lys Ile Thr Ile Ala Gly Gln Glu Met Glu Val Glu
                    325                 330                 335

Thr Leu Val Ala Glu Glu Glu Asp
                340

<210> SEQ ID NO 15
<211> LENGTH: 365
<212> TYPE: PRT
<213> ORGANISM: Dunaliella salina

<400> SEQUENCE: 15

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
                20                  25                  30

Glu Arg Arg Pro Pro Ser Glu Arg Asn Thr Pro Tyr Ala Asn Ile Lys
            35                  40                  45

Lys Val Pro Asn Ile Thr Glu Pro Asn Ala Asn Val Gln Leu Asp Gly
        50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
            100                 105                 110

Ile Val Phe Ala Ile Cys Ile Val Gln Leu Val Tyr Phe Met Phe Ala
        115                 120                 125

Ala Trp Lys Ala Thr Val Gly Trp Glu Glu Val Tyr Val Asn Ile Ile
    130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
            180                 185                 190

Leu Thr Gly Leu Lys Gly Asp Tyr Ser Lys Arg Thr Met Gly Leu Leu
        195                 200                 205

Val Ser Asp Ile Gly Thr Ile Val Phe Gly Thr Ser Ala Ala Leu Ala
    210                 215                 220
```

```
Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
            260                 265                 270

Trp Thr Tyr Phe Val Ser Trp Ala Met Phe Pro Ile Leu Phe Ile Leu
        275                 280                 285

Gly Arg Glu Gly Phe Gly His Ile Thr Tyr Phe Gly Ser Ser Ile Gly
    290                 295                 300

His Phe Ile Leu Glu Ile Phe Ser Lys Asn Leu Trp Ser Leu Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
                340                 345                 350

Glu Glu Tyr Val Asp Ser Asn Asp Lys Asp Ser Asp Val
                355                 360                 365

<210> SEQ ID NO 16
<211> LENGTH: 273
<212> TYPE: PRT
<213> ORGANISM: Natromonas pharaonis

<400> SEQUENCE: 16

Val Thr Gln Arg Glu Leu Phe Glu Phe Val Leu Asn Asp Pro Leu Leu
1               5                   10                  15

Ala Ser Ser Leu Tyr Ile Asn Ile Ala Leu Ala Gly Leu Ser Ile Leu
                20                  25                  30

Leu Phe Val Phe Met Thr Arg Gly Leu Asp Asp Pro Arg Ala Lys Leu
            35                  40                  45

Ile Ala Val Ser Thr Ile Leu Val Pro Val Val Ser Ile Ala Ser Tyr
        50                  55                  60

Thr Gly Leu Ala Ser Gly Leu Thr Ile Ser Val Leu Glu Met Pro Ala
65                  70                  75                  80

Gly His Phe Ala Glu Gly Ser Ser Val Met Leu Gly Gly Glu Glu Val
                85                  90                  95

Asp Gly Val Val Thr Met Trp Gly Arg Tyr Leu Thr Trp Ala Leu Ser
            100                 105                 110

Thr Pro Met Ile Leu Leu Ala Leu Gly Leu Leu Ala Gly Ser Asn Ala
        115                 120                 125

Thr Lys Leu Phe Thr Ala Ile Thr Phe Asp Ile Ala Met Cys Val Thr
    130                 135                 140

Gly Leu Ala Ala Ala Leu Thr Thr Ser Ser His Leu Met Arg Trp Phe
145                 150                 155                 160

Trp Tyr Ala Ile Ser Cys Ala Cys Phe Leu Val Val Leu Tyr Ile Leu
                165                 170                 175

Leu Val Glu Trp Ala Gln Asp Ala Lys Ala Ala Gly Thr Ala Asp Met
            180                 185                 190

Phe Asn Thr Leu Lys Leu Leu Thr Val Val Met Trp Leu Gly Tyr Pro
        195                 200                 205

Ile Val Trp Ala Leu Gly Val Glu Gly Ile Ala Val Leu Pro Val Gly
    210                 215                 220

Val Thr Ser Trp Gly Tyr Ser Phe Leu Asp Ile Val Ala Lys Tyr Ile
225                 230                 235                 240
```

```
Phe Ala Phe Leu Leu Leu Asn Tyr Leu Thr Ser Asn Glu Ser Val Val
                245                 250                 255

Ser Gly Ser Ile Leu Asp Val Pro Ser Ala Ser Gly Thr Pro Ala Asp
                260                 265                 270

Asp

<210> SEQ ID NO 17
<211> LENGTH: 559
<212> TYPE: PRT
<213> ORGANISM: Artificial Sequence
<220> FEATURE:
<223> OTHER INFORMATION: Derived from Natromonas pharaonis NpHR

<400> SEQUENCE: 17

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
                35                  40                  45

Ile Leu Leu Phe Val Phe Met Thr Arg Gly Leu Asp Asp Pro Arg Ala
        50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
                115                 120                 125

Leu Ser Thr Pro Met Ile Leu Leu Ala Leu Gly Leu Leu Ala Gly Ser
                130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
                180                 185                 190

Ile Leu Leu Val Glu Trp Ala Gln Asp Ala Lys Ala Ala Gly Thr Ala
                195                 200                 205

Asp Met Phe Asn Thr Leu Lys Leu Leu Thr Val Val Met Trp Leu Gly
                210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
                275                 280                 285

Ala Asp Asp Ala Ala Ala Lys Ser Arg Ile Thr Ser Glu Gly Glu Tyr
                290                 295                 300

Ile Pro Leu Asp Gln Ile Asp Ile Asn Val Val Ser Lys Gly Glu Glu
305                 310                 315                 320
```

```
Leu Phe Thr Gly Val Pro Ile Leu Val Glu Leu Asp Gly Asp Val
            325                 330                 335

Asn Gly His Lys Phe Ser Val Ser Gly Glu Gly Glu Gly Asp Ala Thr
            340                 345                 350

Tyr Gly Lys Leu Thr Leu Lys Phe Ile Cys Thr Thr Gly Lys Leu Pro
            355                 360                 365

Val Pro Trp Pro Thr Leu Val Thr Thr Phe Gly Tyr Gly Leu Gln Cys
            370                 375                 380

Phe Ala Arg Tyr Pro Asp His Met Lys Gln His Asp Phe Phe Lys Ser
385                 390                 395                 400

Ala Met Pro Glu Gly Tyr Val Gln Glu Arg Thr Ile Phe Phe Lys Asp
            405                 410                 415

Asp Gly Asn Tyr Lys Thr Arg Ala Glu Val Lys Phe Glu Gly Asp Thr
            420                 425                 430

Leu Val Asn Arg Ile Glu Leu Lys Gly Ile Asp Phe Lys Glu Asp Gly
            435                 440                 445

Asn Ile Leu Gly His Lys Leu Glu Tyr Asn Tyr Asn Ser His Asn Val
            450                 455                 460

Tyr Ile Met Ala Asp Lys Gln Lys Asn Gly Ile Lys Val Asn Phe Lys
465                 470                 475                 480

Ile Arg His Asn Ile Glu Asp Gly Ser Val Gln Leu Ala Asp His Tyr
            485                 490                 495

Gln Gln Asn Thr Pro Ile Gly Asp Gly Pro Val Leu Leu Pro Asp Asn
            500                 505                 510

His Tyr Leu Ser Tyr Gln Ser Ala Leu Ser Lys Asp Pro Asn Glu Lys
            515                 520                 525

Arg Asp His Met Val Leu Leu Glu Phe Val Thr Ala Ala Gly Ile Thr
            530                 535                 540

Leu Gly Met Asp Glu Leu Tyr Lys Phe Cys Tyr Glu Asn Glu Val
545                 550                 555

<210> SEQ ID NO 18
<211> LENGTH: 542
<212> TYPE: PRT
<213> ORGANISM: Artificial Sequence
<220> FEATURE:
<223> OTHER INFORMATION: Derived from Natromonas pharaonis NpHR

<400> SEQUENCE: 18

Met Val Thr Gln Arg Glu Leu Phe Glu Phe Val Leu Asn Asp Pro Leu
1               5                   10                  15

Leu Ala Ser Ser Leu Tyr Ile Asn Ile Ala Leu Ala Gly Leu Ser Ile
            20                  25                  30

Leu Leu Phe Val Phe Met Thr Arg Gly Leu Asp Asp Pro Arg Ala Lys
            35                  40                  45

Leu Ile Ala Val Ser Thr Ile Leu Val Pro Val Ser Ile Ala Ser
            50                  55                  60

Tyr Thr Gly Leu Ala Ser Gly Leu Thr Ile Ser Val Leu Glu Met Pro
65                  70                  75                  80

Ala Gly His Phe Ala Glu Gly Ser Ser Val Met Leu Gly Gly Glu Glu
            85                  90                  95

Val Asp Gly Val Val Thr Met Trp Gly Arg Tyr Leu Thr Trp Ala Leu
            100                 105                 110

Ser Thr Pro Met Ile Leu Leu Ala Leu Gly Leu Leu Ala Gly Ser Asn
            115                 120                 125
```

-continued

```
Ala Thr Lys Leu Phe Thr Ala Ile Thr Phe Asp Ile Ala Met Cys Val
130                 135                 140
Thr Gly Leu Ala Ala Leu Thr Thr Ser Ser His Leu Met Arg Trp
145                 150                 155                 160
Phe Trp Tyr Ala Ile Ser Cys Ala Cys Phe Leu Val Val Leu Tyr Ile
                    165                 170                 175
Leu Leu Val Glu Trp Ala Gln Asp Ala Lys Ala Ala Gly Thr Ala Asp
                180                 185                 190
Met Phe Asn Thr Leu Lys Leu Leu Thr Val Val Met Trp Leu Gly Tyr
                195                 200                 205
Pro Ile Val Trp Ala Leu Gly Val Glu Gly Ile Ala Val Leu Pro Val
210                 215                 220
Gly Val Thr Ser Trp Gly Tyr Ser Phe Leu Asp Ile Val Ala Lys Tyr
225                 230                 235                 240
Ile Phe Ala Phe Leu Leu Leu Asn Tyr Leu Thr Ser Asn Glu Ser Val
                    245                 250                 255
Val Ser Gly Ser Ile Leu Asp Val Pro Ser Ala Ser Gly Thr Pro Ala
                260                 265                 270
Asp Asp Ala Ala Ala Lys Ser Arg Ile Thr Ser Glu Gly Glu Tyr Ile
                275                 280                 285
Pro Leu Asp Gln Ile Asp Ile Asn Val Val Ser Lys Gly Glu Glu Leu
                290                 295                 300
Phe Thr Gly Val Val Pro Ile Leu Val Glu Leu Asp Gly Asp Val Asn
305                 310                 315                 320
Gly His Lys Phe Ser Val Ser Gly Glu Gly Glu Gly Asp Ala Thr Tyr
                    325                 330                 335
Gly Lys Leu Thr Leu Lys Phe Ile Cys Thr Thr Gly Lys Leu Pro Val
                340                 345                 350
Pro Trp Pro Thr Leu Val Thr Thr Phe Gly Tyr Gly Leu Gln Cys Phe
                355                 360                 365
Ala Arg Tyr Pro Asp His Met Lys Gln His Asp Phe Phe Lys Ser Ala
                370                 375                 380
Met Pro Glu Gly Tyr Val Gln Glu Arg Thr Ile Phe Phe Lys Asp Asp
385                 390                 395                 400
Gly Asn Tyr Lys Thr Arg Ala Glu Val Lys Phe Glu Gly Asp Thr Leu
                    405                 410                 415
Val Asn Arg Ile Glu Leu Lys Gly Ile Asp Phe Lys Glu Asp Gly Asn
                420                 425                 430
Ile Leu Gly His Lys Leu Glu Tyr Asn Tyr Asn Ser His Asn Val Tyr
                435                 440                 445
Ile Met Ala Asp Lys Gln Lys Asn Gly Ile Lys Val Asn Phe Lys Ile
450                 455                 460
Arg His Asn Ile Glu Asp Gly Ser Val Gln Leu Ala Asp His Tyr Gln
465                 470                 475                 480
Gln Asn Thr Pro Ile Gly Asp Gly Pro Val Leu Leu Pro Asp Asn His
                    485                 490                 495
Tyr Leu Ser Tyr Gln Ser Ala Leu Ser Lys Asp Pro Asn Glu Lys Arg
                500                 505                 510
Asp His Met Val Leu Leu Glu Phe Val Thr Ala Ala Gly Ile Thr Leu
                515                 520                 525
Gly Met Asp Glu Leu Tyr Lys Phe Cys Tyr Glu Asn Glu Val
530                 535                 540
```

-continued

```
<210> SEQ ID NO 19
<211> LENGTH: 300
<212> TYPE: PRT
<213> ORGANISM: Volvox carteri

<400> SEQUENCE: 19
```

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
        35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Ser Gly Asn Gly Val Val
            100                 105                 110

Trp Met Arg Tyr Gly Glu Trp Leu Leu Thr Cys Pro Val Leu Leu Ile
        115                 120                 125

His Leu Ser Asn Leu Thr Gly Leu Lys Asp Asp Tyr Ser Lys Arg Thr
    130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

```
<210> SEQ ID NO 20
<211> LENGTH: 300
<212> TYPE: PRT
<213> ORGANISM: Artificial Sequence
<220> FEATURE:
<223> OTHER INFORMATION: Derived from Volvox carteri VChR1

<400> SEQUENCE: 20
```

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

```
Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95

Phe Asp Ser Pro Ala Thr Leu Trp Leu Ser Gly Asn Gly Val Val
                    100                 105                 110

Trp Met Arg Tyr Gly Glu Trp Leu Leu Thr Ser Pro Val Leu Leu Ile
                    115                 120                 125

His Leu Ser Asn Leu Thr Gly Leu Lys Asp Asp Tyr Ser Lys Arg Thr
            130                 135                 140

Met Gly Leu Leu Val Ser Asp Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
            195                 200                 205

Val Met Ala Trp Thr Phe Phe Val Ala Trp Gly Met Phe Pro Val Leu
            210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 21
<211> LENGTH: 300
<212> TYPE: PRT
<213> ORGANISM: Artificial Sequence
<220> FEATURE:
<223> OTHER INFORMATION: Derived from Volvox carteri VChR1

<400> SEQUENCE: 21

Met Asp Tyr Pro Val Ala Arg Ser Leu Ile Val Arg Tyr Pro Thr Asp
1               5                   10                  15

Leu Gly Asn Gly Thr Val Cys Met Pro Arg Gly Gln Cys Tyr Cys Glu
            20                  25                  30

Gly Trp Leu Arg Ser Arg Gly Thr Ser Ile Glu Lys Thr Ile Ala Ile
            35                  40                  45

Thr Leu Gln Trp Val Val Phe Ala Leu Ser Val Ala Cys Leu Gly Trp
    50                  55                  60

Tyr Ala Tyr Gln Ala Trp Arg Ala Thr Cys Gly Trp Glu Glu Val Tyr
65                  70                  75                  80

Val Ala Leu Ile Glu Met Met Lys Ser Ile Ile Glu Ala Phe His Glu
                85                  90                  95
```

```
Phe Asp Ser Pro Ala Thr Leu Trp Leu Ser Ser Gly Asn Gly Val Val
                100                 105                 110

Trp Met Arg Tyr Gly Glu Trp Leu Leu Thr Cys Pro Val Leu Leu Ile
            115                 120                 125

His Leu Ser Asn Leu Thr Gly Leu Lys Asp Asp Tyr Ser Lys Arg Thr
130                 135                 140

Met Gly Leu Leu Val Ser Ala Val Gly Cys Ile Val Trp Gly Ala Thr
145                 150                 155                 160

Ser Ala Met Cys Thr Gly Trp Thr Lys Ile Leu Phe Phe Leu Ile Ser
                165                 170                 175

Leu Ser Tyr Gly Met Tyr Thr Tyr Phe His Ala Ala Lys Val Tyr Ile
            180                 185                 190

Glu Ala Phe His Thr Val Pro Lys Gly Ile Cys Arg Glu Leu Val Arg
        195                 200                 205

Val Met Ala Trp Thr Phe Phe Val Ala Trp Gly Met Phe Pro Val Leu
    210                 215                 220

Phe Leu Leu Gly Thr Glu Gly Phe Gly His Ile Ser Pro Tyr Gly Ser
225                 230                 235                 240

Ala Ile Gly His Ser Ile Leu Asp Leu Ile Ala Lys Asn Met Trp Gly
                245                 250                 255

Val Leu Gly Asn Tyr Leu Arg Val Lys Ile His Glu His Ile Leu Leu
            260                 265                 270

Tyr Gly Asp Ile Arg Lys Lys Gln Lys Ile Thr Ile Ala Gly Gln Glu
        275                 280                 285

Met Glu Val Glu Thr Leu Val Ala Glu Glu Asp
    290                 295                 300

<210> SEQ ID NO 22
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 22

Lys Ser Arg Ile Thr Ser Glu Gly Glu Tyr Ile Pro Leu Asp Gln Ile
1               5                   10                  15

Asp Ile Asn Val
            20

<210> SEQ ID NO 23
<211> LENGTH: 26
<212> TYPE: PRT
<213> ORGANISM: Artificial Sequence
<220> FEATURE:
<223> OTHER INFORMATION: Synthetic polypeptide

<400> SEQUENCE: 23

Met Asp Tyr Gly Gly Ala Leu Ser Ala Val Gly Arg Glu Leu Leu Phe
1               5                   10                  15

Val Thr Asn Pro Val Val Val Asn Gly Ser
            20                  25

<210> SEQ ID NO 24
<211> LENGTH: 27
<212> TYPE: PRT
<213> ORGANISM: Artificial Sequence
<220> FEATURE:
<223> OTHER INFORMATION: Synthetic polypeptide
```

<400> SEQUENCE: 24

Met Ala Gly His Ser Asn Ser Met Ala Leu Phe Ser Phe Ser Leu Leu
1               5                   10                  15

Trp Leu Cys Ser Gly Val Leu Gly Thr Glu Phe
            20                  25

<210> SEQ ID NO 25
<211> LENGTH: 23
<212> TYPE: PRT
<213> ORGANISM: Artificial Sequence
<220> FEATURE:
<223> OTHER INFORMATION: Synthetic polypeptide

<400> SEQUENCE: 25

Met Gly Leu Arg Ala Leu Met Leu Trp Leu Leu Ala Ala Ala Gly Leu
1               5                   10                  15

Val Arg Glu Ser Leu Gln Gly
            20

<210> SEQ ID NO 26
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 26

Met Arg Gly Thr Pro Leu Leu Leu Val Val Ser Leu Phe Ser Leu Leu
1               5                   10                  15

Gln Asp

<210> SEQ ID NO 27
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 27

Val Lys Glu Ser Leu
1               5

<210> SEQ ID NO 28
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 28

Val Leu Gly Ser Leu
1               5

<210> SEQ ID NO 29
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 29

Asn Ala Asn Ser Phe Cys Tyr Glu Asn Glu Val Ala Leu Thr Ser Lys
1               5                   10                  15

```
<210> SEQ ID NO 30
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 30

Phe Xaa Tyr Glu Asn Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 31

Phe Cys Tyr Glu Asn Glu Val
1               5

<210> SEQ ID NO 32
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 32

Met Thr Glu Thr Leu Pro Pro Val Thr Glu Ser Ala Val Ala Leu Gln
1               5                   10                  15

Ala Glu
```